US010497549B2

(12) United States Patent
Stephenson, Jr. et al.

(10) Patent No.: US 10,497,549 B2
(45) Date of Patent: *Dec. 3, 2019

(54) METHODS FOR MASS SPECTROMETRY OF MIXTURES OF PROTEINS OR POLYPEPTIDES USING PROTON TRANSFER REACTION

(71) Applicant: Thermo Finnigan LLC, San Jose, CA (US)

(72) Inventors: James L. Stephenson, Jr., Raleigh, NC (US); John E. P. Syka, Charlottesville, VA (US); August A. Specht, Pleasanton, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,439

(22) Filed: Dec. 4, 2017

(65) Prior Publication Data

US 2018/0102243 A1    Apr. 12, 2018

Related U.S. Application Data

(62) Division of application No. 15/327,128, filed as application No. PCT/US2015/040914 on Jul. 17, 2015, now Pat. No. 9,837,255.

(Continued)

(51) Int. Cl.
  *H01J 49/26*  (2006.01)
  *H01J 49/00*  (2006.01)
  (Continued)

(52) U.S. Cl.
  CPC ............ *H01J 49/0072* (2013.01); *C12Q 1/04* (2013.01); *G01N 33/6848* (2013.01); *H01J 49/0031* (2013.01); *H01J 49/0445* (2013.01)

(58) Field of Classification Search
  CPC ............... H01J 49/0072; H01J 49/0031; H01J 49/0445; G01N 33/6848; C12Q 1/04
  (Continued)

(56) References Cited

U.S. PATENT DOCUMENTS 7,064,317 B2   6/2006   McLuckey et al.
7,518,108 B2   4/2009   Frey et al.
(Continued)

FOREIGN PATENT DOCUMENTS

GB       2476603 A      6/2011
WO    02/086490 A2    10/2002
(Continued)

OTHER PUBLICATIONS

Blake et al., "Proton-Transfer Reaction Mass Spectrometry", Chem. Rev. 2009, 109, 861-896.
(Continued)

*Primary Examiner* — Nicole M Ippolito
(74) *Attorney, Agent, or Firm* — Thomas F. Cooney

(57) ABSTRACT

A method comprises: (1) making an extract of a biological sample; (2) repeatedly: (a) choosing a respective one of a plurality of pre-determined protein or polypeptide analyte compounds; (b) introducing a portion of the extract into an electrospray ionization source, thereby generating positive ions comprising a plurality of ion species; (c) isolating a plurality of subsets of the ion species comprising respective mass-to-charge (m/z) ratio ranges, each range including an m/z ratio corresponding to a respective protonation state of the chosen compound; (d) reacting the isolated plurality of subsets of first-generation ion species with proton transfer reaction reagent anions for a pre-determined time duration; (e) generating a mass spectrum of the product ion species; and (g) identifying either the presence or absence of the compound based on the mass spectrum; and (3) identifying (Continued)

the presence or absence of the microorganism within the sample based on analytes present.

11 Claims, 24 Drawing Sheets

Related U.S. Application Data

(60) Provisional application No. 62/026,187, filed on Jul. 18, 2014.

(51) Int. Cl.
  *G01N 33/68* (2006.01)
  *C12Q 1/04* (2006.01)
  *H01J 49/04* (2006.01)
(58) Field of Classification Search
  USPC .................................. 250/281, 282, 283, 288
  See application file for complete search history.

(56) References Cited

U.S. PATENT DOCUMENTS

| | | | |
|---|---|---|---|
| 7,550,718 B2 | 6/2009 | McLuckey et al. | |
| 7,749,769 B2 | 7/2010 | Hunt et al. | |
| 8,168,943 B2 | 5/2012 | Schwartz et al. | |
| 8,274,044 B2 | 9/2012 | Yoshioka et al. | |
| 8,283,626 B2 | 10/2012 | Brown et al. | |
| 8,334,503 B2 | 12/2012 | McLuckey et al. | |
| 8,440,962 B2 | 5/2013 | Le Blanc | |
| 9,837,255 B2* | 12/2017 | Stephenson, Jr. ........ | C12Q 1/04 |
| 2002/0172961 A1 | 11/2002 | Schneider et al. | |
| 2008/0093547 A1 | 4/2008 | Hartmer et al. | |
| 2008/0128607 A1 | 6/2008 | Herold et al. | |
| 2010/0084548 A1 | 4/2010 | McLuckey et al. | |
| 2011/0114835 A1 | 5/2011 | Chen et al. | |
| 2011/0189788 A1 | 8/2011 | Brown et al. | |
| 2012/0156707 A1 | 6/2012 | Hartmer et al. | |
| 2012/0205531 A1 | 8/2012 | Zabrouskov | |
| 2013/0084645 A1 | 4/2013 | Coon et al. | |
| 2014/0120565 A1 | 5/2014 | Coon et al. | |
| 2014/0357502 A1 | 12/2014 | Campbell et al. | |
| 2015/0293058 A1 | 10/2015 | Wuhr et al. | |
| 2015/0380231 A1 | 12/2015 | Brown et al. | |

FOREIGN PATENT DOCUMENTS

| | | |
|---|---|---|
| WO | 03/017319 A2 | 2/2003 |
| WO | 2006/042187 A2 | 4/2006 |
| WO | 2013/098603 A1 | 7/2013 |
| WO | 2013/112677 A2 | 8/2013 |
| WO | 2013/166169 A1 | 11/2013 |

OTHER PUBLICATIONS

Campbell et al., "Targeted Ion Parking for the Quantitation of Biotherapeutic Proteins: Concepts and Preliminary Data", J Am Soc Mass Spectrom 2010, 21, pp. 2011-2022.
Cargile et al., "Identification of Bacteriophage MS2 Coat Proteinfrom *E. coli* Lysates via Ion Trap Collisional Activation of Intact Protein Ions", Anal. Chem. 2001, 73, pp. 1277-1285.
Chrisman et al., "Parallel Ion Parking of Protein Mixtures", Anal. Chem. 2006, 78, pp. 310-316.
Chrisman et al., "Parallel Ion Parking: Improving Conversion of Parents to First-Generation Products in Electron Transfer Dissociation", Anal. Chem. 2005, 77 (10), pp. 3411-3414.
Coon et al., "Protein identification using sequential ionionreactions and tandem mass spectrometry", PNAS 2005, vol. 102 (27), 9463-9468.
He et al., "Dissociation of Multiple Protein Ion Charge States Following a Single Gas-Phase Purification and Concentration Procedure", Anal. Chem. 2002, pp. 4653-4661.

Horn, et al., "Automated Reduction and Interpretation of High Resolution Electrospray Mass Spectra of Large Molecules,"J. Am. Soc. Mass Spectrom., vol. 11, No. 4., (2000), pp. 320-332.
Liu et al., "Top-Down Protein Identification/Characterization of a Priori Unknown Proteins via Ion Trap Collision-Induced Dissociation and Ion/Ion Reactions in a Quadrupole/Time-of-Flight Tandem Mass Spectrometer", Anal. Chem. 2009, 81, pp. 1433-1441.
McLuckey et al., "Electrosprayilon Trap Mass Spectrometry for the Detection and Identification of Organisms", joint services workshop on biological mass spectrometry, Baltimore, MD (United States), Jul. 28-30, 1997, https://www.osti.gov/scitech/biblio/622805, pp. 1-8.
McLuckey et al., "Ion Parking during Ion/Ion Reactions in Electrodynamic Ion Traps", Anal. Chem. 2002, 74, pp. 336-346.
McLuckey et al., "Ion/Ion Chemistry of High-Mass Multiply Charged Ions", Mass Spectrometry Reviews, 1998, 17, pp. 369-407.
McLuckey et al., "Ion/Ion Proton-Transfer Kinetics: Implications forAnalysis of Ions Derived from Electrospray of Protein Mixtures", Anal. Chem. 1998, 70, pp. 1198-1202.
McLuckey et al., "Ion/Molecule Reactions for Improved Effective Mass Resolution in Electrospray Mass Spectrometry", Anal. Chem. 1995, 67, pp. 2493-2497.
Ogorzalek Loo et al., "Proton Transfer Reaction Studies of Multiply Charged Proteins in a High Mass-to-Charge Ratio Quadrupole Mass Spectrometer", J Am Soc Mass Spectrom 1994, 5, 1064-1071.
Reid et al., "Gas-Phase Concentration, Purification, and Identification ofWhole Proteins from Complex Mixtures", J. Am. Chem. Soc. 2002, 124, pp. 7353-7362.
Scalf et al., "Charge Reduction Electrospray Mass Spectrometry", Anal. Chem. 2000, 72, pp. 52-60.
Stephenson et al., "Charge Manipulation for Improved Mass Determination of High-mass Species and Mixture Components by Electrospray Mass Spectrometry", J. Mass Spectrom. 1998, 33, pp. 664-672.
Stephenson et al., "Ion-ion Proton Transfer Reactions of Bio-ions Involving Noncovalent Interactions: Holomyoglobin", J Am Soc Mass Spectrom 1997, 8, pp. 637-644.
Stephenson et al., "Ion/Ion Proton Transfer Reactions for ProteinMixture Analysis", Anal. Chem. 1996, 68, pp. 4026-4032.
Stephenson et al., "Ion/Ion Reactions for Oligopeptide Mixture Analysis: Application to Mixtures Comprised of 0.5-100 kDa Components", J Am Soc Mass Spectrom 1998, 9, pp. 585-596.
Stephenson et al., "Ion/Ion Reactions in the Gas Phase: Proton Transfer Reactions Involving Multiply-Charged Proteins", J. Am. Chem. Soc. 1996, 118, pp. 7390-7397.
Stephenson et al., "Simplification of Product Ion Spectra Derived from Multiply Charged Parent Ions via Ion/Ion Chemistry", Anal. Chem. 1998, 70, pp. 3533-3544.
Sutton et al., "Top-Down Analysis of the Low Molecular Weight Human Plasma Proteome Using Hybrid Ion Trap-Fourier Transform Mass Spectrometry", http://tools.thermofisher.com/content/sfs/brochures/AN-344-LC-MS-Human-Plasma-Proteome-AN62498-EN.pdf, 2007, pp. 1-6.
Xia et al., "Mutual Storage Mode Ion/Ion Reactions in a Hybrid Linear Ion Trap", J Am Soc Mass Spectrom 2005, 16, pp. 71-81.
Bern et al., "Identification of Peptides from Ion-Trap Data-Independent Tandem MS", Poster, Proceedings of the 56th ASMS Conference on Mass Spectrometry and Allied Topics, Denver, CO, Jun. 1-5, 2008.
Egertson et al., "Multiplexed MS /MS for improved data independentacquisition", Nature Methods, 2013, vol. 10 (8), pp. 744-748.
Gillet, et al., "Targeted Data Extraction of the MS/MS Spectra Generated by Data-independent Acquisition: A New for Concept for Consistent and Accurate Proteome Analysis", Molecular & Cellular Proteomics 11.6, 2012, pp. 1-17.
Kalli et al., "Evaluation and Optimization of Mass Spectrometric Settings During Data-dependent Acquisition Mode: Foucson LTQ-Orbitrap Mass Analyzers," J. Proteome Res., 2013, 12, pp. 3071-3086.
Kyowon et al., "UniNovo : A Universal Tool for de Novo Peptide Sequencing", Research in Computational Molecular Biology, Springer Berlin Heidelberg, XP047026500, 2013, pp. 100-117.

(56) References Cited

OTHER PUBLICATIONS

Panchaud et al., "Precursor Acquisition Independent From Ion Count: How to Dive Deeper into the Proteomics Ocean", Anal. Chem. 2009, 81, pp. 6481-6488.

Subramanian et al., "S1182 Serum Protein Signatures Determined by Mass Spectrometry (SELDI-ToF) Accurately Distinguishes Crohn's Disease (CD) from Ulcerative Colitis (UC)", Gastroenterology, Elsevier, Amsterdam, NL, vol. 134 (4), 2008, AGA Abstracts, p. A-196.

Venable et al., "Automated approach for quantitative analysis ofcomplex peptide mixtures from tandem mass spectra", Nature Methods, 2004, vol. 1 (1), pp. 1-7.

\* cited by examiner

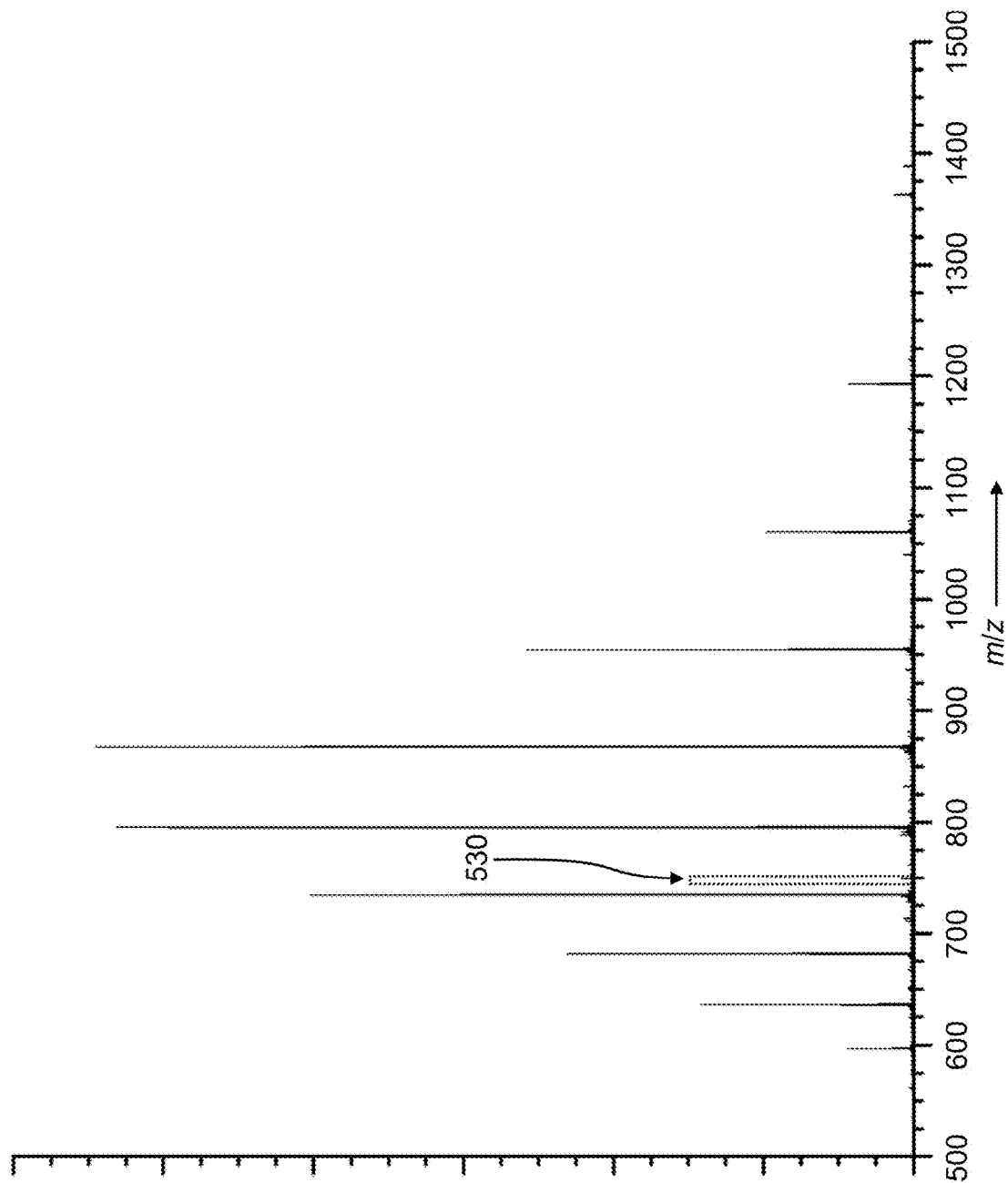

METHODS FOR MASS SPECTROMETRY OF MIXTURES OF PROTEINS OR POLYPEPTIDES USING PROTON TRANSFER REACTION

CROSS REFERENCE TO RELATED APPLICATIONS

This application is a Divisional of co-owned U.S. application for patent Ser. No. 15/327,128, now U.S. Pat. No. 9,837,255, having a 371(c) date of Jan. 18, 2017 and which is the U.S. National Stage of International Application No. PCT/US2015/040914 which was filed on Jul. 17, 2015 and which claims the benefit of the filing date of U.S. Provisional Application for Patent No. 62/026,187 which was filed on Jul. 18, 2014, the disclosures of said applications hereby incorporated by reference herein in their entireties.

TECHNICAL FIELD

The present invention relates to mass spectrometry and, more particularly, relates to methods for analyzing complex mixtures of proteins or polypeptides by mass spectrometry of proton transfer reaction product ions generated from proteins, polypeptides, and other biologically relevant multiply-charged species and the application of these methods to the identification and characterization of microorganisms.

BACKGROUND ART

In recent years, mass spectrometry has gained popularity as a tool for identifying microorganisms due to its increased accuracy and shortened time-to-result when compared to traditional methods for identifying microorganisms. To date, the most common mass spectrometry method used for microbial identification is matrix-assisted laser desorption ionization time-of-flight (MALDI-TOF) mass spectrometry. In MALDI-TOF, cells of an unknown microorganism are mixed with a suitable ultraviolet light absorbing matrix solution and are allowed to dry on a sample plate. Alternatively, an extract of microbial cells is used instead of the intact cells. After transfer to the ion source of a mass spectrometer, a laser beam is directed to the sample for desorption and ionization of the proteins and time-dependent mass spectral data is collected.

The mass spectrum of a microorganism produced by MALDI-TOF methods reveals a number of peaks from intact peptides, proteins, protein fragments, and other molecules that constitute the microorganism's "fingerprint". This method relies on the pattern matching of the peak profiles in the mass spectrum of an unknown microorganism to a reference database comprising a collection of mass spectra for known microorganisms obtained using essentially the same experimental conditions. The better the match between the spectrum of the isolated microorganism and a spectrum in the reference database, the higher the confidence level in identification of the organism at the genus, species, or in some cases, subspecies level. Because the method relies upon matching the patterns of peaks in MALDI-TOF mass spectra, there is no requirement to identify or otherwise characterize the proteins represented in the spectrum of the unknown microorganism in order to identify it.

Although MALDI-TOF methods are rapid and cost effective, they have limitations that restrict the range of applications to pathogen characterization and identification including but not limited to virulence detection and quantitation, resistance marker determination, strain matching, and antibiotic susceptibility testing to name a few. The information content within a MALDI mass spectrum reflects the most abundant and ionizable proteins which are generally limited to ribosomal proteins at the experimental conditions used. Because ribosomal proteins are highly conserved among prokaryotes, differentiation of closely related microorganisms by MALDI-TOF is limited. In this case many of the ribosomal proteins across closely related species contain either the same or slightly different amino acid sequences (i.e. single amino acid substitutions) that cannot be effectively differentiated with low resolution mass spectrometers. Moreover, determination of strain and/or serovar type, antibiotic resistance, antibiotic susceptibility, virulence or other important characteristics relies upon the detection of protein markers other than ribosomal proteins which further limits the application of MALDI-TOF for microbial analysis. Laboratories using MALDI-TOF for identification of microorganisms must use other methods to further characterize the identified microbes. In addition, the MALDI-TOF method's reliance upon matching spectral patterns requires a pure culture for high quality results and thus is not generally suitable for direct testing, mixed cultures, blood culture, or other complex samples containing different microorganisms.

Several other mass spectrometry methods for detection of microorganisms have been used. For example, mass spectrometry-based protein sequencing methods have been described wherein liquid chromatography is coupled to tandem mass spectrometry (LC-MS/MS) and sequence information is obtained from enzymatic digests of proteins derived from the microbial sample. This approach, termed "bottom-up" proteomics, is a widely practiced method for protein identification. The method can provide identification to the subspecies or strain level as chromatographic separation allows the detection of additional proteins other than just ribosomal proteins, including those useful for characterization of antibiotic resistance markers and virulence factors.

In contrast to "bottom-up" proteomics, "top-down" proteomics refers to methods of analysis in which protein samples are introduced intact into a mass spectrometer, without enzymatic, chemical or other means of digestion. Top-down analysis enables the study of the intact protein, allowing identification, primary structure determination and localization of post-translational modifications (PTMs) directly at the protein level. Top-down proteomic analysis typically consists of introducing an intact protein into the ionization source of a mass spectrometer, fragmenting the protein ions and measuring the mass-to-charge ratios and abundances of the various fragments so-generated. The resulting fragmentation is many times more complex than a peptide fragmentation, which may, in the absence of the methods taught herein, necessitate the use of a mass spectrometer with very high mass accuracy and resolution capability in order to interpret the fragmentation pattern with acceptable certainty. The interpretation generally includes comparing the observed fragmentation pattern to either a protein sequence database that includes compiled experimental fragmentation results generated from known samples or, alternatively, to theoretically predicted fragmentation patterns. For example, Liu et al. ("Top-Down Protein Identification/Characterization of a Priori Unknown Proteins via Ion Trap Collision-Induced Dissociation and Ion/Ion Reactions in a Quadrupole/Time-of-Flight Tandem Mass Spectrometer", *Anal. Chem.* 2009, 81, 1433-1441) have described top-down protein identification and characterization of both modified and unmodified unknown proteins with masses up to ≈28 kDa.

An advantage of a top-down analysis over a bottom-up analysis is that a protein may be identified directly, rather than inferred as is the case with peptides in a bottom-up analysis. Another advantage is that alternative forms of a protein, e.g. post-translational modifications and splice variants, may be identified. However, top-down analysis has a disadvantage when compared to a bottom-up analysis in that many proteins can be difficult to isolate and purify. Thus, each protein in an incompletely separated mixture can yield, upon mass spectrometric analysis, multiple ion species, each species corresponding to a different respective degree of protonation and a different respective charge state, and each such ion species can give rise to multiple isotopic variants. Thus, methods are required for interpreting the resulting highly complex mass spectra.

Ion-ion reactions have found great utility in the field of biological mass spectrometry over the last decade, primarily with the use of electron transfer dissociation (ETD) to dissociate peptide/proteins and determine primary sequence information and characterize post-translational modifications.

Proton transfer, another type of ion-ion reaction, has also been used extensively in biological applications. Experimentally, proton transfer is accomplished by causing multiply-positively-charged protein ions (i.e., protein cations) from a sample to react with singly-charged reagent anions so as to reduce the charge state of an individual protein cation and the number of such charge states of the protein cations. These reactions proceed with pseudo-first order reaction kinetics when the reagent anions are present in large excess over the protein cation population. The rate of reaction is directly proportional to the square of charge of the protein cation (or other multiply-charged cation) multiplied by the charge on the reagent anion. The same relationship also holds for reactions of the opposite polarity, defined here as reaction between singly-charged reagent cations and a population of multiply-charged anions derived from a protein sample. This produces a series of pseudo-first order consecutive reaction curves as defined by the starting multiply-charged protein cation population. Although the reactions are highly exothermic (in excess of 100 kcal/mol), proton transfer is an even-electron process performed in the presence of 1 mtorr of background gas (i.e. helium) and thus does not fragment the starting multiply-charged protein cation population. The collision gas serves to remove the excess energy on the microsecond time scale ($10^8$ collisions per second), thus preventing fragmentation of the resulting product ion population.

Proton transfer reactions (PTR) have been used successfully to identify proteins in mixtures of proteins. This mixture simplification process has been employed to determine charge state and molecular weights of high mass proteins. PTR has also been utilized for simplifying product ion spectra derived from the collisional-activation of multiply-charged precursor protein ions. Although PTR reduces the overall signal derived from multiply-charged protein ions, this is more than offset by the significant gain in signal-to-noise ratio of the resulting PTR product ions. The PTR process is 100% efficient leading to only single series of reaction products, and no side reaction products that require special interpretation and data analysis.

Various aspects of the application of PTR to the analysis of peptides, polypeptides and proteins have been described in the following documents: U.S. Pat. No. 7,749,769 B2 in the names of inventors Hunt et al., U.S. Patent Pre-Grant Publication No. 2012/0156707 A1 in the names of inventors Hartmer et al., U.S. Pre-Grant Publication No. 2012/0205531 A1 in the name of inventor Zabrouskov; McLuckey et al., "Ion/Ion Proton-Transfer Kinetics: Implications for Analysis of Ions Derived from Electrospray of Protein Mixtures", *Anal. Chem.* 1998, 70, 1198-1202; Stephenson et al., "Ion-ion Proton Transfer Reactions of Bio-ions Involving Noncovalent Interactions: Holomyoglobin", *J. Am. Soc. Mass Spectrom.* 1998, 8, 637-644; Stephenson et al., "Ion/Ion Reactions in the Gas Phase: Proton Transfer Reactions Involving Multiply-Charged Proteins", *J. Am. Chem. Soc.* 1996, 118, 7390-7397; McLuckey et al., "Ion/Molecule Reactions for Improved Effective Mass Resolution in Electrospray Mass Spectrometry", *Anal. Chem.* 1995, 67, 2493-2497; Stephenson et al., "Ion/Ion Proton Transfer Reactions for Protein Mixture Analysis", *Anal. Chem.* 1996, 68, 4026-4032; Stephenson et al., "Ion/Ion Reactions for Oligopeptide Mixture Analysis: Application to Mixtures Comprised of 0.5-100 kDa Components", *J. Am. Soc. Mass Spectrom.* 1998, 9, 585-596; Stephenson et al., "Charge Manipulation for Improved Mass Determination of High-mass Species and Mixture Components by Electrospray Mass Spectrometry", *J. Mass Spectrom.* 1998, 33, 664-672; Stephenson et al., "Simplification of Product Ion Spectra Derived from Multiply Charged Parent Ions via Ion/Ion Chemistry", *Anal. Chem.*, 1998, 70, 3533-3544 and Scalf et al., "Charge Reduction Electrospray Mass Spectrometry", *Anal. Chem.* 2000, 72, 52-60. Various aspects of general ion/ion chemistry have been described in McLuckey et al., "Ion/Ion Chemistry of High-Mass Multiply Charged Ions", *Mass Spectrom. Rev.* 1998, 17, 369-407 and U.S. Pat. No. 7,550,718 B2 in the names of inventors McLuckey et al. Apparatus for performing PTR and for reducing ion charge states in mass spectrometers have been described in U.S. Pre-Grant Publication No. 2011/0114835 A1 in the names of inventors Chen et al., U.S. Pre-Grant Publication No. 2011/0189788 A1 in the names of inventors Brown et al., U.S. Pat. No. 8,283,626 B2 in the names of inventors Brown et al. and U.S. Pat. No. 7,518,108 B2 in the names of inventors Frey et al. Adaptation of PTR charge reduction techniques to detection and identification of organisms has been described by McLuckey et al. ("*Electrospray/Ion Trap Mass Spectrometry for the Detection and Identification of Organisms*", Proc. First Joint Services Workshop on Biological Mass Spectrometry, Baltimore, Md., 28-30 Jul. 1997, 127-132).

The product ions produced by the PTR process can be accumulated into one or into several charge states by the use of a technique known as "ion parking". Ion parking uses supplementary AC voltages to consolidate the PTR product ions formed from the original variously protonated ions of any given protein molecule into a particular charge state or states at particular mass-to-charge (m/z) values during the reaction period. This technique can be used to concentrate the product ion signal into a single or limited number of charge states (and, consequently, into a single or a few respective m/z values) for higher sensitivity detection or further manipulation using collisional-activation, ETD, or other ion manipulation techniques. Various aspects of ion parking have been described in U.S. Pat. No. 7,064,317 B2 in the name of inventor McLuckey; U.S. Pat. No. 7,355,169 B2 in the name of inventor McLuckey; U.S. Pat. No. 8,334,503 B2 in the name of inventor McLuckey; U.S. Pat. No. 8,440,962 B2 in the name of inventor Le Blanc; and in the following documents: McLuckey et al., "Ion Parking during Ion/Ion Reactions in Electrodynamic Ion Traps", *Anal. Chem.* 2002, 74, 336-346; Reid et al., "Gas-Phase Concentration, Purification, and Identification of Whole Proteins from Complex Mixtures", *J. Am. Chem. Soc.* 2002, 124, 7353-7362; He et al., "Dissociation of Multiple Protein Ion Charge States Following a Single Gas-Phase Purification and Concentration Procedure", *Anal. Chem.* 2002, 74, 4653-4661; Xia et al., "Mutual Storage Mode Ion/Ion Reactions in a Hybrid Linear Ion Trap", *J. Am. Soc. Mass. Spectrom.* 2005, 16, 71-81; Chrisman et al., "Parallel Ion Parking: Improving Conversion of Parents to First-Generation Products in Electron Transfer Dissociation", *Anal. Chem.* 2005, 77(10), 3411-3414 and Chrisman et al., "Parallel Ion Parking of Protein Mixtures", *Anal. Chem.* 2006, 78, 310-316.

DISCLOSURE OF INVENTION

The present disclosure teaches an application of ion-ion reaction chemistry in which proton transfer reactions are employed to simplify the mass spectrometric analysis of complex ion populations derived from electrospray ionization of samples comprising mixtures of compounds extracted from microorganisms. The inventors have discovered that by subjecting a mass-to-charge-restricted subset of such ions to PTR, the resulting population of product ions comprises a much simpler population of charge states of lower total charge values (where the words "lower" or "reduced", in this context, refer to lower or reduced in terms of absolute value) which can be readily resolved and assigned to specific protein or peptide ions. Because the PTR product ions represent a smaller subset of multiply-charged species derived from a complex mixture of charge states than the original precursor ions, mass spectral interpretation is greatly simplified and target analysis using tandem mass spectrometry (MS/MS or MS") can be performed on a single protein or other component(s) derived from a microbial extract.

The charge-reduced protein and peptide product ions resulting from a given proton transfer reaction produce mass-to-charge (m/z) values that are greater than those of the original m/z values. For a mixture of protein ions that have the same m/z value but differing mass and charge, the mixture can be separated on the micro- or millisecond timescale. Further, these multiply-charged protein ions of the same m/z value with differing mass and charge can be separated from low m/z value background ions derived from small molecules, lipids, solvents, or other interferents based on the charge squared dependence of the reaction. Multiply-charged ions are therefore separated in time from the background signal thus producing a separated protein mixture at highly increased signal-to-noise (s/n) ratio. The inventors have discovered that, as a result of these two factors, the spectral signatures of the protein/peptide or any other analyte product ions may be significantly separated from those of most interferent ions. In addition, multiple stages of PTR reactions can be performed to separate protein mixtures on low resolution instrumentation, such as a linear ion trap mass spectrometer, in order to simplify and isolate these proteins and other analytes such that target analysis can be performed via MS" analysis. The inventors have further discovered that the advantageous properties of simple PTR reactions may be even further amplified by performing "ion parking" procedures in conjunction with PTR reaction, thus enabling an analyst to at least partially select or control the product-ion charge state distribution that results from the PTR reaction.

PTR can also be used to improve high mass performance in mass spectrometry. In mass spectrometry, an ion may be assigned either an integer nominal mass or mass-to-charge ratio or an accurate or exact mass or mass-to-charge ratio. Accurate or exact masses or mass-to-charge ratios can be considered as comprising an integer component or value and a decimal component or value. Atomic and molecular masses are measured in units of daltons (Da) and m/z ratio values are generally given in units of daltons per elementary charge, or Dale or thomson (Th). It is to be noted that, in instances of described numerical values of m/z ratios in this document, such ratios are understood to be provided in units of daltons per elementary charge, or Th. Accurate or exact (i.e. non-integer) masses or m/z ratios can be represented as an integer nominal mass or mass-to-charge ratio value or component together with a corresponding decimal component. Thus, as used in this document, accurate mass determination or mass analysis can be considered as comprising sub-integer accuracy, i.e. accuracy of ±0.5 Da or better and, preferably, 0.1 Da or better.

Alternatively, accurate or exact masses or m/z ratios may be defined in terms of parts-per-million (ppm) mass accuracy. For mass spectrometric determinations of polypeptides and proteins, an experimental mass accuracy of 50 ppm or better, more preferably 10 ppm or better and, still more preferably 1 ppm or better, is generally required because such molecules and their ions frequently have molecular or ionic weights of at least 10,000 Da and as much as 100,000 Da. Thus, as used in this document, accurate mass determination or mass analysis can alternatively be considered as comprising an accuracy of 50 ppm or better, more preferably 10 ppm or better and, still more preferably, 1 ppm or better.

In addition to improving the signal-to-noise ratios for this type of analysis, the inventors have considered that the reduction of charge on protein ions causes these large ions to refold in the gas phase, as has been described in Zhao et al., "Effects of Ion/Ion Proton Transfer Reactions on Conformation of Gas-Phase Cytochrome c Ions", *J. Am. Soc. Mass Spec.* 2010, 21, 1208-1217. It is believed that this results in a more compact configuration which reduces the collisional cross section of the protein ions and, accordingly, increases their stability against fragmentation by collision with background gas molecules present in the mass analyzer chamber. The inventors have discovered that this effect can be especially beneficial with mass analyzers that employ image current detection, such as is done in a Fourier-transform ion cyclotron resonance (FT-ICR) mass analyzer or in an Orbitrap™ mass analyzer (a type of electrostatic trap mass analyzer commercially available from Thermo Fisher Scientific of Waltham, Mass. USA). Another potential reason for improved high mass performance is the large deposition of energy into a given protein ion that results from the PTR process. The energy deposited as a result of the PTR process exceeds 100 kcal/mol and is then effectively dampened by the presence of collision energy. This rapid heating process "boils off" neutral molecules that may be attached to the protein via ion-dipole, ion-induced dipole, or dipole-induced dipole interactions. Most importantly, the reduction of charge state for high mass proteins may significantly improve the transfer of these ions from the relatively high pressure of an ion guide, ion storage or ion trapping device where the PTR process is commonly performed, to a lower-pressure region of a mass analyzer, such as an Orbitrap™ mass analyzer. The reduced charge state means that ions are transferred at less kinetic energy thus limiting ion scattering, direct fragmentation, or formation of metastable species. The inventors further consider that this latter property is especially significant in enabling high-accuracy mass analysis of the PTR product ions in an accurate-mass spectrometer—such as the Orbitrap™-type of electrostatic trap mass analyzer—that detects image currents produced by cyclic ionic motion over an extended time range.

The present teachings are especially useful for the analysis and identification of intact proteins having molecular weight in excess of 50 kDa. The inventors have discovered the surprising result that, taken together, the various advantageous factors noted above can enable accurate identification of multiple intact proteins or large peptides from even very complex mixtures derived from natural microorganism samples. Such identifications can enable microorganism identification to the species, subspecies or even strain level. The target protein or polypeptide ion single species or multiple species may be chosen so as to be indicative, based on prior knowledge or information, either individually or in combination, of the presence in a sample of a specific microorganism or cell type, or a specific strain or variant of a microorganism or cell type, or a given virulence factor or toxin, or of the capacity of a microorganism or cell to resist an antimicrobial compound or antibiotic drug.

The present invention, in one aspect, offers an alternative to traditional bottom-up proteomics methods, namely top-down analysis of intact proteins derived from microbial cells via a method which is applicable to substantially all microorganisms including Gram-positive bacteria, Gram-negative bacteria, mycobacteria, *mycoplasma*, yeasts, protozoans, filamentous (i.e., microscopic) fungi. The present invention provides identification of microorganisms at the genus, species, subspecies, strain pathovar, and serovar level even in samples containing mixtures of microorganisms and/or microorganisms analyzed directly from pure and/or mixed cultures and from direct samples (e.g., surface swabs, bodily fluids, etc.). In addition, the approaches taught herein can be employed for targeted detection of virulence factors, antibiotic resistance and susceptibility markers, or other characteristics. The top-down methods of the present teachings are simple and quick because there is no need for chemical or enzymatic digestion of a sample and data processing is accomplished in real time.

Methods in accordance with the present teachings may comprise at least one or more of the following steps: microbial cell disruption, solubilization of proteins, sample clean-up (to desalt, remove insoluble components and debris, and/or concentrate), sample infusion or flow injection, fast partial liquid chromatographic separation, standard chromatographic separation, isoelectric focusing, ionization of proteins in solution, isolation of a given m/z range of the ions, causing the isolated range of ions to undergo PTR so as to form first-generation PTR product ions, optional isolation of an m/z range of the first-generation PTR product ions, optional mass spectrometry in MS or MS/MS mode, optionally causing the isolated range of first-generation PTR product ions to undergo a second PTR reaction so as to form second-generation PTR product ions, mass spectrometry in MS or MS/MS mode, and microbial identification via molecular weight analysis and/or protein sequence analysis, or using any statistical classification method. Preferably, but not necessarily, the mass spectrometry steps are performed with a high-resolution, high-accuracy mass spectrometer, such as a mass spectrometer comprising an Orbitrap™ mass analyzer.

Because a common method using a limited set of chemical reagents is performed, the methods of the present teachings are suitable for use within a completely automated system for sample preparation and mass spectrometry. Ideally, these methods may be automated from sample preparation through results reporting. Results may be automatically transferred to a hospital's electronic medical records system where they can be directly linked to patient treatment strategies, insurance, billing, or used in epidemiological reporting. Such an integrated system facilitates epidemiological tracking of an outbreak at the hospital, local, regional, and global levels. For high throughput laboratories, multiple systems can be interfaced to a central computer which integrates data from the different instruments prior to reporting. The system can import phenotypic susceptibility data where it can be combined with identification, virulence, antibiotic resistance and typing information generated by the invention.

Accordingly, in a first aspect, there is disclosed a method for identifying the presence or absence of a protein/polypeptide or other biologically relevant compound within a liquid sample comprising a mixture of compounds that includes a plurality of protein compounds or a plurality of polypeptide compounds or pluralities of both protein and polypeptide or other compounds, wherein the method comprises: (i) making an extract of a biological sample; (ii) repeatedly: (a) choosing a respective one of a plurality of pre-determined protein or polypeptide analyte compounds; (b) introducing a portion of the extract into an electrospray ionization source, thereby generating positive ions comprising a plurality of ion species; (c) isolating a plurality of subsets of the ion species comprising respective mass-to-charge (m/z) ratio ranges, each range including an m/z ratio corresponding to a respective protonation state of the chosen compound; (d) reacting the isolated plurality of subsets of first-generation ion species with proton transfer reaction reagent anions for a pre-determined time duration; (e) generating a mass spectrum of the product ion species; and (g) identifying either the presence or absence of the compound based on the mass spectrum; and (iii) identifying the presence or absence of the microorganism within the sample based on analytes present.

In a second aspect, a mass spectrometer system is provided, the system comprising: (1) an electrospray ionization source fluidically coupled to a source of sample; (2) a mass filter configured to receive sample ions generated by the electrospray ion source; (3) a source of proton transfer reaction (PTR) reagent anions; (4) an ion trap configured to receive at least a portion of the sample ions from the mass filter and to receive the PTR reagent anions from the PTR reagent anion source; (5) a mass analyzer and detector configured to receive and analyze product ions generated by mixing of the sample ions and PTR reagent anions in the ion trap; and (6) an electronic control unit or processor electrically coupled to the source of PTR ions, the ion trap, and the mass analyzer and detector, the electronic control unit or processor comprising machine readable program instructions operable to: (a) cause the mass filter to isolate a plurality of subsets of the sample ions comprising respective mass-to-charge (m/z) ratio ranges, wherein each m/z ratio range includes an m/z ratio corresponding to a respective protonation state of a pre-determined analyte compound; (b) cause the isolated plurality of subsets of the sample ions to be reacted, for a predetermined time duration, with PTR reagent anions so as to generate product ions; (c) cause the mass analyzer to generate a mass spectrum of the product ions; and (d) identify either the presence of the chosen analyte compound within the sample if the mass spectrum comprises one or more lines at respective predetermined m/z ratios having intensities above a predetermined threshold or, otherwise, the absence of the analyte compound within the sample. In embodiments, the electronic control unit or processor may further comprise machine readable program instructions operable to: cause the repeated execution of steps (a) through (d), each repetition of the step (a) corresponding to a different respective protein or polypeptide analyte compound; and identify the presence of a microorganism within the sample if the presence of each predetermined protein or polypeptide analyte compound within the sample is identified or, otherwise, identify the absence of the microorganism within the sample.

The term "real-time spectral deconvolution" in the above refers to spectral deconvolution of mass spectral data that is performed concurrently with the mass spectral experiment or analytical run that generates (or that has generated) that mass spectral data. For example, mass spectral data acquired by mass analysis of analytes that elute at a first retention chromatographic retention time during a gradient elution may be deconvoluted, so as to identify the analytes, simultaneously with the continued collection of additional mass spectral data of additional analytes that elute at a second, later retention time during the same gradient elution. Likewise, deconvolution of the additional mass spectral data, so as to identify the additional analytes, may be performed simultaneously with the continued collection of mass spectral data of analytes that elute at a third elution time during the same gradient elution. The real-time spectral deconvolution may be facilitated by the use of a fast computer, such as a computer that employs parallel processing or a graphics processing unit (GPU) to perform the necessary calculations. Alternatively or additionally, the real-time spectral deconvolution may be facilitated by the use of a computationally efficient or optimized algorithm, such as an algorithm that is written at least partially in assembly language or that makes extensive use of in-cache look-up-tables.

More generally, the term "real-time" may be understood as meaning, when used in reference to an event or activity associated with a data acquisition process, that the event or activity occurs while some aspect or sub-process of that data acquisition process is ongoing. The data acquisition process itself may include one of more the following individual sub-processes: sample purification (e.g., solid phase extraction, size-exclusion chromatography); sample separation (e.g., chromatography); sample transfer into a mass spectrometer (e.g., infusion or inletting of eluate from a chromatograph); sample ionization in an ion source to as to generate first-generation ions; selection and isolation of ions for further manipulation; causing fragmentation of sample-derived ions or reaction of sample-derived ions with reagent ions so as to generate a first-generation of product ions; optional selection and isolation of product ions; optional further fragmentation of product ions or further reaction of product ions; transfer of ions (first-generation ions or first-generation or subsequent-generation product ions) to a mass analyzer, detection and measurement of ion mass-to-charge ratios by a detector of the mass analyzer; and transfer of data derived from the detection and measurement to a digital processor for storage, mathematical analysis, etc. The events or activities that may occur in "real-time", so defined, may include, but are not necessarily limited to: determination or identification of the presence of an analyte in a sample; identification or determination of the presence of a microorganism in a sample and providing a notification to a user of the identification or determination of the presence of an analyte or microorganism in a sample.

The above-described and various other features and advantages of the present teachings will become more fully apparent from the following description and appended claims, or may be learned by the practice of the invention as set forth hereinafter.

BRIEF DESCRIPTION OF DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 11A is a full scan mass spectrum of first-generation ions generated from eluate at a retention time of 18 min. and 9 s. during the course of a thirty-minute gradient reverse-phase liquid chromatography separation;

MODES FOR CARRYING OUT THE INVENTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the claims. The particular features and advantages of the invention will become more apparent with reference to the appended FIGS. 1-11 taken in conjunction with the following description.

Figure 1:
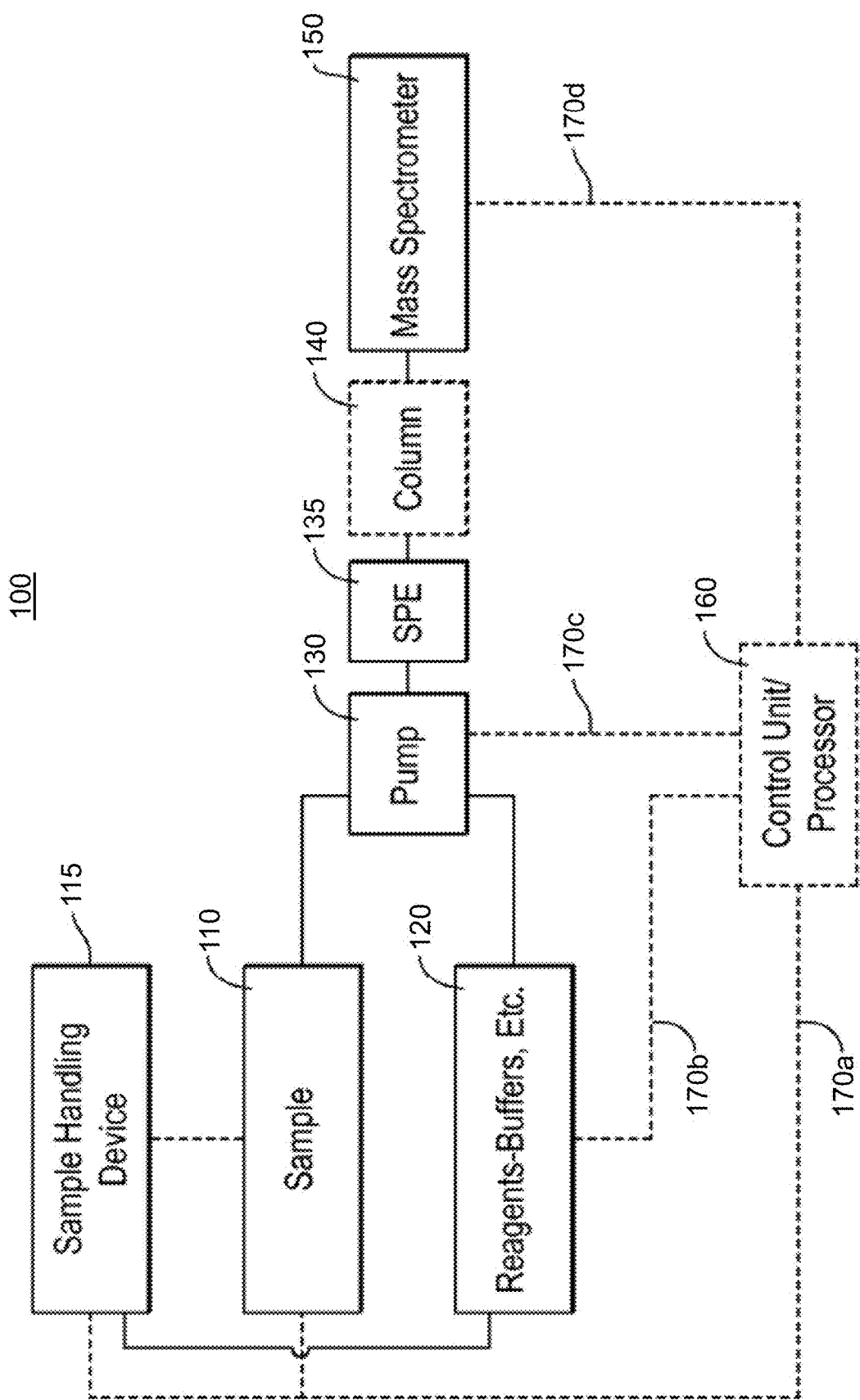
FIG. 1 is a block diagram schematically illustrating a system for rapid extraction and analysis of soluble proteins from at least one microorganism for identifying the at least one microorganism.

Referring now to FIG. 1, a system 100 for extraction of proteins from one or more microorganisms, detection of the proteins, and identification of the one or more microorganisms is schematically illustrated. The system 100 includes a sample handling device 115, a sample 110 that is accessible by the sample handling device 115, and sources of reagents, buffers, and the like 120, these sources being fluidly coupled to the sample handling device 115 by various tubing or other transfer lines. The system 100 further includes a first and, optionally, a second sample-purification device 135 (such as a solid phase extraction cartridge) configured for cleaning up samples (e.g., desalting, removing contaminants, concentrating proteins) and an optional chromatography column 140 that may be configured for at least partially purifying a sample 110 by liquid chromatography prior to mass-spec analysis. At least one sample-purification device 135 can comprise an in-line size exclusion chromatography column that can be used to not only remove salts but small molecules and lipids as well. The sample 110, the first and optional second sample-purification devices 135, and the optional chromatography column 140 are in fluid communication with a fluid handling pump 130, the various reagents, buffers and other fluids 120, and a mass spectrometer 150.

The sample handling device 115 is capable of preparing a range of sample types containing one or more microbes and delivering a soluble protein fraction extracted from the microbes to the mass spectrometer 150 for analysis. A sample 110 may be of any type suspected to contain one or more microorganisms including, without limitation, isolated colonies from a culture plate, cells from liquid growth medium, blood, blood culture, saliva, urine, stool, sputum, wound and body site swabs, soil, food, beverage, water, air, and environmental surface swabs.

The sample handling device 115 may include one or more of a cell disruption means, a robotic liquid handling means, a centrifuge, filtration means, an incubator, mixing means, a vacuum pump, a fluid pump, and reagents 120 that can be used for disruption of microbes and isolation of a soluble protein fraction. Disruption of bacterial, fungal, *mycoplasma* cells, viruses, and the like may be achieved by mechanical, chemical, enzymatic and other means as are commonly known in the art. Mechanical approaches include bead beating, use of pressure like French press and the like, sonication or other methods known in the art. Chemical methods include exposure to chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution.

As illustrated in FIG. 1, the system 100 further includes an optional control unit 160 that can be linked to various components of the system 100 through linkages 170a-170d. For example, the control unit 160 can be linked to the sample 110 to control sample application, the reagents 120 to control the application of various reagents, the pump 130 to control fluid handling, flow rates, etc., to the sample handling device 115 to control sample preparation, and to the mass spectrometer 150 to control mass spectrometry parameters. In the illustrated embodiment, the control unit 160 can also serve as a data processing unit to, for example, process data from the mass spectrometer 150 or to forward the data to server(s) for processing and storage (the server is not shown in FIG. 1). Control unit 160 can also determine molecular weights and charge states of any generation of PTR product ions for MS/MS, MS$^n$, or molecular weight determination in real time. The Control Unit 160 can also be used to automatically forward the results to health care professionals.

In some embodiments, the system 100 is designed to be used by a clinician or a general laboratory technician who is not necessarily expert in all aspects of sample preparation, LC-MS operations, LC-MS methods development, and the like. As such, the control unit 160 can be designed to encapsulate the data system environment by providing a user with a simplified application interface that can be used to initiate and monitor essentially all aspects of assaying a sample 110 without requiring the user to interact with the overall hardware and control systems of the system 100. The control unit 160 is therefore configured to provide a degree of separation between the user and the underlying services that control devices, data files and algorithms for translating data to a user readable form. That is, the control unit 160 eliminates the need for the user to be aware of or in control of hardware for analyzing clinical samples and provides a simplified interface to send and receive information from the mass spectrometer.

The control unit 160 may be configured to internally monitor each sample analysis request and is capable of tracking the analysis request from start to finish through the system 100. Once data for a sample 110 is being acquired or has been acquired by the system 100, the control unit 160 may be configured to automatically start post processing the data based on the type of assay selected by the user. Most importantly, the control unit 160 can be configured to process data in real time during the acquisition process. Here results are returned to the user in real-time that include microbial identification, virulence and resistance characterization, strain matching features, and data on antibiotic susceptibility testing. Moreover, the control unit 160 can be configured to automatically select post-processing parameters based on the type of assay selected by the user, further reducing the need for the user to interact with the system once the assay has been selected and started for analysis. The control unit 160 can be designed as a layer that fits between the system 100 and the user to reduce the complexity needed to set up sample assays for acquisition. The control system 160 can also be configured to return only the most relevant data to the user to avoid overwhelming the user with extraneous information.

In one embodiment, the system 100 can further include a sample detection device (not pictured) operably coupled to or integrated with the sample handling device 115. The sample detection device can work with the sample handling device 115 or independently of the sample handling device 115 perform at least one of the following functions: i. identify samples entering the system; ii. identify assay types for the samples entering the system; iii. select an assay protocol based on the anticipated assay type and/or analyte of interest; iv. direct the sample handling device and/or the control system to initiate analysis of the analyte of interest in the sample; v. direct the control system to select one or more reagents based upon the assay protocol selected for the type of assay and/or analyte of interest; vi. direct the control system to select a liquid chromatography mobile phase condition based upon the assay protocol selected for the type of assay and/or analyte of interest and cause the liquid chromatography system to perform the assay and/or purify the analyte of interest; vii. direct the control system to select a mass spectrometer setting based upon the assay protocol selected for the assay type and/or analyte of interest and cause the mass spectrometer to create mass spectral data associated with the selected assay type and/or analyte of interest; and viii. direct the control system to analyze the mass spectral data associated with the selected assay type and/or analyte of interest to identify the presence and/or concentration of the analyte of interest.

The sample, or the processed sample, may be cleaned up and or purified prior to analysis by mass spectrometry. Such purification, or sample clean-up, may refer to a procedure that removes salts or lipids from the crude cell extract, or to a procedure that enriches one or more analytes of interest relative to one or more other components of the sample. It also may refer to sample processing and clean-up in a separate laboratory that has biosafety level-three facilities for handling mycobacteria or filamentous fungi. In this embodiment samples are transferred to the system and can be analyzed as described previously. In one embodiment, such purification, or sample clean-up, may be accomplished by a solid phase extraction device, in-line size exclusion chromatography and/or the optional chromatography column 140.

In one embodiment, the first and/or second sample-purification device 135 may include a solid phase extraction (SPE) cartridge. In some embodiments, the SPE cartridge may be in line directly with the high resolution/high mass accuracy mass spectrometer 150. In one embodiment, the SPE cartridge may be a polypropylene tip with a small volume of silica or other sorbent containing bonded $C_4$, $C_8$ or $C_{18}$ or other functional groups immobilized in the cartridge, for example, a StageTip™ cartridge (Thermo Fisher Scientific). In alternative embodiments, polymeric sorbents or chelating agents may be used. The bed volume may be as small as 1 μL or less but greater volumes may also be used. The apparatus and method are well suited to the complex samples derived from the microbial cells because each SPE cartridge is used only once, minimizing carryover problems from one sample to another.

In one embodiment, a sample-purification device 135 may be an in-line size-exclusion chromatography column designed to remove salts, small molecules, and lipids from the sample 110. The approach can be used to separate medium and large molecular weight proteins as well. Phases are selected to be compatible with partial (i.e., less than 100 percent) organic solutions and organic acids. Phases can accommodate protein size distributions that differ in molecular weight from $10^3$ to $10^8$ Da. Flow rates are adjusted in real time to effect separation of intact proteins from small molecules with separation flow rates typically much less than the higher flow rates used to remove small molecules, lipids, and salts from the system. In this embodiment, a sample-purification device 135 may also be heated to facilitate faster diffusion rates for intact proteins, thus significantly shortening run times. The flow of mobile phase through a sample-purification device 135 may also be diverted during a portion of the clean-up process to remove certain impurities from the flow stream and prevent them from entering the mass spectrometer 150.

In one embodiment, the optional chromatography column 140 may include a column configured for at least partial chromatographic separation of the proteins in the sample. The stationary phase in the chromatography column may be porous or non-porous silica or agarose particles, or a monolithic material polymerized or otherwise formed inside the column. The stationary phase may be coated with an appropriate material such as $C_{18}$, $C_8$, $C_4$ or another suitable derivative, or contain cation exchanger or other material, or the combination of the above to facilitate the separation of the proteins, and such material may be chemically bonded to the particles or monolith inside the column. Particle sizes typically range from about 1.5 μm to 30 μm. Pore sizes can range from 50 to 300 angstroms. Inside diameters of columns typically range from about 50 μm to 2.1 mm, and column length from about 0.5 cm to 25 cm, or other. The mobile phase or eluent may be a pure solvent, or a mixture of two or more solvents, and may contain added salts, acids and/or other chemical modifiers. The proteins are separated on the column based on one or more physiochemical properties, including size, net charge, hydrophobicity, affinity, or other physiochemical properties. Chromatographic separation methods include one or more of ion exchange, size exclusion, HILIC, hydrophobic interaction, affinity, normal-phase, or reverse-phase chromatography.

Additional methods of purifying the samples may include, without limitation, liquid chromatography, HPLC, UHPLC, precipitation, solid-phase extraction, liquid-liquid extraction, dialysis, affinity capture, electrophoresis, filtration, ultra-filtration or other suitable methods known in the art for purification.

Various methods have been described involving the use of HPLC for sample clean-up prior to mass spectrometry analysis. One of skill in the art can select HPLC instruments and columns that are suitable for use in the invention. The chromatographic column typically includes a medium (i.e., a packing material) to facilitate separation of chemical moieties in space and time. The medium may include very small particles, which may have a bonded surface that interacts with the various chemical moieties to facilitate separation of the analytes of interest. One suitable bonded surface is a hydrophobic bonded surface such as an alkyl bonded surface. Alkyl bonded surfaces may include $C_4$, $C_8$, or $C_{18}$ bonded alkyl groups. In addition, monolithic and other phases known in the state of the art may be used as well. The chromatographic column includes an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used sequentially or as a two-dimensional (2D) chromatography system wherein a test sample may be applied to a first column at the inlet port, eluted with a solvent or solvent mixture onto a second column, and eluted with a solvent or solvent mixture from the second column to the outlet port. Different solvent modes may be selected for eluting the analytes. For example, liquid chromatography may be performed using a gradient mode, an isocratic mode, or a polytyptic (i.e. mixed) mode.

Figure 2:
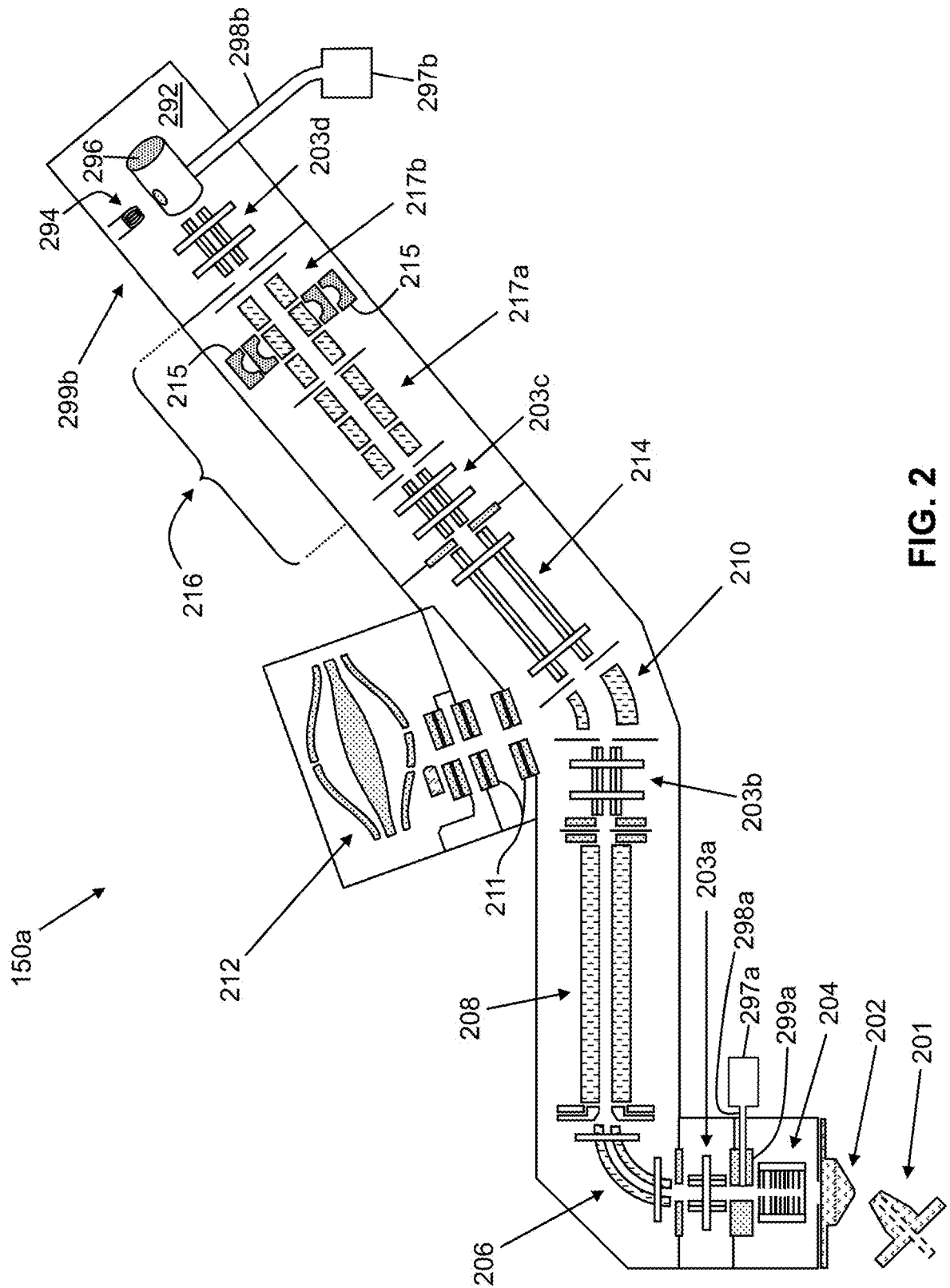
FIG. 2 is a schematic representation of an exemplary mass spectrometer suitable for employment in conjunction with methods according to the present teachings, the mass spectrometer comprising a hybrid system comprising a quadrupole mass filter, a dual-pressure quadrupole ion trap mass analyzer and an electrostatic trap mass analyzer.

FIG. 2 is a schematic depiction of an exemplary mass spectrometer 150a which may be employed as the mass spectrometer 150 of FIG. 1. The mass spectrometer illustrated in FIG. 2 is a hybrid mass spectrometer, comprising more than one type of mass analyzer. Specifically, the mass spectrometer 150a includes an ion trap mass analyzer 216 as well as an Orbitrap™ analyzer, which is a type of electrostatic trap mass analyzer. Since, as will be described below, various analysis methods in accordance with the present teachings employ multiple mass analysis data acquisitions, a hybrid mass spectrometer system can be advantageously employed to improve duty cycles by using two or more analyzers simultaneously. The Orbitrap™ mass analyzer 212 employs image charge detection, in which ions are detected indirectly by detection of an image current induced on an electrode by the motion of ions within an ion trap.

In operation of the mass spectrometer 150a, an electrospay ion source 201 provides ions of a sample to be analyzed to an aperture of a skimmer 202, at which the ions enter into a first vacuum chamber. After entry, the ions are captured and focused into a tight beam by a stacked-ring ion guide 204. A first ion optical transfer component 203a transfers the beam into downstream high-vacuum regions of the mass spectrometer. Most remaining neutral molecules and undesirable high-velocity ion clusters, such as solvated ions, are separated from the ion beam by a curved beam guide 206. The neutral molecules and ion clusters follow a straight-line path whereas the ions of interest are caused to bend around a ninety-degree turn by a drag field, thereby producing the separation.

A quadrupole mass filter 208 of the mass spectrometer 150a is used in its conventional sense as a tunable mass filter so as to pass ions only within a selected narrow m/z range. A subsequent ion optical transfer component 203b delivers the filtered ions to a curved quadrupole ion trap ("C-trap") component 210. The C-trap 210 is able to transfer ions along a pathway between the quadrupole mass filter 208 and the ion trap mass analyzer 216. The C-trap 210 also has the capability to temporarily collect and store a population of ions and then deliver the ions, as a pulse or packet, into the Orbitrap™ mass analyzer 212. The transfer of packets of ions is controlled by the application of electrical potential differences between the C-trap 210 and a set of injection electrodes 211 disposed between the C-trap 210 and the Orbitrap™ mass analyzer 212. The curvature of the C-trap is designed such that the population of ions is spatially focused so as to match the angular acceptance of an entrance aperture of the Orbitrap™ mass analyzer 212.

Multipole ion guide 214 and optical transfer component 203b serve to guide ions between the C-trap 210 and the ion trap mass analyzer 216. The multipole ion guide 214 provides temporary ion storage capability such that ions produced in a first processing step of an analysis method can be later retrieved for processing in a subsequent step. The multipole ion guide 214 can also serve as a fragmentation cell. Various gate electrodes along the pathway between the C-trap 210 and the ion trap mass analyzer 216 are controllable such that ions may be transferred in either direction, depending upon the sequence of ion processing steps required in any particular analysis method.

The ion trap mass analyzer 216 is a dual-pressure linear ion trap (i.e., a two-dimensional trap) comprising a high-pressure linear trap cell 217a and a low-pressure linear trap cell 217b, the two cells being positioned adjacent to one another separated by a plate lens having a small aperture that permits ion transfer between the two cells and that presents a pumping restriction and allows different pressures to be maintained in the two traps. The environment of the high-pressure cell 217a favors ion cooling, ion fragmentation by either collision-induced dissociation or electron transfer dissociation or ion-ion reactions such as proton-transfer reactions. The environment of the low-pressure cell 217b favors analytical scanning with high resolving power and mass accuracy. The low-pressure cell includes a dual-dynode ion detector 215.

The use of either a step of electron transfer dissociation or proton transfer reaction within a mass analysis method requires the capability of causing controlled ion-ion reaction within a mass spectrometer. Ion-ion reactions, in turn, require the capabilities of generating reagent ions and of causing the reagent ions to mix with sample ions. The mass spectrometer 150a, as depicted in FIG. 2, illustrates two alternative reagent-ion sources, a first reagent-ion source 299a disposed between the stacked-ring ion guide 204 and the curved beam guide 206 and a second reagent-ion source 299b disposed at the opposite end of the instrument, adjacent to the low-pressure cell 217b of the linear ion trap mass analyzer 216. Generally, any particular system will only include one reagent ion source at most. However, two different reagent ion sources are depicted and discussed here for illustrative purposes. Although the following discussion is directed to reagent ion sources for PTR, similar discussion may apply to ETD reagent ion sources.

A first possible reagent ion source 299a may be located between the stacked ring ion guide 204 and the curved beam guide 206. The reagent ion source 299a comprises a glow discharge cell comprising a pair of electrodes (anode and cathode) that are exposed to a reagent gas conduit 298a that delivers the reagent gas from a reagent liquid (or solid) reservoir 297a having a heater that volatilizes the reagent compound. When a high voltage is applied across the electrodes, glow discharge is initiated which ionizes the reagent flowing between the electrodes. Reagent anions from the glow discharge source are introduced into the ion optics path ahead of the quadrupole mass filter 208 within which they may be m/z selected. The reagent ions may then be accumulated in the multipole ion guide 214, and subsequently transferred into the high pressure cell 217b of the dual-pressure linear ion trap 216 within which they are made available for the PTR reaction. The reaction products may be directly transferred to the low pressure cell 217a or to the Orbitrap™ mass analyzer 212 for m/z analysis.

A possible alternative reagent ion source 299a may be located adjacent to the low pressure linear trap cell 217b where it may comprise an additional high-vacuum chamber 292 from which reagent ions may be directed into the high pressure cell 217b through an aperture in between chamber 292 and the high-pressure cell. In operation, gaseous reagent compound is supplied from a reagent liquid (or solid) reservoir 297b having a heater that volatilizes the reagent compound and is directed through a reagent gas conduit 298b that delivers the reagent gas into a partially confined ion generation volume 296. In operation, thermionic electrons supplied from an electrically heated filament 294 are directed into the ion generation volume 296 with a certain pre-determined energy by application of an electrical potential between the filament 294 and an accelerator electrode (not shown). The supplied energetic electrons cause ionization of the reagent gas so as to generate reagent ions. The reagent ions may then be guided into the high pressure cell 217b by ion optical transfer component 203a under the operation of gate electrodes (not shown).

Figure 3A:
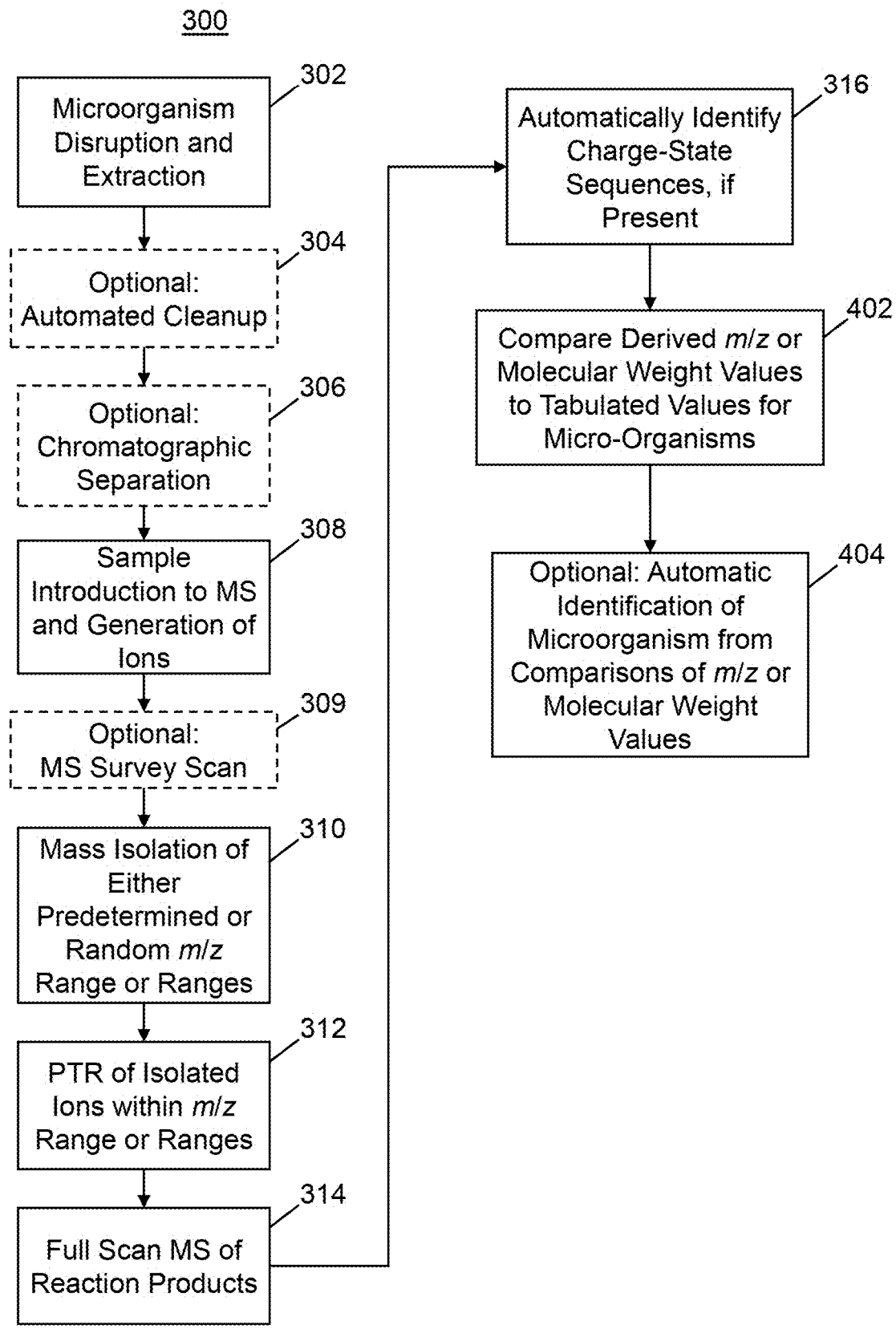
FIG. 3A is a flow diagram of a first method in accordance with the present teachings.

Exemplary methods in accordance with the present teachings are schematically illustrated in the flow diagrams shown in FIGS. 3A-3F. FIG. 3A schematically illustrates a first such exemplary method, method 300, for monitoring for the presence of and, optionally, quantifying, certain specific targeted analyte proteins or peptides in a sample of microorganisms. The initial steps 302, 304 and 306 of the method 300 are the steps of microorganism disruption (e.g., lysis) and extraction, solid-phase clean-up, or size-exclusion chromatography and chromatographic separation, respectively, as described above. In some experimental situations, the extracted sample may be directly infused into a mass spectrometer in the subsequent sample introduction step 308; thus, the steps 304 and 306 are shown by dashed lines as being optional. Samples may also be prepared using offline approaches including dialysis, or other techniques known in the state of the art. However, in many other experimental situations, the steps 304 and 306 are useful so as to at least partially purify the sample prior to mass-spectral analysis.

When an analysis must be completed according to time constraints, as in some clinical applications, the required time for the analysis may be shortened by employing either a SPE step 304, a time-compressed chromatography step as described in U.S. Pat. No. 5,175,430 to inventor Enke, or the method of "Fast Partial Chromatographic Separation" (FPCS) in the chromatography step 306 as described in international (PCT) patent application publication WO 2013/166169 A1. Generally, in performing FPCS, a crude extract of microbial cells containing a complex mixture of various organic and inorganic analytes (small organic molecules, proteins and their naturally occurring fragments, lipids, nucleic acids, polysaccharides, lipoproteins, etc.) is loaded on a chromatographic column and subjected to chromatography. However, instead of allowing a gradient to elute each analyte separately (ideally, one analyte per chromatographic peak), the gradient is intentionally accelerated to the extent that substantially no chromatographic peaks obtained for example approximately eight minutes or less, and preferably five minutes or less instead of a much longer run time that would be required to obtain a baseline separation. In the FPCS separation, many analytes are intentionally co-eluted from the column at any given time according to their properties and the type of chromatography (reverse phase, HILIC, etc.) used. Partial or incomplete separation may be also accomplished by other methods known to one skilled in the art, including but not limited to the use of mobile phase solvents and/or modifiers that reduce retention of compounds on the column, selection of stationary phase media that reduce retention of compounds on the column (including particle size, pore size, etc.), operation of the chromatographic system at higher flow rate, operation of the chromatographic system at an elevated temperature, or selection of a different chromatographic separation mode (i.e., reversed-phase, size exclusion, etc.). The FPCS technique yields few or, possibly, no resolved chromatographic peaks across the whole gradient. Thus, substantially the only relevant information derived from a chromatogram is the time of elution from the column. Each mass spectrum that is recorded represents a "subset" of co-eluting analytes that is then ionized, separated in the mass analyzer and detected.

In step 308 (FIG. 3A), the sample is introduced into a mass spectrometer. The sample may be provided as the eluate material that emerges from an SPE cartridge, a chromatography apparatus or, alternatively, by direct infusion of the eluate solution. Upon being provided to the mass spectrometer, the sample compounds are ionized (step 308) by an electrospray ionization source of the mass spectrometer. These electrospray-generated ions are herein referred to as "first-generation" ions. At this juncture, a full or segmented $MS^1$ scan may optionally be performed (step 309) in order to identify the protein-rich regions in m/z space. (Note that in this document, the term "scan" may be taken to generally refer to a mass spectrum when used as a noun or, alternatively, to the acquisition of a mass spectrum, when used as a verb). In a preferred embodiment, the $MS^1$ scan can be obtained over the full mass range of the mass spectrometer instrument in order to be able to subsequently choose, in data-dependent or independent fashion, an information-rich portion of the spectrum for isolation (step 310). However, in the case of a targeted analysis, the $MS^1$ scan may be unnecessary and execution of the method 300 may proceed directly to step 310, in which a subset of the ions is then isolated for further reaction and analysis. When targeted analysis is employed, the isolation performed in step 310 may be such that ions within a certain pre-determined m/z range or possibly multiple pre-determined m/z ranges are retained for the subsequent reaction and analysis whereas ions outside the pre-determined m/z range or ranges are discarded. The pre-determined m/z range or ranges are chosen so as to correspond to preferably known m/z ratios of targeted analyte proteins or peptides whose presence or quantity is detected or monitored in the execution of the method.

Generally, the isolation of step 310 may be performed, in known fashion, by introducing the ions from the ion source into an ion trap—such as a three-dimensional ion trap, a curved ion trap (sometimes referred to as a "C-Trap") a single segment linear ion trap, multiple segmented linear ion trap, multipole ion guide or quadrupole mass filter—and then resonantly ejecting the ions whose m/z ratios are outside of the desired range by applying a supplemental AC voltage across pairs of electrodes of the ion trap or applying the appropriate RF/DC voltage ratios to isolate the ion population of interest. In some embodiments, the frequency of the supplemental voltage may be swept through various frequencies such that the ions are ejected in sequence according to their m/z ratios. In such cases, the ions may be detected as they are ejected so as to generate a mass spectrum of the original set of ions. However, since a mass spectrum may not be required at this stage, the supplemental AC voltage may be alternatively applied as a combination of superimposed frequencies that are chosen so as to cause essentially simultaneous ejection of the ions whose m/z ratios are outside of the desired range. In some embodiments, the combination of superimposed frequencies may be provided with multiple segments of missing frequencies (i.e., "notches") such that ions comprising two or more non-contiguous m/z ratio ranges are simultaneously isolated within the trap. Each one of the non-contiguous m/z ratio ranges may correspond to a preferably known m/z ratio of a respective unique targeted analyte protein or peptide. The applied RF/DC voltage ratios of a quadrupole mass filter may also be used to isolate the defined or targeted mass ranges of interest. Particular m/z ranges of the first-generation ions are selected by a single or series of fixed RF/DC voltage ratios in order to select the appropriate mass isolation windows. The instrumental configuration employed in this case may be a hybrid mass spectrometer instrument comprising a quadrupole, a C-trap, an Orbitrap™ mass analyzer, and a high energy collision cell (HCD) where the isolated ion population can be stored in either the C-trap or HCD cell for PTR experiments. The isolated population or populations of the first-generation ions are herein referred to as "precursor" ions, because these ions will be subjected to subsequent ion-ion reactions or to fragmentation.

In a preferred embodiment, the isolation of the precursor ion population may be performed in a first segment of a segmented linear ion trap. After isolation of the desired ion population, the multiply-charged protein ion population may be advantageously moved to another segment of the linear ion trap. These steps can be repeated multiple times for isolated defined ranges of precursor ions prior to the PTR process.

Next, anions are generated using either a rhenium-based filament with chemical ionization or glow discharge ionization source from a suitable high electron affinity based gaseous reagent. Chemical ionization can be performed using nitrogen, methane, isobutane, or other known gases in the state of the art. The anion reagent may be a gas at room temperature or may be a liquid with sufficient vapor pressure to produce an excess of anions which will drive the PTR process under pseudo-first order reaction conditions. The anions are then transferred from the source region to the segmented linear trap whereby the specific anion reagent is mass isolated using supplemental AC voltages as described above. The anion source can be in-line with the electrospray source or mounted on the opposite end of the segmented linear ion trap. Alternatively, a quadrupole mass filter can perform the anion isolation as well with the subsequent PTR process occurring in the C-trap or HCD cell of the instrument.

In step 312 of the method 300 (FIG. 3A), the ions which were mass-isolated in step 310 (i.e., "precursor" ions) are subjected to a proton transfer reaction in which a reagent anion species is reacted for a specified time period with the sample precursor ions in the ion trap so as to extract protons from the precursor cations. In one embodiment, the multiply-charged precursor ion population and the singly-charged anion population are reacted by adjusting the DC voltage offsets of the segmented linear ion trap so as to store both the multiply-charged positive ions with the singly charged anions to facilitate the PTR process. The reagent anions are chosen such that, in this instance, the reagent anions behave as a Brønsted-Lowry base and such that the precursor ions behave as one or more Brønsted-Lowry acids. The reagent anions are formed by separate ionization of a suitable reagent gas/liquid with sufficient vapor pressure, that includes but is not limited to sulfur hexafluoride, perfluoro-1,3-dimethyl cyclohexane, perfluorodecalin, and perfluoroperhydrophenanthrene. After allowing the reaction to proceed for a specified time, a supplementary AC voltage is applied across electrodes of the ion trap so as to eject the reagent anions, thereby leaving product ions and, possibly, some residual precursor ions within the ion trap.

In the opposite polarity experiment, multiply-charged anions derived from proteins or other biomolecules can also be reacted with singly-charged cations. A variety of sources can be employed to generate singly-charged cations including electron, chemical, and electrospray ionization processes. These reactions follow the same reaction kinetics described previously. Typical reagent cations have included pyridine, benzo(f)quinolone, and the noble gases argon and xenon. In addition, multiply-charged proteins of opposite polarity have also been reacted as well as the multiply-charged anions from nucleic acids with the multiply-charged cations of proteins.

In step 314 of the method 300 (FIG. 3A), a mass spectrum is obtained of the product ions from the PTR process retained in the ion trap over a full range of m/z ratios of interest. The mass spectrum may be obtained, in known fashion, by detecting ions that are sequentially ejected from the 3D or linear ion trap in order of their m/z ratios. Alternatively, the ions may be directed to a different mass analyzer of the mass spectrometer, such as a Time-of-Flight (TOF) mass analyzer or an Orbitrap™-type of electrostatic trap mass analyzer, to be analyzed with greater accuracy or mass resolution then may be available by sequential scanning of the ion trap. Further, by directing the product ions to a separate analyzer, the ion trap may be re-filled with a new sample of precursor ions while the mass analysis is being performed. If the accurate mass analyzer is of a type—such as an FT-ICR mass analyzer or an Orbitrap™ mass analyzer—that detects image currents produced by cyclic ion motion within an ion trap, then the PTR reaction steps may advantageously reduce collision cross sections of targeted protein or polypeptide molecules such that these molecules remain stable in the trap for a sufficient length of time to generate high-quality mass spectra. Also, the PTR product ions will have less kinetic energy when leaving the high pressure C-trap region upon their transfer to the Orbitrap™ mass analyzer. Due to the PTR process, the resulting product ion population will be fully desolvated which will improve the quality of the resulting mass spectrum.

In step 316 of the method 300, the mass spectrum generated by the mass analysis performed in step 314 is automatically examined so as to recognize one or more individual series of related m/z ratios, wherein each m/z ratio of a series represents a respective different charge state—that is, a different degree of protonation—of a single intact protein or polypeptide molecule. For example, see FIG. 9C which depicts two different series of lines, represented by the envelope 905 and the envelope 906, respectively. After ionization as well as subsequent to the PTR reaction, each protein or polypeptide molecule, M, of mass $m_p$, is represented as at least one (and likely several different) protein or polypeptide cation species. Each such cation species of a related series formed from the particular molecule, M, may be represented by the chemical formula $(M+zH)^{z+}$, where the integer, z, is the number of protons adducted to the original molecule or is the number of protons remaining on the protein after the PTR step. In this example, considering only monoisotopic ions, the mass-to-charge ratio, $(m/z)_{ion}$, is thus given by:

$$(m/z)_{ion} \approx (m_p + z \times 1.007)/z \approx (m_p + z)/z \approx m_p/z \qquad \text{(Eq. 1)}$$

where the final approximation results from the fact that $m_p \gg z$. Accordingly, such series of ion species representing only different states of protonation may be readily recognized by using automated software in real time to determine the monoisotopic ions. Once such series have been recognized, the molecular mass, $m_p$, of the parent protein or polypeptide molecule may be discerned in real time. Similar approaches can be applied to larger molecular weight molecules using average or monoisotopic mass as well.

The m/z values generated by the PTR process or, alternatively, the molecular weights obtained from the PTR product ions can then be searched against a database containing individual pathogen standards that contain the observed m/z values or molecular weights from known reference standards/patient samples. By matching these m/z values or molecular weights from a database containing individual referenced pathogens, a small subset of possible pathogen identifications is obtained. The subset can be limited by determining a particular mass accuracy, weighting the intensities of the individual peak, and/or by weighting the molecular weight values by mass in a given scoring system. This is illustrated in step 402 of FIG. 3A. In certain cases, the m/z or molecular weight matches may provide a direct match to a particular pathogen identification. However, in all probability, the m/z molecular weight information will reduce substantially the number of possible pathogen identifications that can be unequivocally identified using tandem mass spectrometry. This process was originally described for use in conjunction with the steps 302, 304, 306, and 308-310 in international (PCT) patent application publication WO 2013/166169 A1. Additionally, Bayesian, logistic regression, or decision tree based methods can be employed to further refine the identification of the pathogen. In a preferred embodiment, this m/z or molecular weight search is performed in real time during data acquisition (i.e., as the sample is being analyzed). Alternatively, the search may be performed post-acquisition (i.e., after the sample has been analyzed) as well. The comparison of a small number of m/z values or molecular weights (3-10) of proteins to a reference database will generally be sufficient to significantly reduce the candidate number of pathogen identifications to five or less. This is illustrated is step 404 of FIG. 3A.

Figure 3B:
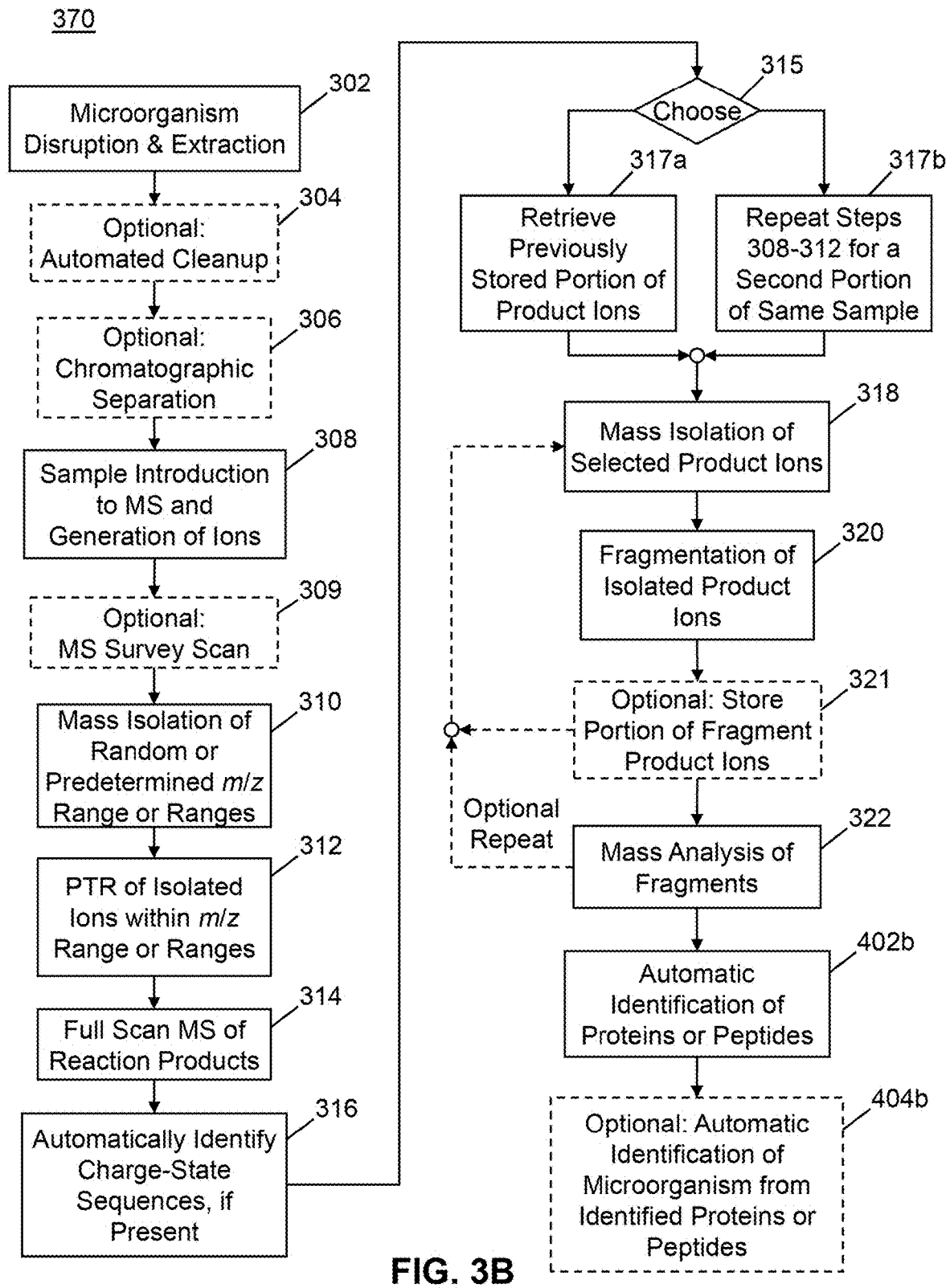
FIG. 3B is a flow diagram of an alternative method in accordance with the present teachings.

FIG. 3B schematically illustrates a flow diagram of a second exemplary method, method 370, in accordance with the present teachings. The steps 302-314 of the method 370 (FIG. 3B) are identical to the similarly numbered steps of the method 300 (FIG. 3A) and thus the description of these steps is not repeated here. The method 370 differs from the method 300 only with regard to the steps following the generation of a mass spectrum in step 314. According to the earlier-described method 300, this mass spectrum of PTR product ions is assumed to be sufficient to detect or quantify proteins and polypeptides of interest. However, in many cases, it may be necessary to perform tandem mass spectrometry (sometimes referred to as MS/MS or MS″) after the generation of PTR reaction products in order to resolve remaining ambiguities in the recognition of specific protein or polypeptide molecules. In such situations, the PTR reaction products may be considered to comprise a first generation of reaction products which are then fragmented to form a second generation of product ions. The combination of a specific m/z ratio of a first-generation reaction product with one or more specific m/z ratios of fragment ions may, in many cases, allow identification of a specific protein or polypeptide molecule associated with a given pathogen. In many instances the protein identified with a specific pathogen may also be found in other similar pathogens. In order to correctly identify a single pathogen, method 370 (specifically tandem mass spectrometry) may need to be performed on as many proteins that are present in a given PTR fraction, or multiple PTR fractions of the same sample.

Accordingly, steps 318-322 of method 370 (FIG. 3B) represent the application of the techniques of tandem mass spectrometry or selected reaction monitoring (SRM) as applied to the ions formed by PTR. If the particular employed mass spectrometry system permits, a portion of the PTR product ions may have already been stored (immediately after step 312) in an ion storage apparatus of the mass spectrometer system. In such cases, the branching step 315 causes execution of step 317a, in which the previously stored ions are retrieved for further processing. Otherwise, if the prior batch of PTR product ions was exhausted by the mass analysis step (step 314), then, in accordance with the alternative step 317b, the steps 308-312 may need to be re-executed in order to generate a new batch of such PTR product ions.

In step 318 of the method 370, certain of the PTR reaction-product ions (i.e., the first-generation product ions) within a particular m/z range or particular m/z ranges are mass isolated by ejecting ions whose m/z ratios are not within the range or ranges of interest. The isolated ions are subsequently fragmented in step 320. The particular chosen range or ranges will generally be responsive to the details of a particular identified charge-state sequence identified an immediately prior execution of step 316 and the choice will generally be made automatically by computer. Thus, the choice of a particular m/z range or ranges for isolation and fragmentation is an example of so-called "data-dependent analysis" (or "data-dependent acquisition", etc.).

Figure 7A:
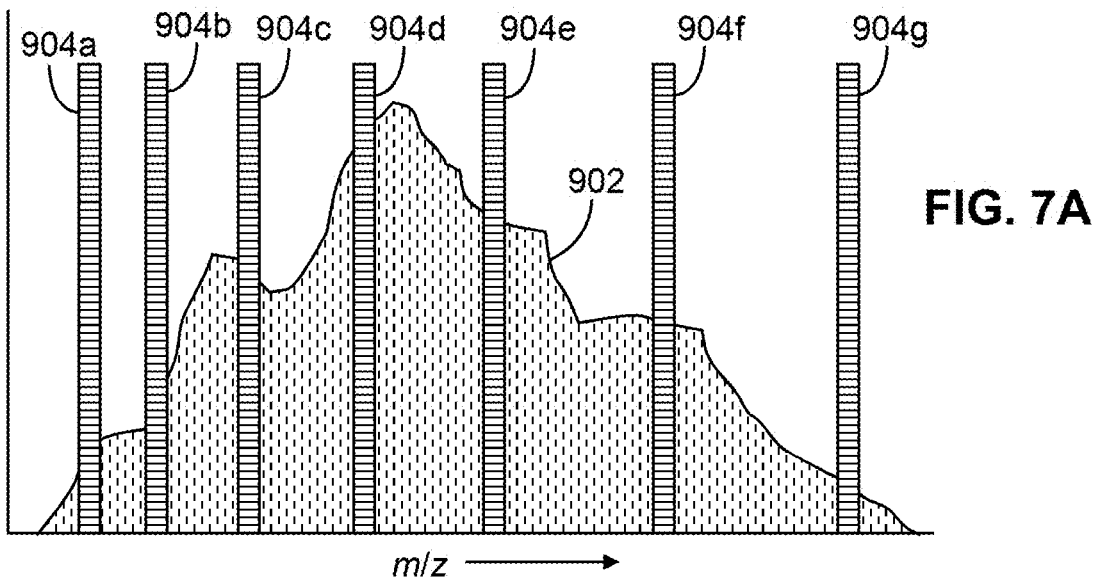
FIG. 7A is a schematic depiction of a method, in accordance with the present teachings, of improved-efficiency PTR conversion of ions of a selected analyte to an assemblage of PTR product ions by simultaneous isolation and reaction of multiple m/z ranges of electrospray-produced first-generation precursor ions.
Figure 7B:
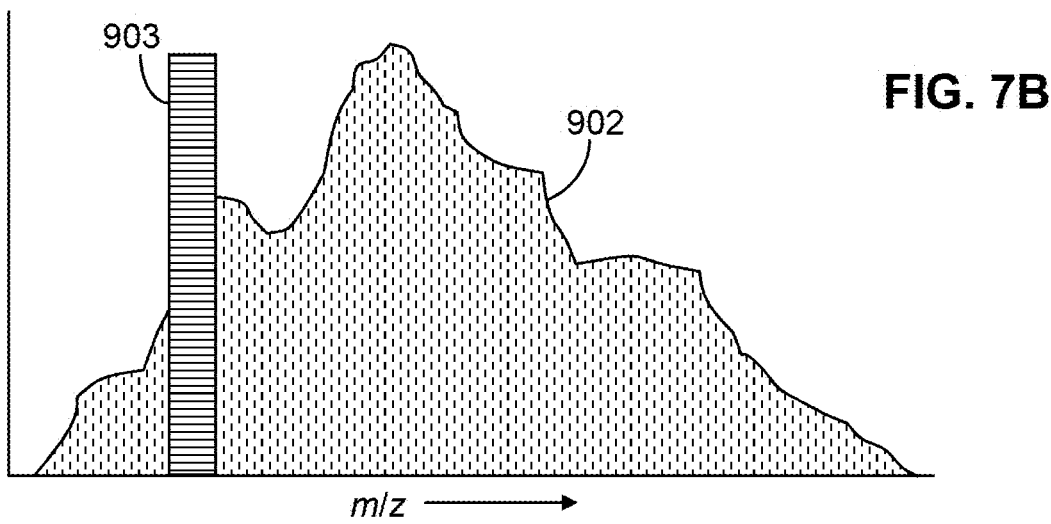
FIG. 7B is a schematic diagram of isolation of a first randomly-chosen range of electrospray-produced first-generation precursor ions for PTR reaction, as may be employed in an initial step of a method of improved-efficiency PTR conversion of ions.
Figure 7C:
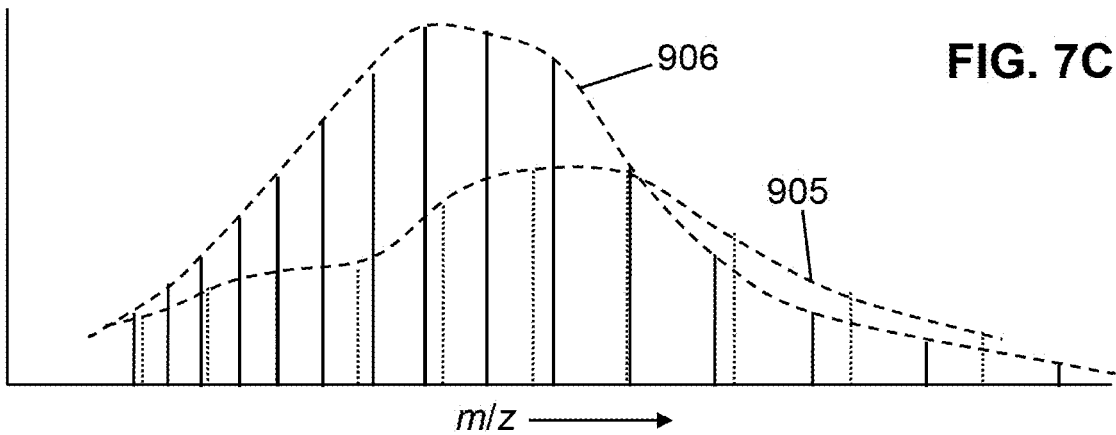
FIG. 7C is a schematic depiction of recognition of two charge-state sequences of PTR product ions corresponding to different analyte molecules, as may be employed as an intermediate step of a method of improved-efficiency PTR conversion of ions.

In most conventional MS/MS analyses, involving low-mass molecules of a few hundred to a few thousand Daltons, data-dependent fragmentation comprises choosing the "top P number of the most abundant precursors" for tandem mass analysis based on the information of a preceding $MS^1$ data acquisition, where the number P is either a constant or perhaps a variable input by a user. It has been found that this conventional form of data-dependent analysis does not perform well when used in the analysis of multicomponent samples of biopolymer analytes. For example, FIG. 7C illustrates two charge state distributions, denoted by the envelope 905 and the envelope 906, respectively. In this example, each envelope corresponds to a different respective analyte molecule species. Thus, the sets of lines encompassed by envelopes 905 and 906 may be referred to as "molecular-species-correlative charge-state distributions". Considering the lines (individual m/z values) in FIG. 7C to represent precursor ions, then if P=10, the conventional data-dependent fragmentation technique would choose the ten leftmost solid vertical lines under the envelope 906 for fragmentation. Using the conventional technique, none of the dotted lines corresponding to envelope 905 would be chosen. The conventional procedure would thus yield redundant information relating to the molecule species corresponding to envelope 906 and no information relating to the molecule species corresponding to envelope 905.

To overcome the shortcomings of conventional data-dependent fragmentation when applied to high-molecular-weight molecules, the inventors have developed the herein-used novel "top P unique analyte-specific clusters" data-dependent technique so as to replace, for application to high-molecular-weight molecules, the previous "top P number of the most abundant precursors" logic. Each molecular-species-correlative charge-state distribution is a set of related mass spectral lines (m/z values) which are interpreted, according to the novel "top P unique analyte-specific clusters" logic, to all be generated from a single unique molecule. Each molecular-species-correlative charge-state distribution groups together various charge states and isotopic clusters that are indicated to have been generated from a single molecule, prior to ionization. However, the molecular-species-correlative distribution excludes adducts, which are removed prior to data analysis. According to the novel method, fragmentation is performed only on one (or possibly more) selected representatives of a given molecular-species-correlative charge state distribution envelope thereby avoiding the redundancy noted above associated with the conventional data-dependent fragmentation method. According to the novel "top P unique analyte-specific clusters" logic, after a representative m/z ratio (or ratios) has been chosen for a first molecular-species-correlative charge-state distribution, any further fragmentation is directed to a representative m/z ratio of the next determined molecular-species-correlative charge-state distribution, and so on.

As previously described, the isolation performed in step 318 of the method 370 may be accomplished by applying a supplemental AC voltage across pairs of electrodes of an ion trap such that ions having m/z ratios that are not within the range or ranges of interest are ejected from the trap while those ions having m/z ratios that are within the range or ranges are retained within the trap. In some instances, the ion trap used for mass isolation may be identical to the mass analyzer used to conduct the full-scan mass analysis in step 314.

The supplemental AC voltage applied to the ion trap used for mass isolation may comprise a summation of superimposed frequencies such that ions within two or more non-contiguous m/z ranges are simultaneously isolated. In the subsequent step 320, the mass-isolated first-generation product ions are fragmented by a suitable ion fragmentation technique, such as collision induced dissociation (CID). The fragmentation may be accomplished by transferring the first-generation product ions (product ions formed by PTR of original precursor ions), in known fashion, to a dedicated fragmentation cell within which the transferred ions are fragmented so as to generate fragment ions, these fragment ions comprising a second generation of reaction products. Optionally, a portion of the fragment product ions may be stored for possible future additional fragmentation in optional step 321.

In step 322 of the method 370 (FIG. 3B), the fragments generated in step 320 are mass analyzed by a mass analyzer of the mass spectrometer. If the second-generation product ions are produced within a fragmentation cell that is specifically dedicated for the purpose of fragmentation, the ions must be first transferred to the mass analyzer prior to the execution of step 322. An ion trap mass analyzer may be employed to analyze the second-generation product ions in step 322, in which case the mass analyzer employed for step 322 may be identical to the mass analyzer employed to conduct the full-scan mass analysis of step 314. Alternatively, an accurate-mass analyzer capable of measuring mass-to-charge ratios to an accuracy of 10 ppm or better—such as an FT-ICR mass analyzer, a time-of-flight (TOF) mass analyzer or an Orbitrap™-type of electrostatic trap mass analyzer—may be employed for step 322.

As is known, the correlation between the m/z value of a certain selected ion species subjected to fragmentation and the m/z value (or values) of one or more fragment ion species produced by the fragmentation may be sufficient to automatically determine (in step 402b) the chemical identity of the selected ion species. In this case, the selected ion species is a PTR reaction-product species generated in step 312 that is mass-isolated in step 318. The identification of a small number (i.e., 3-10) of such proteins will generally be sufficient to uniquely identify a microorganism species (optional step 404b). However, a single stage of fragmentation may be insufficient for performing a chemical species identification. In such instances, the second generation product ions may be further fragmented so as to form a next generation of product ions, indicated by the optional repeat (indicated with dashed lines) from step 322 back to step 318 in which a selected subset of the fragment product ions are isolated, according to their m/z values, and the so-isolated fragment ions are further fragmented. More generally, a subset of the $n^{th}$ generation of product ions may be selected for further fragmentation by any suitable ion fragmentation method such as, but not limited to, collision-induced fragmentation, higher-energy collisional dissociation, electron transfer dissociation, electron capture dissociation, negative electron transfer dissociation, electron-detachment dissociation, in-source fragmentation, surface-induced dissociation, or photodissociation, whereby an $(n+1)^{th}$ generation of product ions is formed. The results of the mass analysis step 322 may form the basis of an automated decision as to whether or not each additional fragmentation is required and, if so, which m/z values correspond to the ion species to be fragmented.

The method 300 diagramed in FIG. 3A, which was discussed above, provides a relatively simple and straightforward method of sample analysis that may be applicable for samples of relatively low complexity as, for example, when highly-resolved chromatographic separation (step 306) has been performed prior to introduction of a chromatographic fraction into a mass spectrometer (step 308). However, the simple method 300 may not be appropriate for more complex samples and the analysis of such samples may present a number of challenges. Firstly, the proteins present in a complex mixture have a wide range of molecular weights. Secondly, the large number of charge states that result from the presence of a large number of lysine, arginine, histidine residues may result in multiple overlapping sets of peaks, each set of peak corresponding to a different chemical species. Thirdly, if the mass analysis (step 314) is of sufficiently high resolution, the presence of resolved peaks of an isotopic distribution for any given charge state can confound most data processing algorithms. Finally, the distribution of available ions among multiple charge states and, possibly, among multiple isotopic states necessarily reduces the signal intensity of any resolved peak in the mass analysis.

Figure 3C:
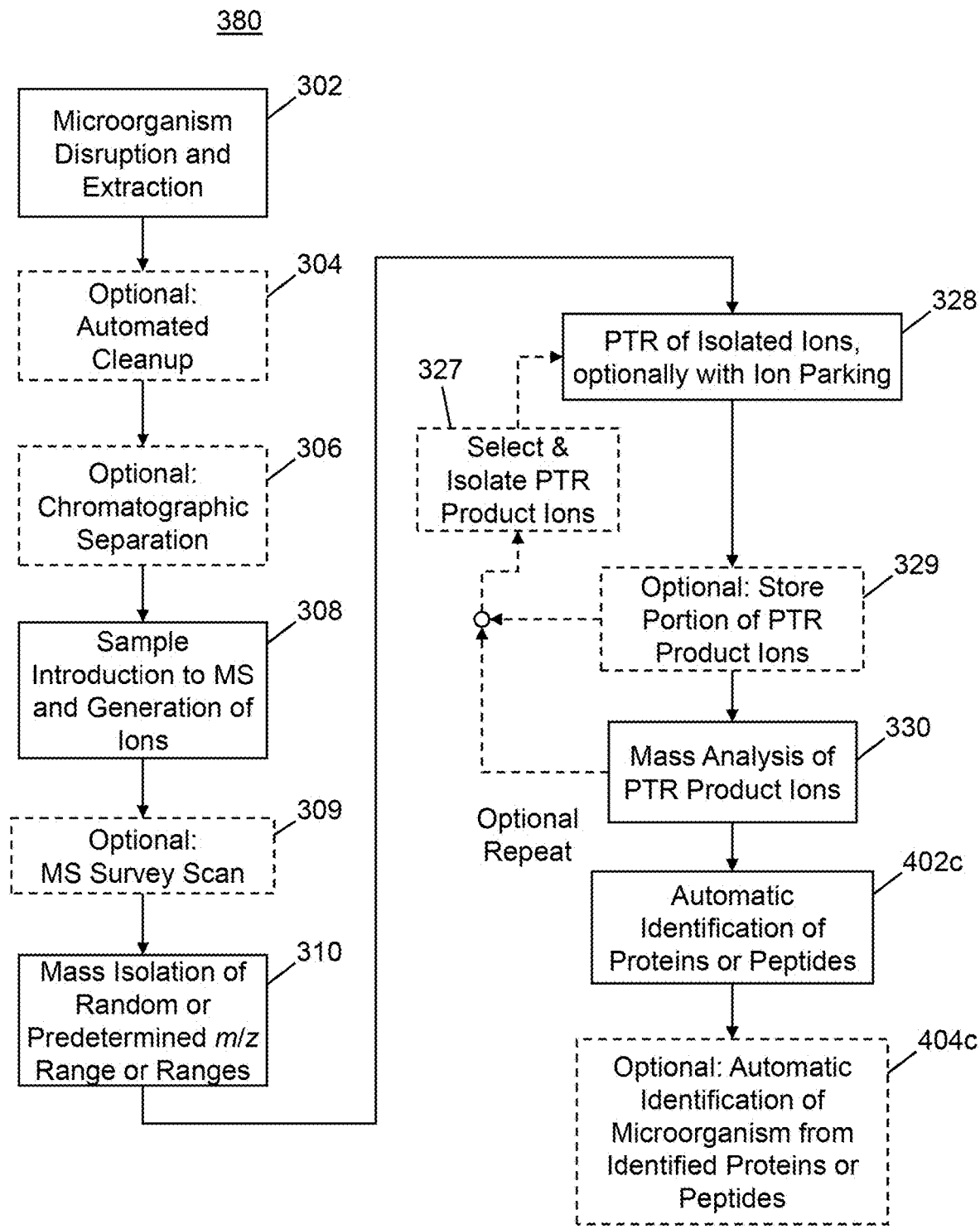
FIG. 3C is a flow diagram of another alternative method in accordance with the present teachings.

In order to address the above-noted challenges in the analysis of complex samples, the method 380, for which a schematic flow diagram is illustrated in FIG. 3C, provides the opportunity for conducting multiple PTR stages. Under the earlier-described method 300, it is assumed that the mass spectrum obtained (in step 314) of the first-generation PTR reaction products (generated in step 312) exhibits sufficient improvement in signal-to-noise ratio and sufficient reduction in isobaric interferences such that charge-state sequences may be recognized and that proteins or polypeptides may be identified. If such improvement in mass spectral quality remains inadequate for such purposes after a first PTR reaction event, then the additional refinement steps 327-330 of the method 380 (FIG. 3C) may be performed. Further, one or more of the PTR stages may utilize the known technique of "ion parking" in order to simplify the charge state distribution, as noted in the previous paragraph. Ion parking is a technique whereby specific selected ion/ion reactions within an ion trap are inhibited. In practice, a resonance excitation waveform is applied across electrode pairs of an ion trap, ion guide or other ion storage device in an amplitude that is insufficient to cause ion ejection but sufficient to increase the velocities of ions having selected m/z values. This excitation process increases the relative velocity between the excited ions (cations, for purposes of the present discussion) and reagent anions and it is believed that this relative velocity increase causes a reduction in the rates of reaction between the excited cations and reagent anions.

During the PTR process, the rate of reaction between cations and reagent anions varies as the square of the charge number of the various cations with the anion charge on the reagent ions equal to −1. Thus, in the absence of ion parking, the PTR process leads to a rapid reduction in the number of highly charged cations. Over the course of the reaction, the distribution of charge states of cations derived from a single molecular species, M (a protein or polypeptide molecule having mass $m_p$), shifts towards lower charge states. The population of each ion species having an intermediate charge state will first increase as the more-highly-charged precursor ions lose protons and then decrease as each respective species loses more protons then it gains from the diminishing quantity of more-highly-charged cations. The ultimate result, if the PTR reaction is allowed to proceed to completion, is complete neutralization of all such cations and total loss of all mass spectrometric signal.

When the ion parking technique is applied during the PTR reaction, then the charge reduction process is essentially stopped at the charge state, $z_1$, corresponding to the particular mass-to-charge ratio (for example, $m_p/z_1$) of the ions which are resonantly excited by the applied AC waveform. Those precursor cations derived from the molecular species, M, with initial charge states, z, such that $z>z_1$ will lose protons until their charge states are reduced to $z_1$, after which further reaction and proton loss will be inhibitied. Those precursor cations derived from the molecular species, M, with initial charge states, z, such that $z<z_1$ will be completely neutralized. Accordingly, after PTR reaction with ion parking, a significant portion of the original protonated molecular ions (i.e., precursor ions) of molecule M will be represented, in a mass spectrum, by the single ionic species having charge state, $z_1$. This "concentration" of the molecule species, M, into a single charge state can advantageously amplify the mass-spectrometric signal associated with that species, thereby improving signal-to-noise ratio and reducing the lower limit of detection and, optionally, the lower limit of quantification of the species. Further, many isotopic variants of ions generated from molecule species, M, will have m/z values outside of the range of values corresponding to the applied AC resonant excitation waveform. Such isotopic variants will be neutralized so as to not interfere with the mass spectrometric identification of ions of interest. Other isotopic variants comprise m/z values that are within the range of values corresponding to the applied AC resonant excitation waveform. The isotopic distribution pattern of such isotopically variant ions will be greatly simplified relative to the isotopic distribution observed in the original precursor ions because they will mostly relate to the single charge state, $z_1$ of ions generated from molecule, M.

Returning to the discussion of the method 380 outlined in FIG. 3C, it is to be noted that the steps 302-310 of the method 380 are identical to the similarly numbered steps of the method 300 (FIG. 3A) and are not re-described here. Subsequently, in step 328, precursor ions are subjected to PTR, optionally as modified by the ion parking technique. As previously noted, step 328 is executed by applying a supplemental AC excitation waveform across a pair of electrodes of an ion trap within which sample-derived cations are reacted with reagent anions for a predetermined time period. As described above, the employment of this "ion parking" procedure will concentrate the distribution of ions derived from any particular protein or polypeptide into a particular restricted range of m/z values. This will generally restrict the ions derived from any particular protein or polypeptide into a particular charge state, thereby simplifying a resulting mass spectrum and increasing the intensity of any mass spectral peaks corresponding to the particular protein or polypeptide. The particular range of m/z values into which the ions are restricted may comprise ions of different respective charge states derived from different respective molecular species. In some embodiments, the applied AC waveform used to effect the ion parking may comprise a summation of waveforms of different respective frequencies such that the summed waveform causes the PTR reaction to yield a final population of PTR product ions corresponding to two or more non-contiguous m/z ranges.

In the subsequent step 330, the population of PTR product ions produced in step 328 is mass analyzed. Prior to this mass analysis, a portion of the PTR product ions may be stored (step 329) in preparation for possible subsequent PTR reaction. Depending upon the results of the mass analysis of the PTR product ions, an automatic decision may be made to subject the PTR product ions to such further PTR reaction, as indicated by the dashed line optional pathways shown in FIG. 3C. The decision may also be made, based on the results of the mass analysis, to only subject a selected subset of the PTR product ions to subsequent PTR reaction. In such cases, step 327 is executed. If the mass analyzer employed in step 330 is of a type that detects image currents produced by cyclic ion motion within an ion trap or other ion storage device—such as an FT-ICR mass analyzer or an Orbitrap™ mass analyzer—then the PTR reaction steps may advantageously reduce collision profiles of targeted protein or polypeptide molecules such that these molecules remain stable in the trap for a sufficient length of time to generate high-quality mass spectra. After a sufficient number of PTR reaction steps, the chemical identity of the protein or polypeptide may then be rapidly discerned (in step 402c) by matching to databases of known molecular masses. The identification of a small number of (3-10) of proteins will generally be sufficient to uniquely identify a microorganism species (optional step 404c). Identification can also be accomplished via the use of classifiers applied to the PTR data as discussed previously that includes but is not limited to Bayesian, logistic regression or decision tree based approaches.

Figure 3D:
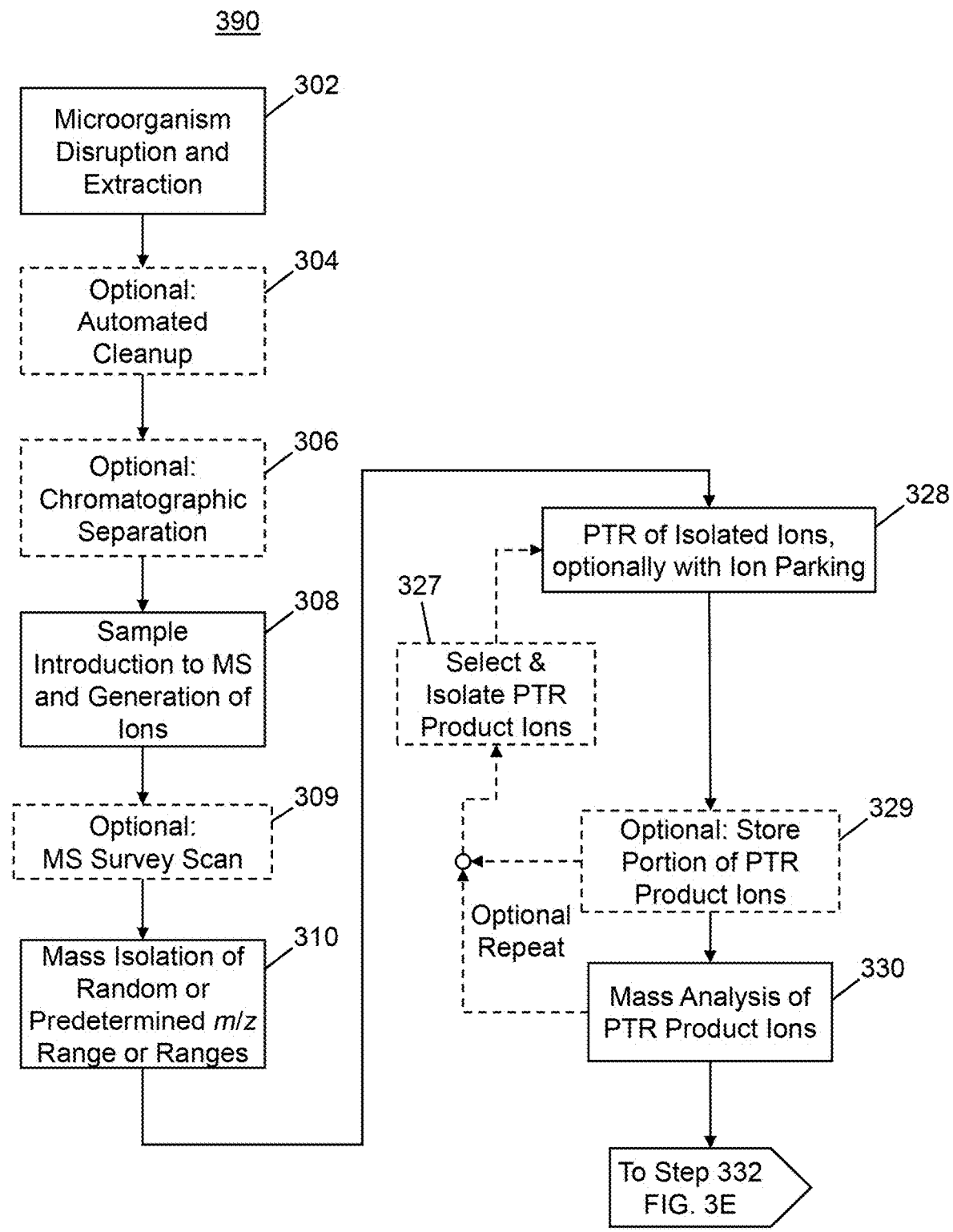
FIG. 3D and FIG. 3E illustrate a flow diagram of yet another alternative method in accordance with the present teachings.
Figure 3E:
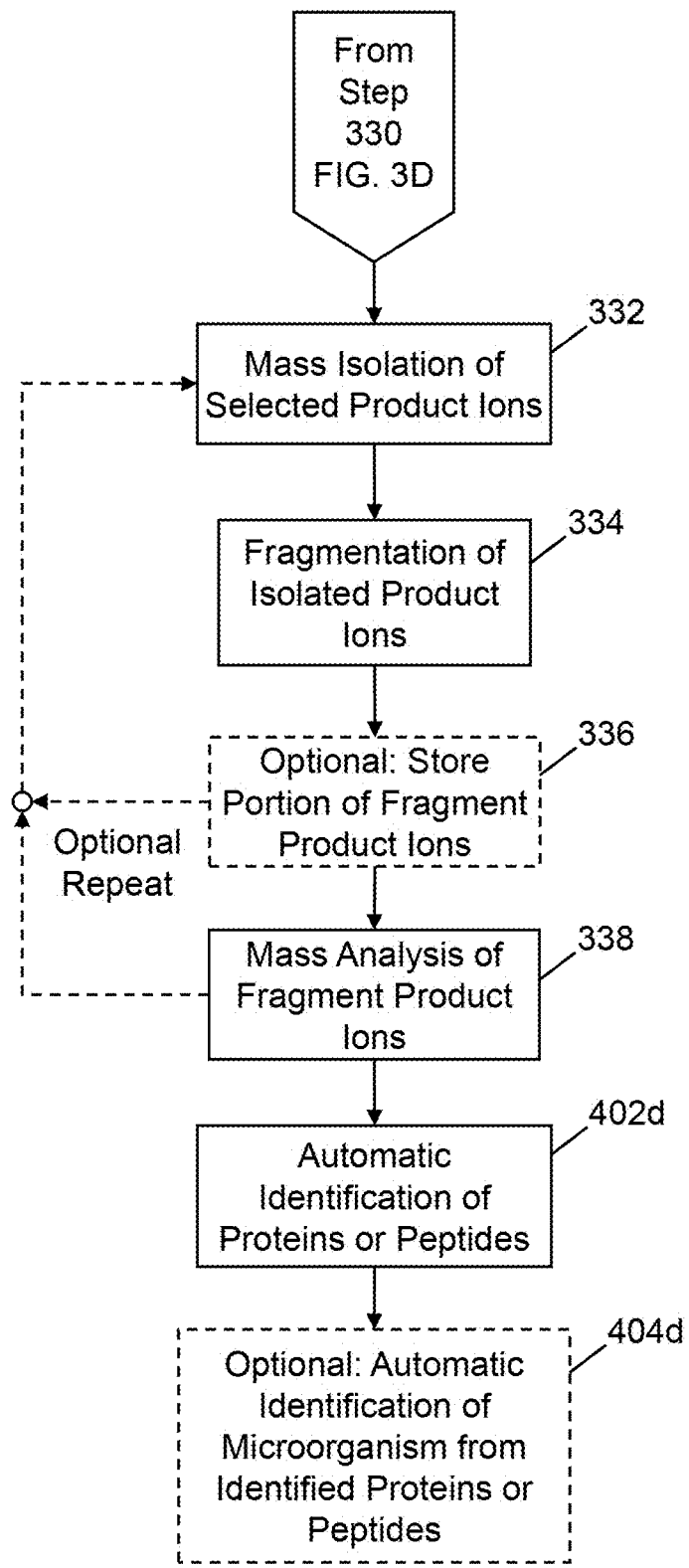

FIGS. 3D-3E illustrate, in flow diagram form, another method, method 390, in accordance with the present teachings. The steps 302-330 of the method 390 are shown in FIG. 3D and are identical to the previously-discussed similarly-numbered steps of the method 380 (FIG. 3C); thus, these steps are not re-described here. Instead of proceeding to the identification step 402d directly from step 330 (as in the method 380 of FIG. 3C), execution of the method 390 (FIGS. 3D-3E) proceeds from step 330 to a mass selection and isolation step 332. In step 332, a subset of the PTR product ions—generated by one or more applications of the PTR procedure—are isolated according to selected m/z ratios. Decisions regarding the specific m/z ratios to be isolated during this step may be automatically performed based on the mass spectrometric results obtained in step 330. The steps 332-338 illustrated in FIG. 3E represent an ion fragmentation procedure which may be iterated so as to produce multiple generations of fragmentation product ions. These steps 332-338 are similar to the steps 318-322 of the method 370 illustrated in FIG. 3B and are thus not discussed in detail.

After execution of the fragmentation and mass analysis steps, the peptide identification step 402d of the method 390 (FIG. 3E) is executed. Whereas the identification step 402a of the method 300 (FIG. 3A) makes use only of the m/z ratios (or molecular weights) of ion species comprising protonated or multiply-protonated analyte molecules, the identification step 402d of the method 390 also takes into account the m/z ratios of the fragments—possibly of multiple generations—of these ion species. Thus, in the case of complex mixtures of proteins or polypeptides, a greater confidence may be associated with the results of the identifications made using the method 390. Control of the experiments may be performed in real time according to some embodiments by making use of real-time data deconvolution as noted above. The identification of a small number of (3-10) of proteins species in step 402d will generally be sufficient to uniquely identify a microorganism species in step 404d.

Figure 3F:
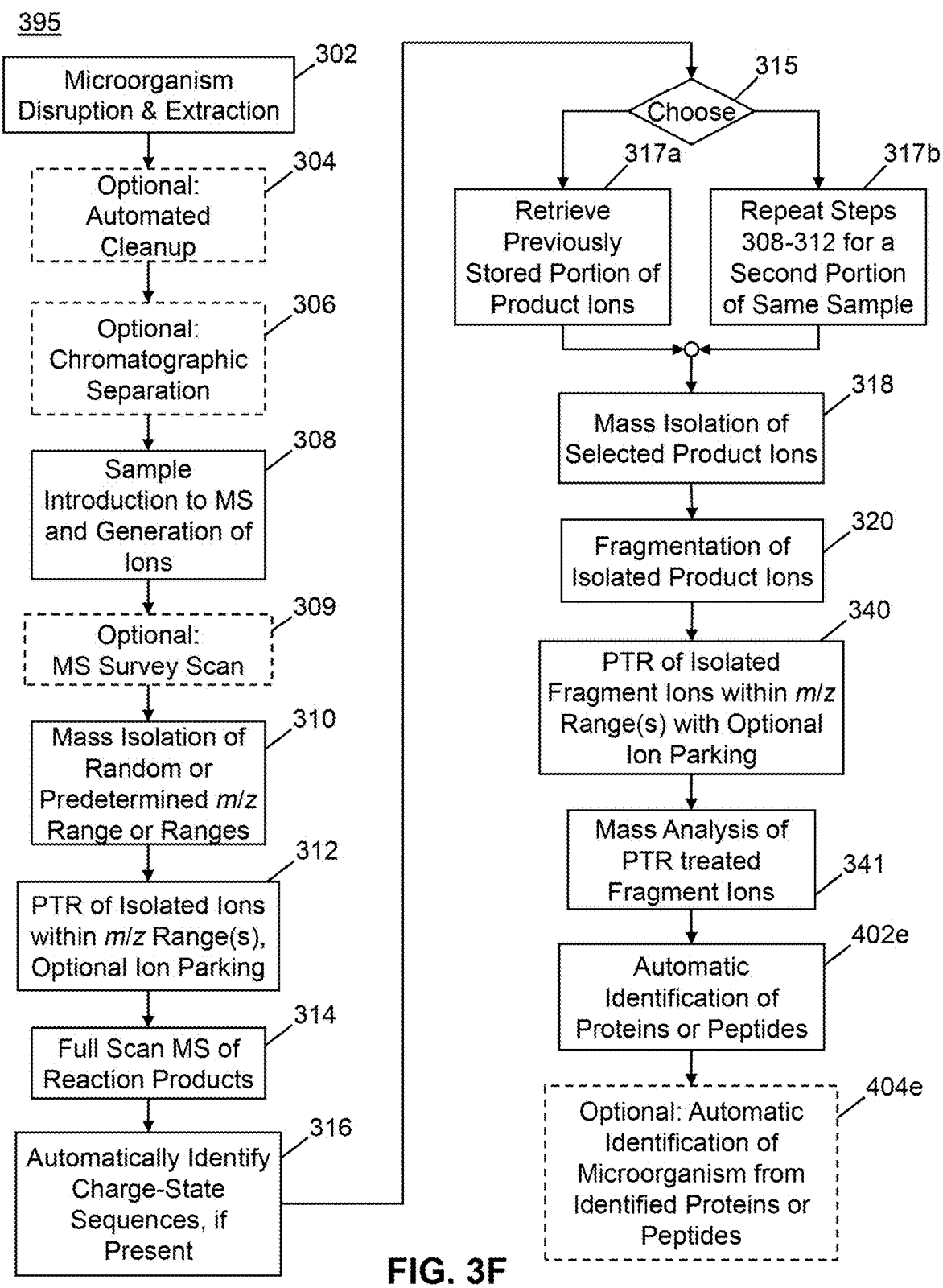
FIG. 3F is a flow diagram of still yet another alternative method in accordance with the present teachings.

FIG. 3F diagrammatically illustrates, in flow diagram form, another method, method 395, in accordance with the present teachings. Most of the steps in the method 395 (FIG. 3F) are similar to similarly numbered steps in the method 370 (FIG. 3B) and these steps are not re-described in detail. Similarly to the method 370, the method 395 includes a step (step 312) of subjecting original precursor ions to PTR charge reduction followed by steps (steps 318 and 320) of isolating selected PTR product ion species and subjecting the isolated ion species to fragmentation so as to form fragment product ion species. The method 395 differs from method 370 through the provision of an additional step, step 340, of subjecting the fragment ions to PTR charge reduction. Since the various PTR product ion species generated from the original precursor ions may be multiply-charged and may be distributed among species with various degrees of protonation, the fragment ions formed from them may themselves be distributed among multiple protonation states. The PTR charge reduction of the fragment ion species in step 340 can simplify the charge state distributions of the fragment ions prior to their mass analysis in step 341. Optionally, any of the PTR steps (step 312 and step 340) may employ ion parking.

Example A

Figure 4A:
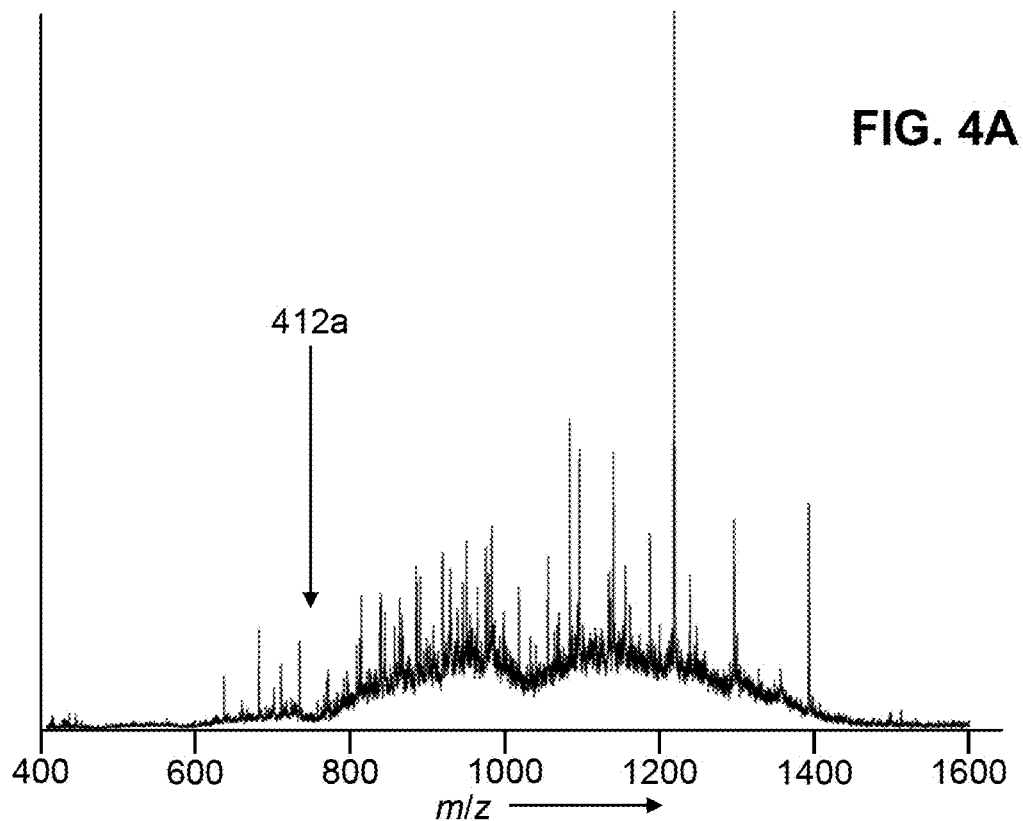
FIG. 4A is an ESI mass spectrum via direct infusion of a typical $E.\ coli$ extract.
Figure 4B:
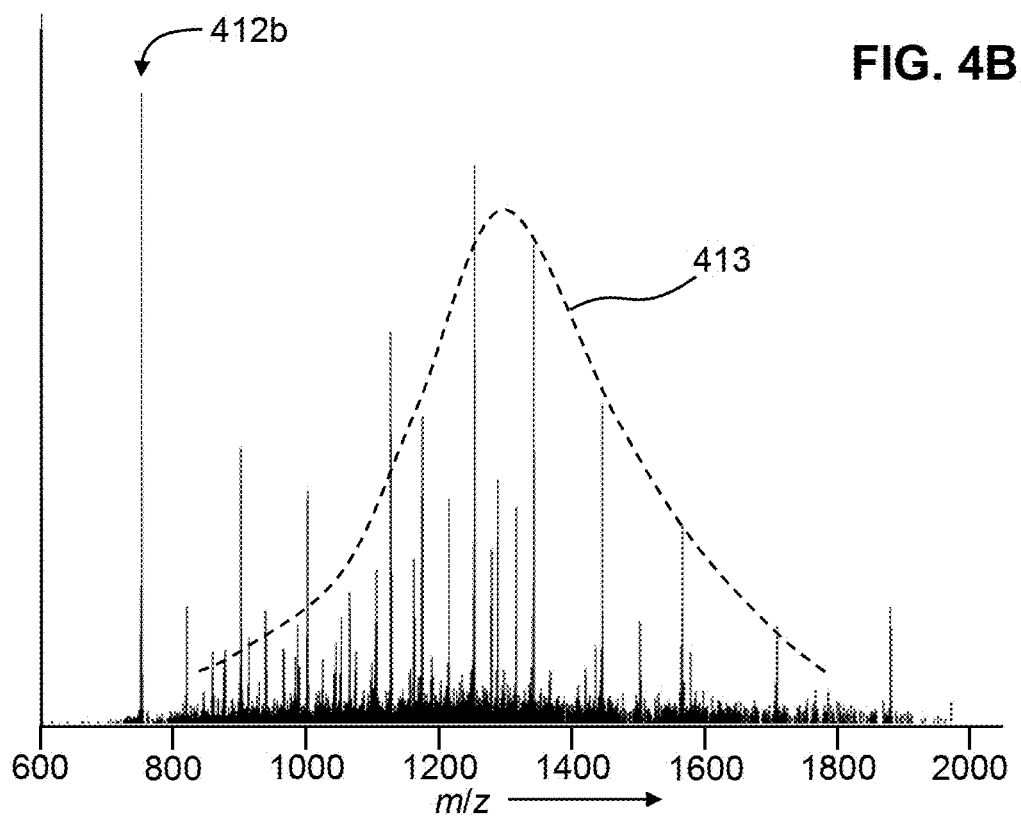
FIG. 4B is a PTR product-ion mass spectrum generated by isolating ions of the $E.\ coli$ extract of FIG. 4A within a 2 Th mass window centered at m/z=750 Th and reacting the isolated ions with PTR reagent anions.

FIGS. 4A and 4B provide an example of mass spectroscopic signal enhancement provided by a single PTR reaction step (e.g., as in the method 300 shown in FIG. 3A). In a first application (FIGS. 4A, 4B), an extract from the pathogen *E. coli* was analyzed via direct infusion; the mass spectrum of the first-generation electrospray-generated ions is shown in FIG. 4A. As expected, there are many proteins present that overlap at various m/z values leading to the presence of a broad spectral region between approximately m/z=780 and m/z=1420 within which many ions are detected but with very little usable information in terms of discernible protein charge state distributions. Next, an m/z "window" of the first-generation ions of width 2 Th and centered at m/z=750 was isolated and the resulting isolated ion population was subjected to PTR reaction. The m/z position 412a shown in FIG. 4A indicates the center position of the isolation window.

FIG. 4B shows a mass spectrum of the PTR reaction products of precursor ions of the *E. coli* extract. The PTR reactions were carried out with reagent anions derived from 3 ppm of sulfur hexafluoride ($SF_6$) in a nitrogen gas stream delivered to a glow discharge reagent ion source contained within the ion optics of a mass spectrometer of the same general configuration as illustrated in FIG. 2. As with most PTR product-ion spectra, the mass spectrum shown in FIG. 4B exhibits a relatively intense isolated peak at the position (indicated as position 412b) of the original first-generation-ion isolation window. Such peaks at the position of the isolation window generally indicate the presence of residual singly-charged first-generation ions—generally not of interest—that fortuitously occur at the position of the isolation. Other peaks in the spectrum of FIG. 4B represent product ions generated from the PTR reaction. These product ions generally comprise overlapping sets of related ions, each set corresponding to ions comprising a distribution of charge states from an original multiply-charged precursor ion within the original isolation window. One such potential charge-state distribution pattern is approximately indicated by the envelope 413. The results shown in FIGS. 4A and 4B show that the PTR reaction process generally significantly simplifies the spectrum and reduces background interference. Nonetheless, since many protein-derived or peptide-derived precursor ions may be present in the original isolation window, the charge-state distribution patterns may overlap. Mathematical decomposition (sometimes referred to as "deconvolution") may be required to recognize the individual patterns.

Example B

Figure 5A:
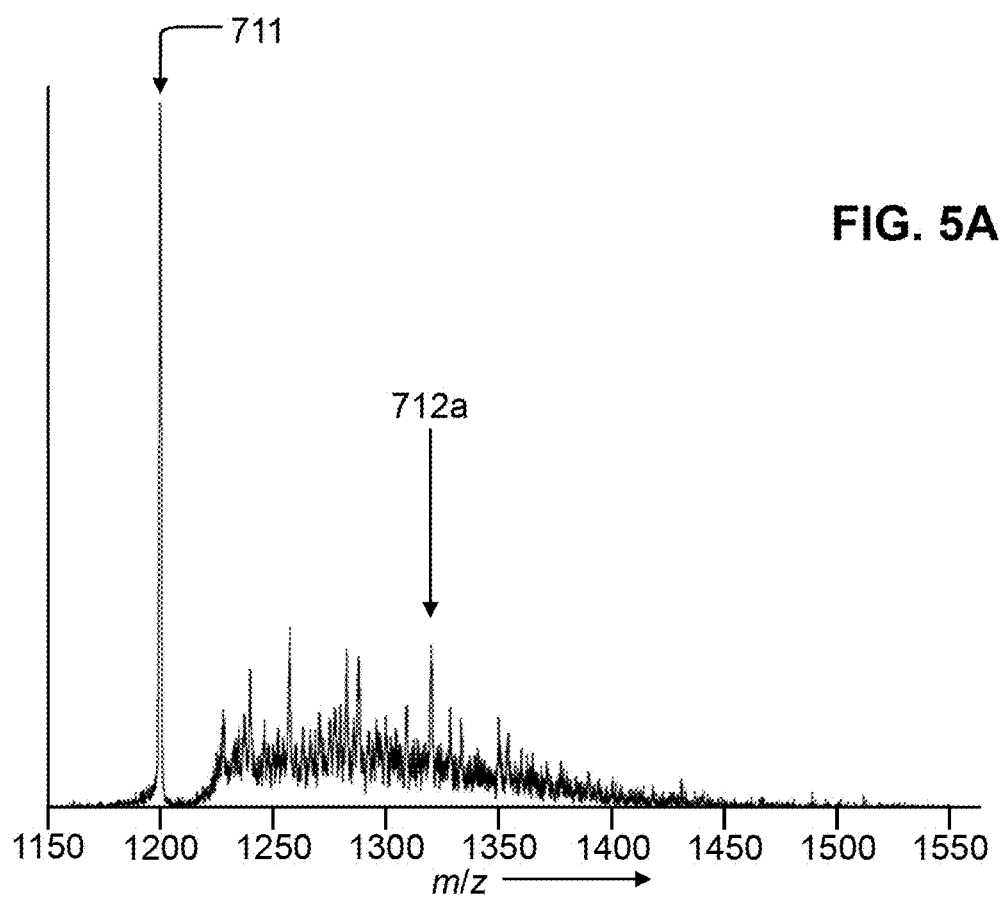
FIG. 5A is a mass spectrum of first-generation PTR product ions generated by isolating ions of an $E.\ coli$ extract within a mass window of width 5 Th centered at 1200 Th and reacting the isolated ions with PTR reagent anions.
Figure 5B:
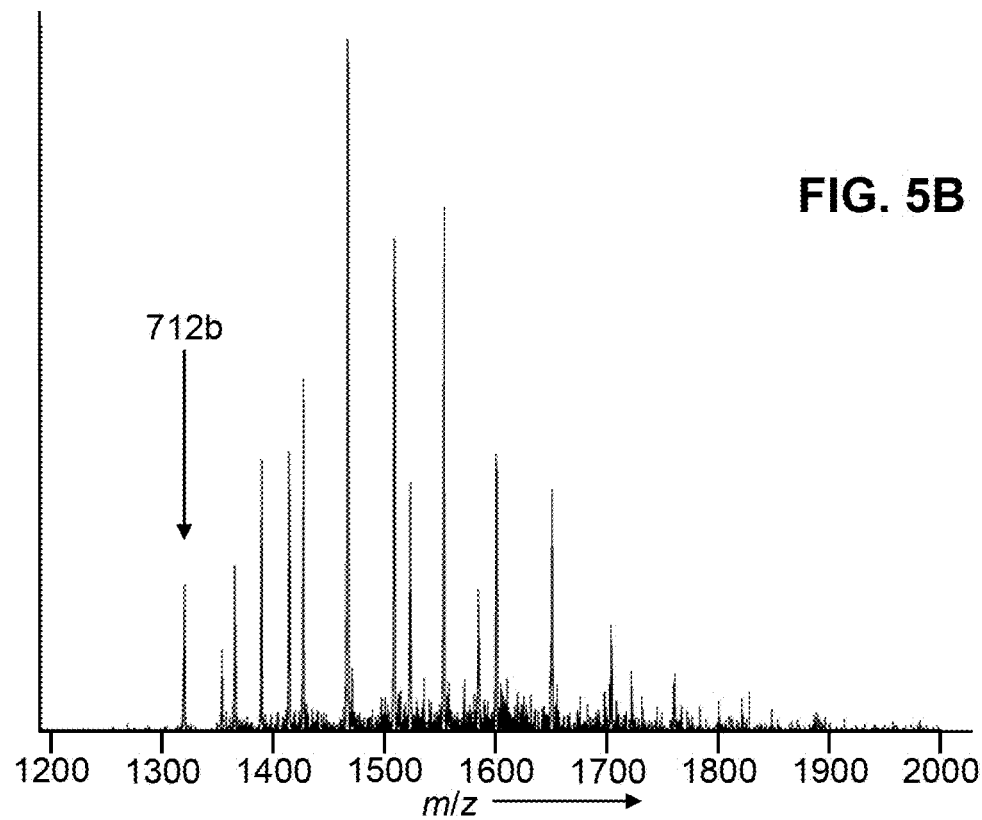
FIG. 5B is a mass spectrum of second-generation PTR product ions generated by isolating ions of the first-generation PTR product ions of FIG. 5A within a mass window of width 5 Th centered at 1320 Th and reacting the isolated first-generation product ions with PTR reagent anions a second time.

FIGS. 5A and 5B illustrate an example of analysis of an *E. Coli* extract that is performed by a procedure that includes two stages of PTR reaction (for example, see steps 327, 328, 329 and 330 of method 380 in FIG. 3C). FIG. 5A illustrates a PTR product ion spectrum generated isolated first-generation precursor ions from within a 5 Th mass window centered at m/z=1200, indicated by position 711 in FIG. 5A. In this instance, the initial PTR spectrum does not include peaks that are sufficiently well resolved to enable identification of any proteins in the sample. Therefore, a subset of the first-generation PTR product ions were isolated for a second stage of PTR from within a 5 Th mass window centered at m/z=1320, indicated by position 712a in FIG. 5A and position 712b in FIG. 5B. The second-generation PTR product ions, which occur at m/z ratios greater than 1320 in FIG. 5B show clear charge-state distribution patterns that may be successfully used for identification of proteins in the sample.

Figure 6A:
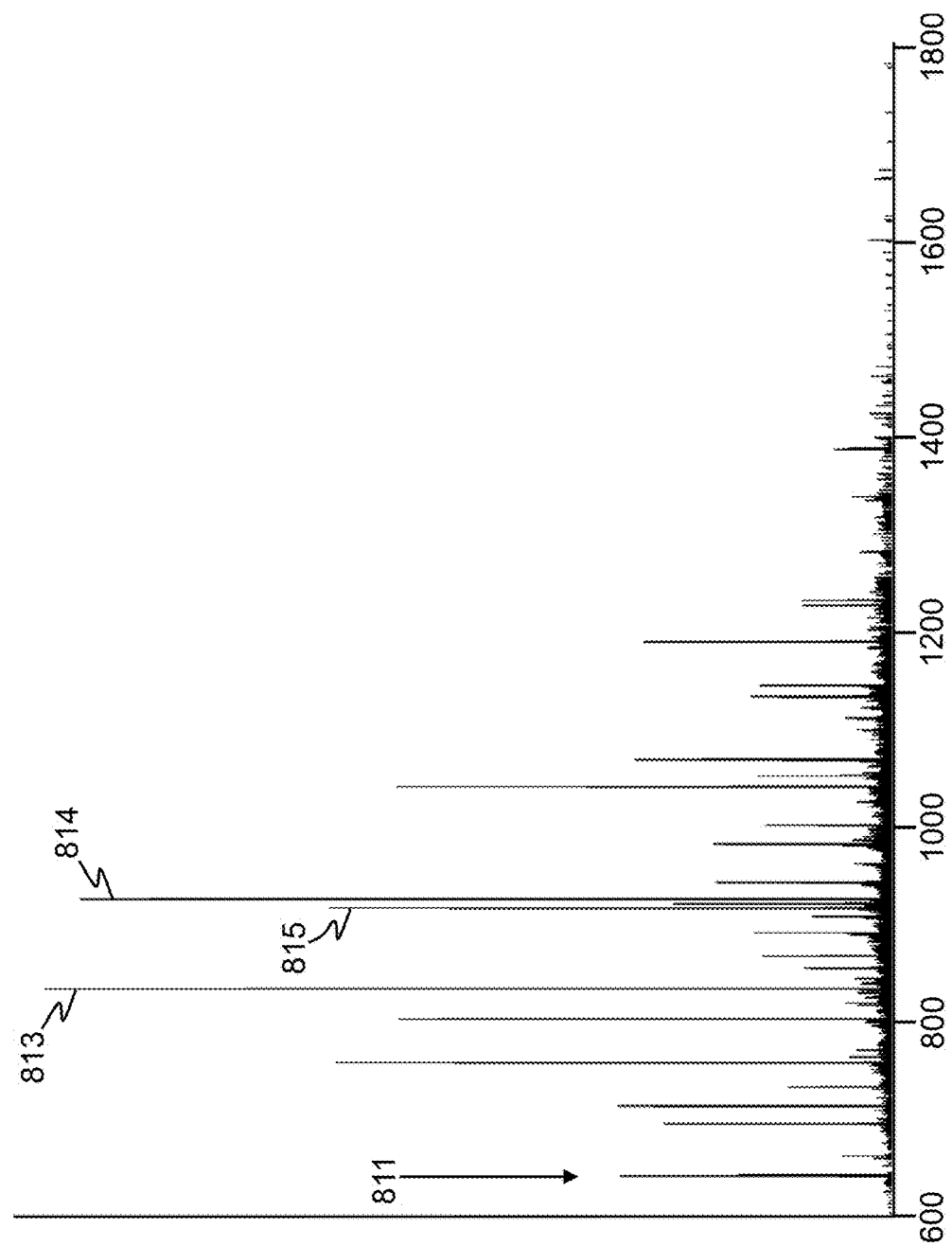
FIG. 6A is a mass spectrum of PTR product ions generated by isolating ions of an $E.\ coli$ extract within a mass window of width 5 Th centered at 640 Th and reacting the isolated ions with PTR reagent anions.
Figure 6B:
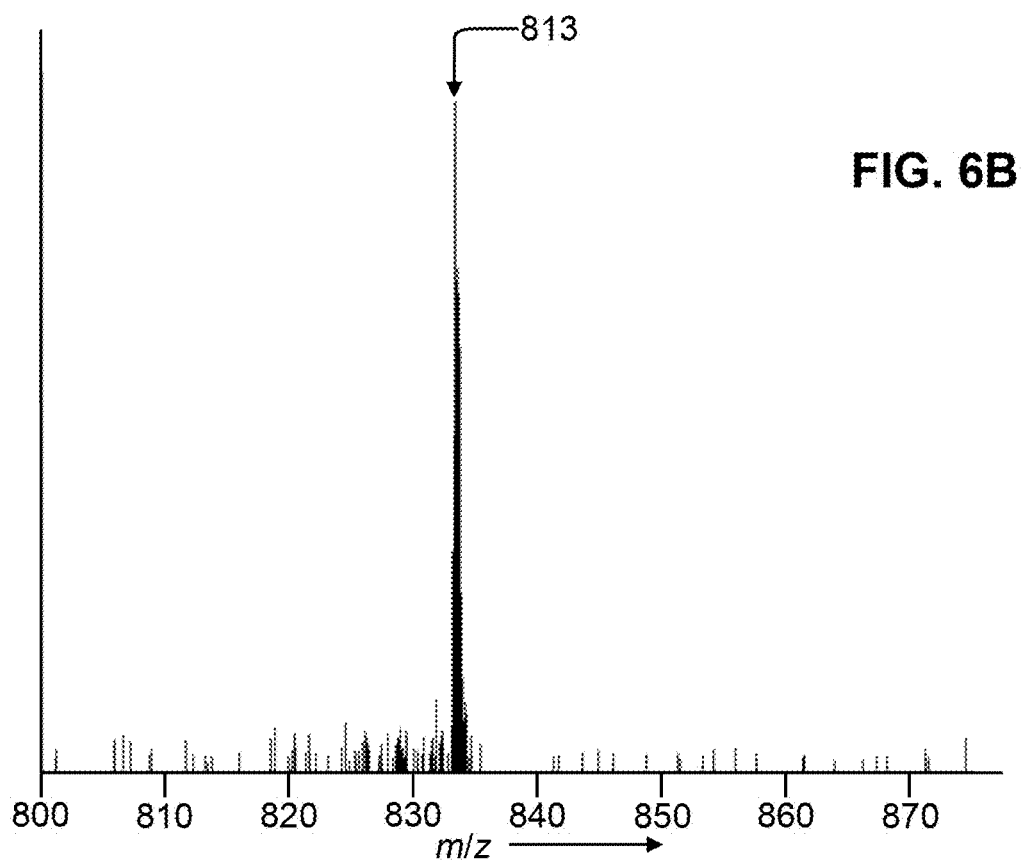
FIG. 6B is a mass spectrum of an isolated PTR product ion species selected from the product ion assemblage of FIG. 6A and having an m/z ratio of 833 Th.
Figure 6C:
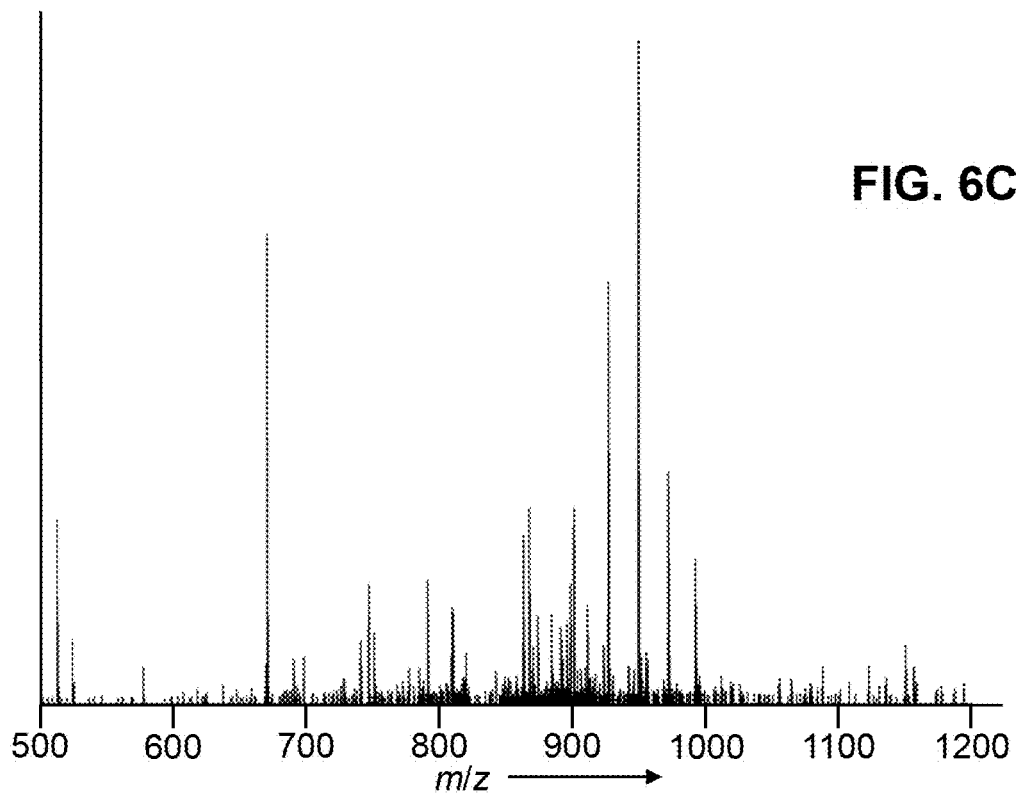
FIG. 6C is a mass spectrum of second-generation product ions generated by collision-induced dissociation (CID) of the isolated PTR product ion species of FIG. 6B.
Figure 6D:
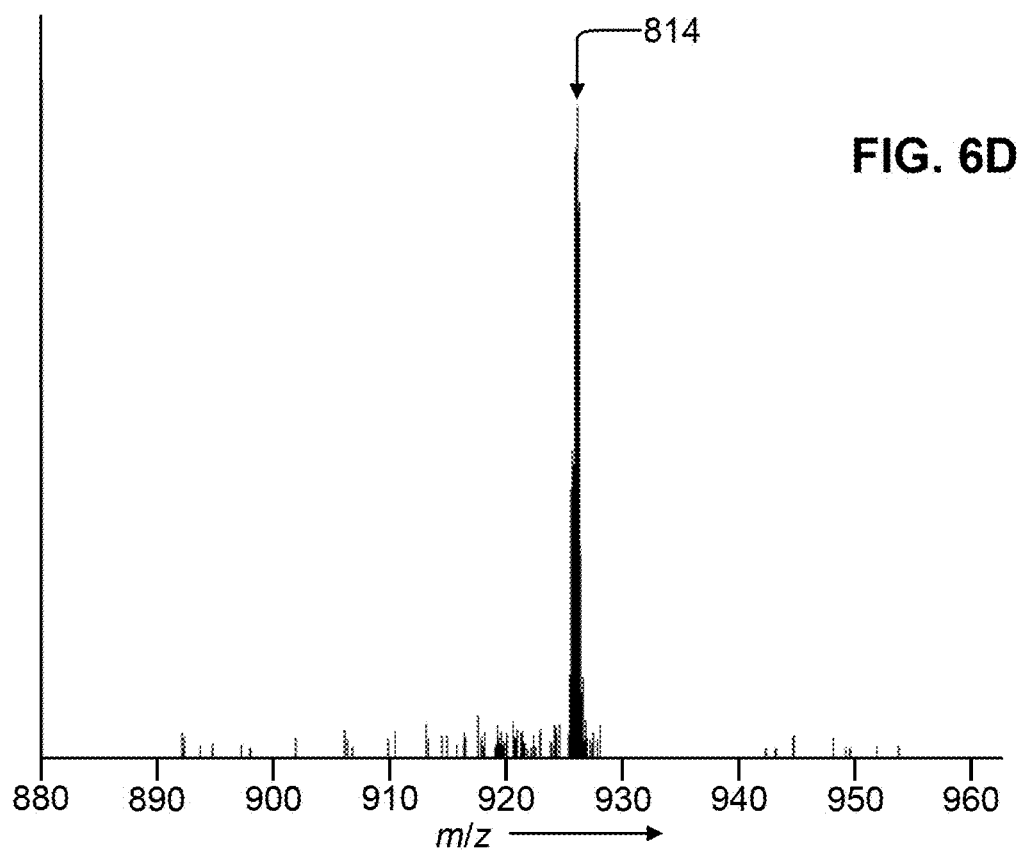
FIG. 6D is a mass spectrum of an isolated PTR product ion species selected from the product ion assemblage of FIG. 6A and having an m/z ratio of 926 Th.
Figure 6E:
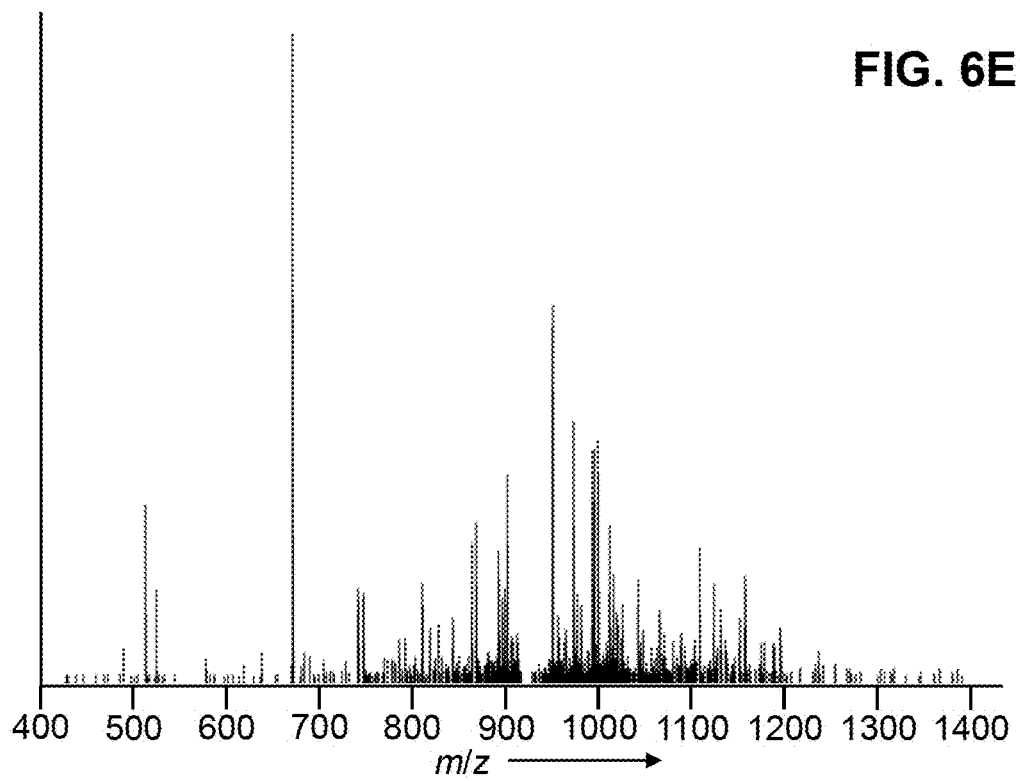
FIG. 6E is a mass spectrum of second-generation product ions generated by collision-induced dissociation of the isolated PTR product ion species of FIG. 6D.
Figure 6F:
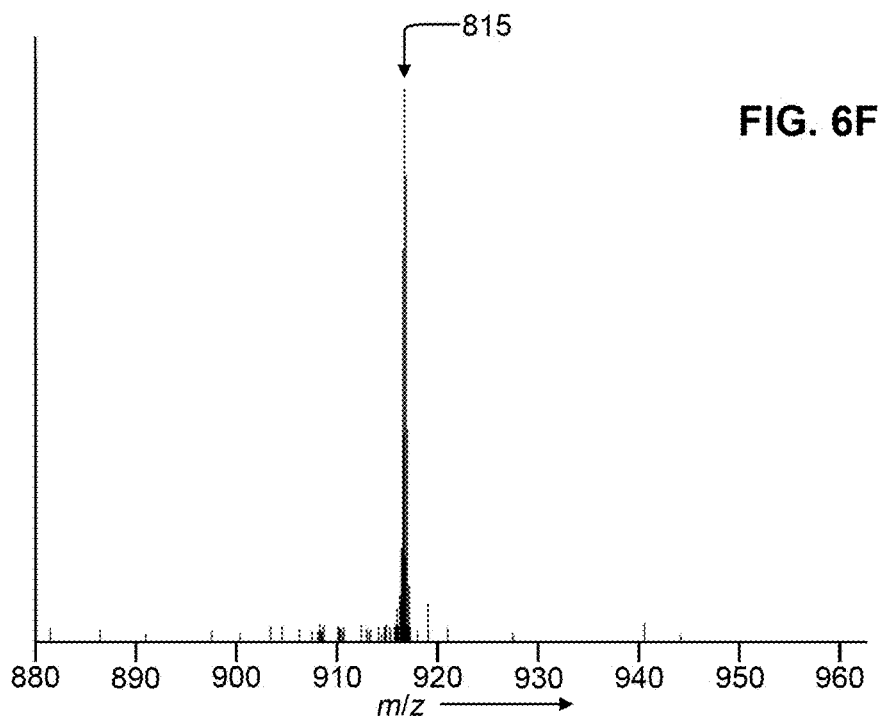
FIG. 6F is a mass spectrum of an isolated PTR product ion species selected from the product ion assemblage of FIG. 6A and having an m/z ratio of 917 Th.
Figure 6G:
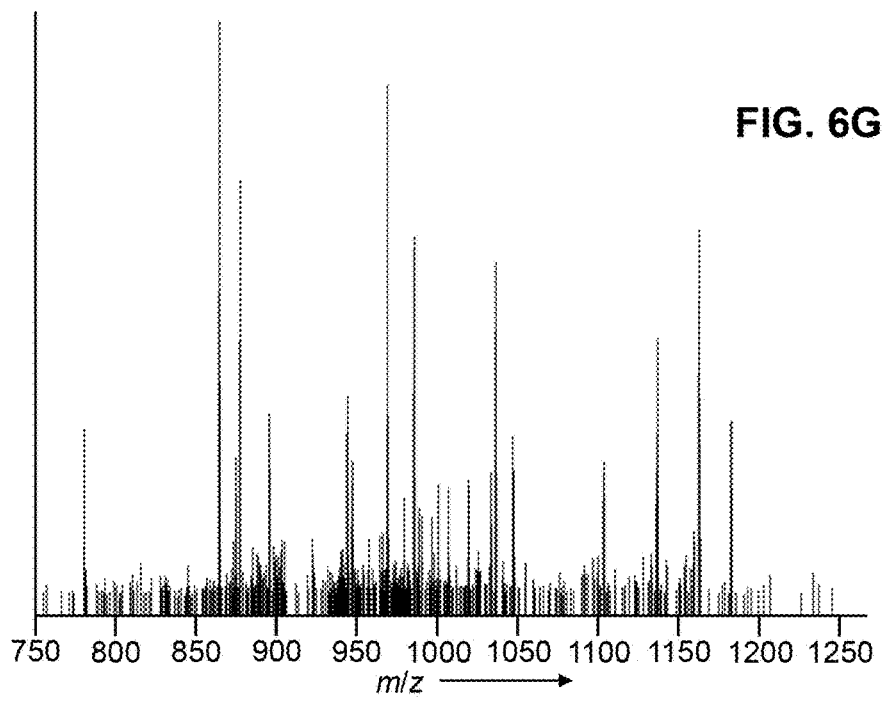
FIG. 6G is a mass spectrum of second-generation product ions generated by collision-induced dissociation of the isolated PTR product ion species of FIG. 6F.

FIGS. 6A-6G illustrate an example of analysis of an *E. coli* extract that is performed by a procedure that includes a first stage of product ion formation by PTR reaction followed by subsequent stages of CID of the PTR reaction product ions (for example, see steps 312 through 322 method 370 in FIG. 3B). FIG. 6A illustrates a PTR product ion spectrum generated isolated first-generation precursor ions from within a 5 Th mass window centered at m/z=640, indicated by position 811 in FIG. 6A. The PTR product ions occur at m/z ratios greater than that indicated by position 811 in FIG. 6A. The three most intense PTR product ions, located at m/z ratios of 833, 926 and 917 and indicated by mass spectral peaks 813, 814 and 815, respectively, in FIG. 6A, were then individually isolated and separately subjected to collision-induced dissociation so as to produce three sets of second-generation product ions. FIGS. 6B and 6C respectively depict the isolated PTR product ion at m/z=833 and the second generation product ions (fragment ions) generated by CID of the isolated PTR product ion. Likewise, FIGS. 6D and 6E respectively depict the isolated PTR product ion at m/z=926 and the second generation product ions generated by CID of the isolated PTR product ion at m/z=926. Likewise, FIGS. 6F and 6G respectively depict the isolated PTR product ion at m/z=917 and the second generation product ions generated by CID of the isolated PTR product ion at m/z=917.

Example C

As should be evident from the previous discussions, positive ion electrospray ionization of any protein or polypeptide molecule will produce a plurality of ions comprising different respective charge states (i.e., number of charges) as a result of different degrees of protonation of the original molecule. Charge states of +50 or more or possible and each charge state will be represented by multiple mass spectral lines representing different degrees of natural isotopic substitution. A further complication arises from the fact that for most natural biological samples, numerous different proteins of polypeptide molecules may be represented in a mass spectrum. A yet further complication arises from the fact that many other molecules—not necessarily of interest—may be present in a sample.

In many basic-research-oriented studies, the above-noted complicating factors of multiple analytes and multiple interfering species may be partially or wholly resolved by performing chromatic separation prior to introducing each separated compound individually into a mass spectrometer. However, clinical analyses may often be performed under tight time constraints that do not allow for traditional time-consuming chromatographic separation. The clinical time constraints may only allow for an incomplete or partial separation using either solid-phase extraction (SPE), size-exclusion chromatography, or the method of Fast Partial Chromatographic Separation (FPCS) described above. Thus, when such partial separation procedures are employed, the mass spectral signature of any particular protein or polypeptide may be spread out over a wide mass-to-charge ratio and may be complexly overlapped with the mass spectral signatures of other compounds. Since the available charge, as provided by an electrospray apparatus, will be spread out over many different types of ions, most of the observed mass spectral lines will coexist with and possibly be hidden within a general densely populated and low-intensity or ill-defined spectral "background" indicated schematically by spectral envelope 902 in FIGS. 7A-7B.

The inventors have realized that the mass spectral signature of any particular protein, polypeptide or other biologically relevant high-molecular-weight analyte may be hypothetically amplified by simultaneously isolating multiple charge states of the same original molecule and then reacting the assemblage of multiple charge states with PTR reagent ions so as to simultaneously reduce the assemblage to a small number of charge states distributed over a few charge-state values, these charge-state values being reduced relative to the original charge states. This concept is illustrated by the vertical boxes 904a-904g shown overlaid over the general charge-state envelope 902 in FIG. 7A. Each such vertical box represents a particular precursor ion species and represents a small range of m/z values chosen to correspond to a particular charge state (and possibly including a few isotopic variants) of a particular analyte. Hypothetically, if all ions outside of the ranges corresponding to the vertical boxes could be excluded and only the ions from within the indicated ranges mixed together, then subsequent PTR would essentially provide a summation of the signals from the various original plurality of charge states. The use of such multi-species isolation of a plurality of precursor ion species can increase the sensitivity of the analysis up to N-fold, where N is the number of m/z ranges selected and simultaneously isolated.

Such multiple-species isolation is fairly easy to achieve when isolation is performed in a linear ion trap (such as the low-pressure linear trap cell 217b illustrated in FIG. 2), because resonance-excitation waveforms, which are used to eject unwanted ions, may be constructed with multiple notches. Each such notch corresponds to a different respective m/z window within which ions will not be ejected (and thus isolated). Thus, the co-isolating of a plurality of electrospray-generated (first-generation) precursor ion species may be performed, in some embodiments, by simultaneously isolating all of the plurality of precursor ion species. One way of doing this is by applying a broadband resonance ejection frequency waveform to an ion trap into which ions received from an electrospray source have been introduced, wherein the waveform comprises multiple summed sinusoidal frequency components, wherein included frequency components corresponding to the m/z ranges of ions that one desires to eject from the trap and excluded frequency components correspond to the m/z range of ions that one desires to retain within the trap. In this procedure, the omitted frequencies define one or more frequency notches in the ejection frequency waveform. The frequency components may be calculated by first choosing a desired multi-notch waveform and then calculating an inverse Fourier Transform of the desired waveform.

Alternatively, the co-isolating of the plurality of precursor ion species may be performed by isolating individual precursor ion species in a conventional sense, one ion species at a time using a respective single-notch waveform applied to an ion trap. The individually isolated precursor ion species may be transferred, one at a time, to an ion storage component (such as the multipole ion guide 214 illustrated in FIG. 2) in which the various selected and isolated ion species are accumulated over time. As a yet-further alternative, the co-isolating of the plurality of precursor ion species may be performed by passing a plurality of ions received from an electrospray source through a quadrupole mass filter while the bandpass of the quadrupole mass filter is sequentially tuned to preferentially transmit, in turn, each m/z range corresponding to a particular precursor ion species. The filtered ions that pass through the quadrupole mass filter are then passed into an ion storage component that accumulates the ions from all the preferentially transmitted m/z ranges. For example, in the mass spectrometer 150a illustrated in FIG. 2, the quadrupole mass filter 208 may perform the sequence of filtering steps and the ions of each transmitted m/z range may be transmitted into and accumulated within the multipole ion guide 214. The accumulated precursor ion species may then be transferred back to the low-pressure cell 217b for PTR reaction.

The above-described procedure employing simultaneous multi-species isolation assumes that appropriate isolation ranges 904a-904g a priori known. Such knowledge about the correct isolation ranges to employ may be available in certain instances of targeted analysis, when the identity of (and other information pertaining to) an analyte that is to be searched for is already known and the purpose of the analysis is to determine the presence or absence of the analyte or to determine the quantity or concentration of the analyte. However, the above assumption may be invalid in the case of survey analyses, in which the identities of analytes may not be known in advance. In such latter cases, an initial random survey may be performed by isolating a random mass range 903 of the first-generation ions, as schematically depicted in FIG. 7B, and then reacting the isolated ions with a PTR reagent anion. As previously illustrated in FIGS. 4A and 4B, such a procedure can provide resolved, interpretable mass spectral lines relating to charge state distributions of one or more analytes. In many instances, a set of related lines may be recognized with by the mutual consistency of their m/z values with Eq. 1 for a certain sequence of consecutive integers, z. The degree of consistency of the line positions may be performed automatically, by computer analysis, such that overlapping sets of such related lines may be mathematically decomposed and recognized.

As an example of the above type of analysis, mathematical decomposition of the PTR product ion lines generated by isolation and reaction of precursor ions within m/z range 903 may lead to recognition of two overlapping sets of lines, depicted by envelope 905 and envelope 906, as illustrated in FIG. 7C. With the information provided by this initial survey procedure, an appropriate and consistent set of m/z values may be chosen, which may be employed in a subsequent simultaneous multi-species isolation and reaction procedure. For example, the m/z values of certain resolved instances of the lines under envelope 905 may be chosen, perhaps automatically. Subsequent multi-species isolation and PTR reaction of precursor ions corresponding to these chosen m/z values will then provide an amplified spectrum that may be employed to determine a quantity or concentration of the particular molecule represented by the envelope 905. This procedure may later be repeated using the associated with envelope 906 so as to determine a quantity or concentration of another molecule. The determined quantities or concentrations may not be accurate, in an absolute sense, but the ratios of the determined quantities or concentrations may provide useful information relating to relative quantities or concentrations. This entire procedure outlined above may be repeated multiple times using different randomly chosen m/z ranges 903, thereby providing determinations of relative quantities or concentrations of several compounds. As stated previously, control of such experiments can be accomplished in a data-dependent fashion utilizing the results of real-time spectral deconvolution.

Figure 8:
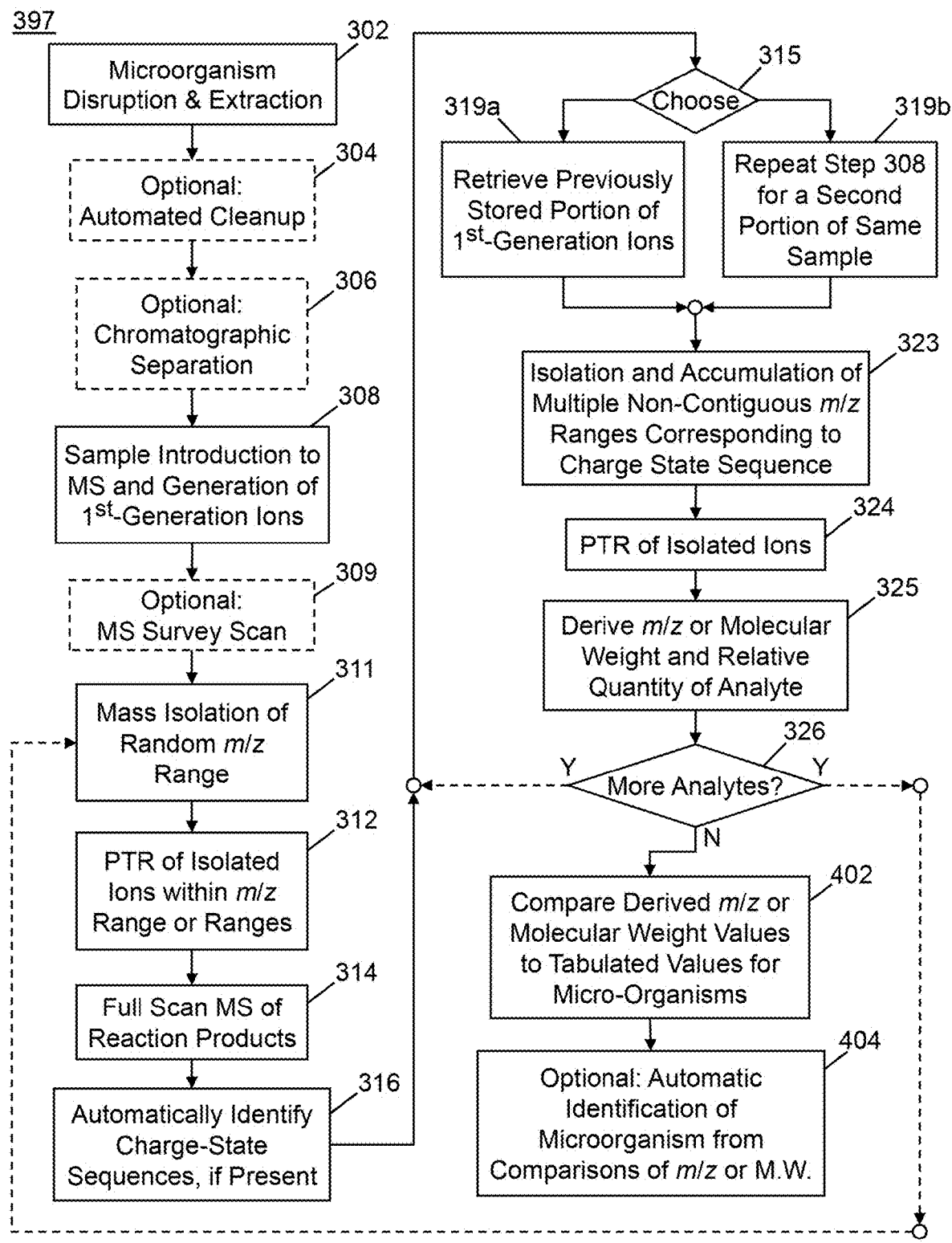
FIG. 8 is a flow diagram of a method, in accordance with the present teachings, of improved-efficiency PTR conversion of ions of a selected analyte to an assemblage of PTR product ions.

FIG. 8 provides a general flow diagram of an exemplary method, method 397, of survey analysis using the above-outlined PTR signal amplification by reaction of PTR reagent ions with first-generation ions from multiple non-contiguous m/z ranges. Steps 302, 304, 306, 308, 309, 312, 314, 316, 402 and 404 of the method 397 are identical to the similarly numbered steps of the method 300 illustrated in FIG. 3A and are thus not re-described here. Also, the new step 311 is similar to the previously described step 310 of method 300, except that step 311 refers only to mass isolation of a random m/z range (such as the range 903 depicted in FIG. 7C) of first-generation ions, instead of to a "random or predetermined m/z range or ranges" as described for the prior method 300. After the initial survey PTR reaction (step 312) and identification of charge-state sequences (step 316), the step 323 is executed, in which multiple non-contiguous m/z ranges of the first-generation ions are isolated and accumulated, wherein the non-contiguous m/z ranges correspond to an identified charge state sequence. The first-generation ions may be obtained from a previously stored batch of such ions (prior step 319a) or, alternatively (prior step 319b), the sample introduction and electrospray ion generation step may need to be repeated.

After the isolation and accumulation of multiple non-contiguous m/z ranges of the first-generation ions (step 323), the accumulated ions are reacted with PTR reagent ions (step 324). The resulting amplified spectra will generally be of high quality thereby facilitating the derivation (step 325) of, for example, an accurate molecular weight of the molecule corresponding the multiple non-contiguous m/z ranges or an accurate quantity, concentration, or relative abundance of such molecule. If an immediately prior execution of step 316 identified more than one set of related m/z ratios, then step 319a or 319b and steps 323-325 may be executed again (following the leftmost "Y" branch of step 326) using a new set of non-contiguous m/z ranges that correspond to a different identified charge state sequence. If a search for possible additional analytes is to be continued, then execution may return to step 311 (following the rightmost "Y" branch of step 326) at which a different random m/z range is chosen.

Example D

According to another method for reduction of sample complexity utilizing proton transfer reactions in accordance with the present teachings, mass spectrometric analysis employing PTR can be coupled directly with chromatography in order to simplify and detect additional proteins that would otherwise be missed. In this embodiment, a full scan mass spectrum is taken and the protein molecular weights are calculated using a real-time deconvolution program. Next, an isolation window is chosen of a defined width and the subset of m/z values in the window are subjected to PTR reactions.

Figure 9A:
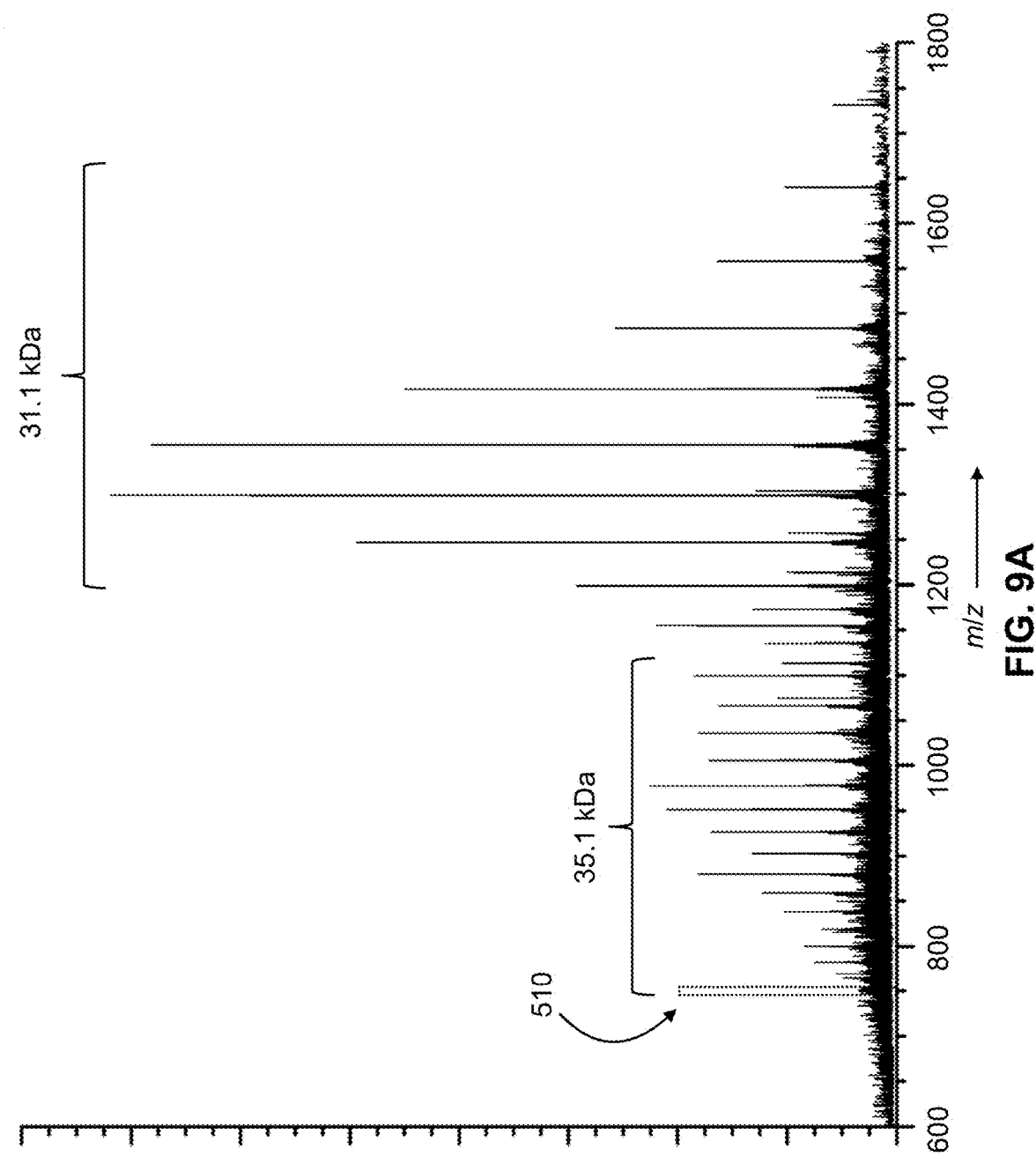
FIG. 9A is a full scan mass spectrum of first-generation ions generated from eluate at a retention time of 10 min. and 30 s. during the course of a ten-minute gradient reverse-phase liquid chromatography separation of an *E. coli* extract.
Figure 9B:
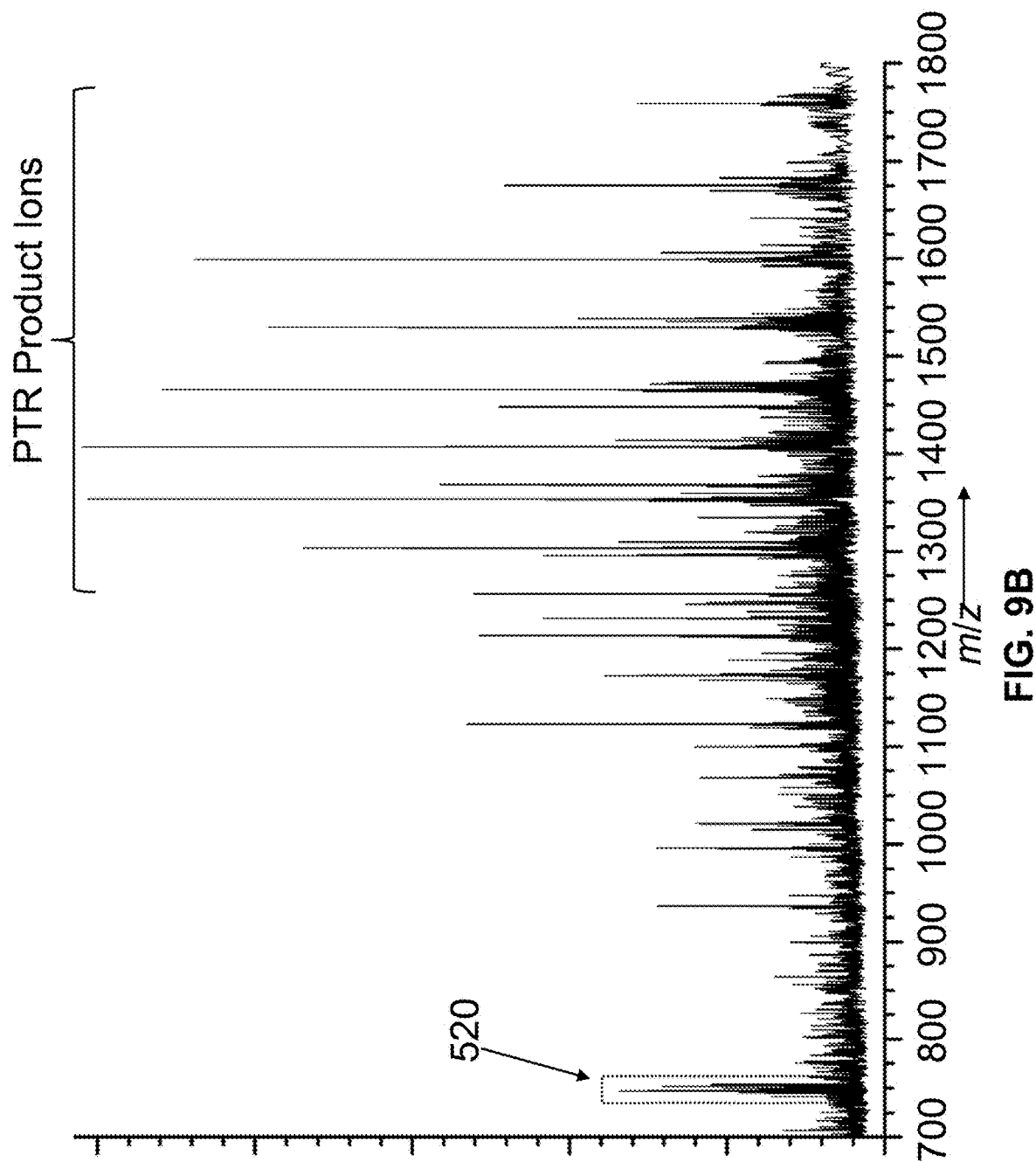
FIG. 9B is a PTR product ion spectrum generated by reacting sulfur hexafluoride for 10 ms with an isolated population of ions of the sample of FIG. 9A within a 10 Th wide isolation window centered at 750 Th.

For example, FIG. 9A shows a full scan mass spectrum of first-generation ions generated from eluate at a retention time of 10 min. and 30 s. during the course of a ten-minute gradient reverse-phase liquid chromatography separation of an E. coli extract. As indicated by the braces in FIG. 9A, this full-scan mass spectrum exhibits the distinct spectral signatures of two proteins having approximate molecular weights of 35.1 and 31.1 kDa respectively. For the next step, a population of ions having m/z values within an m/z isolation window 510 of 10 Th width and centered at 750 Th were isolated. The isolated ion population was then subjected to PTR reactions with the anionic reagent sulfur hexafluoride for 10 ms. The resulting product ion mass spectrum, shown in FIG. 9B, exhibits the mass spectral signatures of two additional proteins not seen in the full-scan mass spectrum having molecular weights of 11220.07 Da and 24599.56 Da. In addition, the 35.1 kDa protein component previously observed in the full-scan mass spectrum also exhibits a spectral signature in the PTR product ion spectrum which includes a line, outlined in box 520, corresponding to a +47 charge state at a nominal m/z value of 749. The line at 749 Th represents charge reduction of even-more-highly-charged states of the 35.1 kDa protein. The proteins observed at 11.2 and 24.6 kDa would not otherwise be identified in the absence of the PTR step in this example of a reverse-phase chromatographic run as a result of complex spectral overlap and interfering noise from an abundance of singly-charged background ions.

Figure 10A:
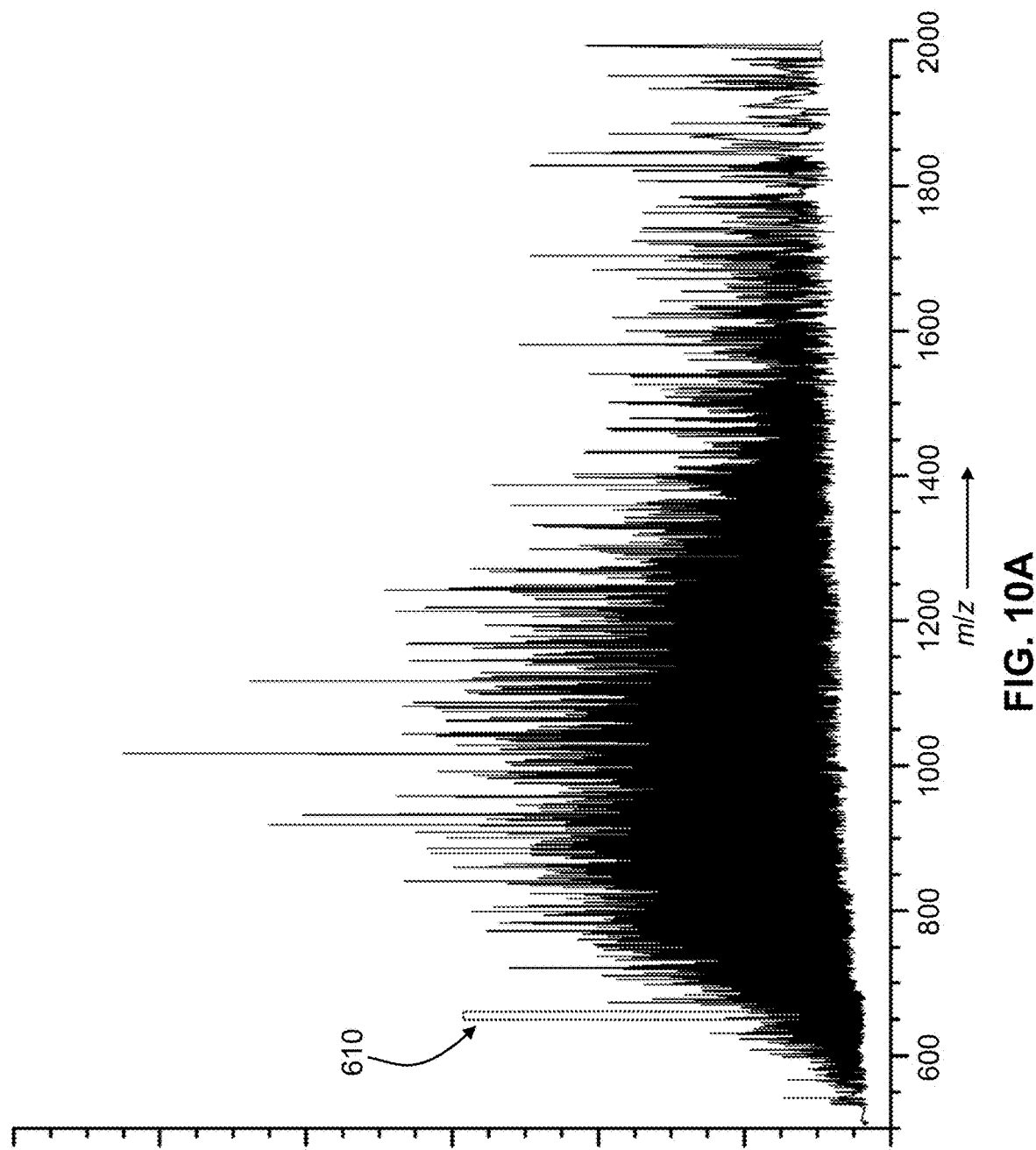
FIG. 10A is a full scan mass spectrum of first-generation ions generated from eluate at a retention time of 42 min. and 30 s. during the course of a sixty-minute gradient reverse-phase liquid chromatography separation of an *E. coli* extract.
Figure 10B:
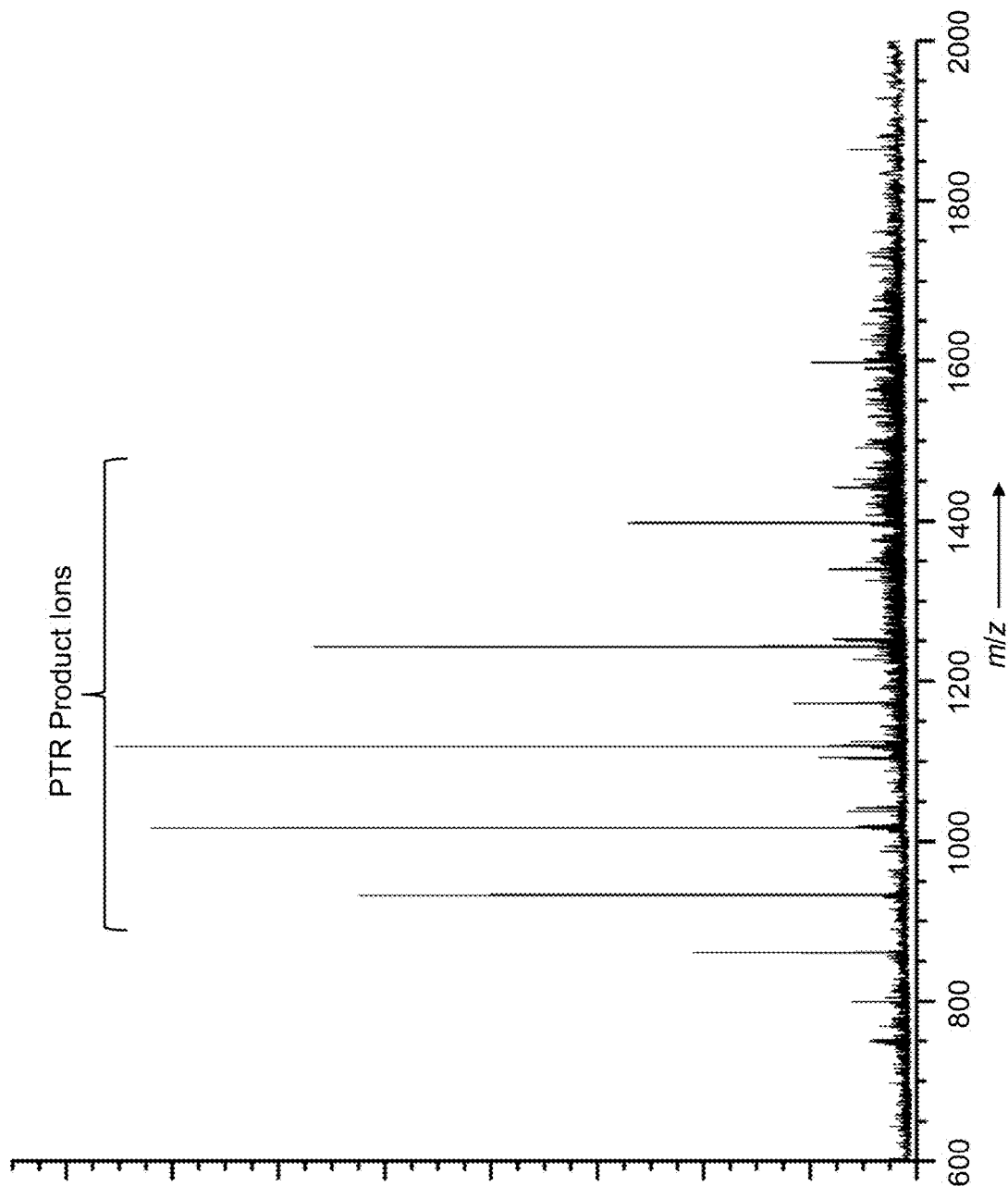
FIG. 10B is a PTR product ion spectrum generated by reacting sulfur hexafluoride for 10 ms with an isolated population of ions of the sample of FIG. 10A within a 10 Th wide isolation window centered at 750 Th.

FIGS. 10A and 10B show the results of a similar chromatography/MS experiment obtained from eluate at a retention time of 42 min. and 30 s. from a sixty-minute gradient elution run. As shown in FIG. 10A, a high background at this elution time causes difficulty in identifying analyte peaks in the full-scan spectrum. However, the PTR product ion spectrum plotted in FIG. 10B is much more amenable to interpretation and mass spectral deconvolution. The PTR product ion spectrum exhibits the mass spectral signatures of three distinct proteins—specifically having molecular weights 11165.92 Da, 13480.28 Da and 18727.23 Da—that would not otherwise be observed. In this instance, the PTR product ions were generated from isolated precursor ions generated from the mass spectral window, indicated by box 610 in FIG. 10A, of 10 Th width centered at m/z 750. By performing this type of analysis upon eluates that elute at various different retention times during the course of a single experiment, a sufficient number of sample peptides may be recognized so as to enable identification of a microorganism to the species, subspecies, or strain level. As also indicated by the results shown in FIGS. 9A-9B, if there is m/z overlap of protein ions from the full mass spectrum within the isolation window, then the protein will also be seen in the PTR product ion mass spectrum.

Figure 11B:
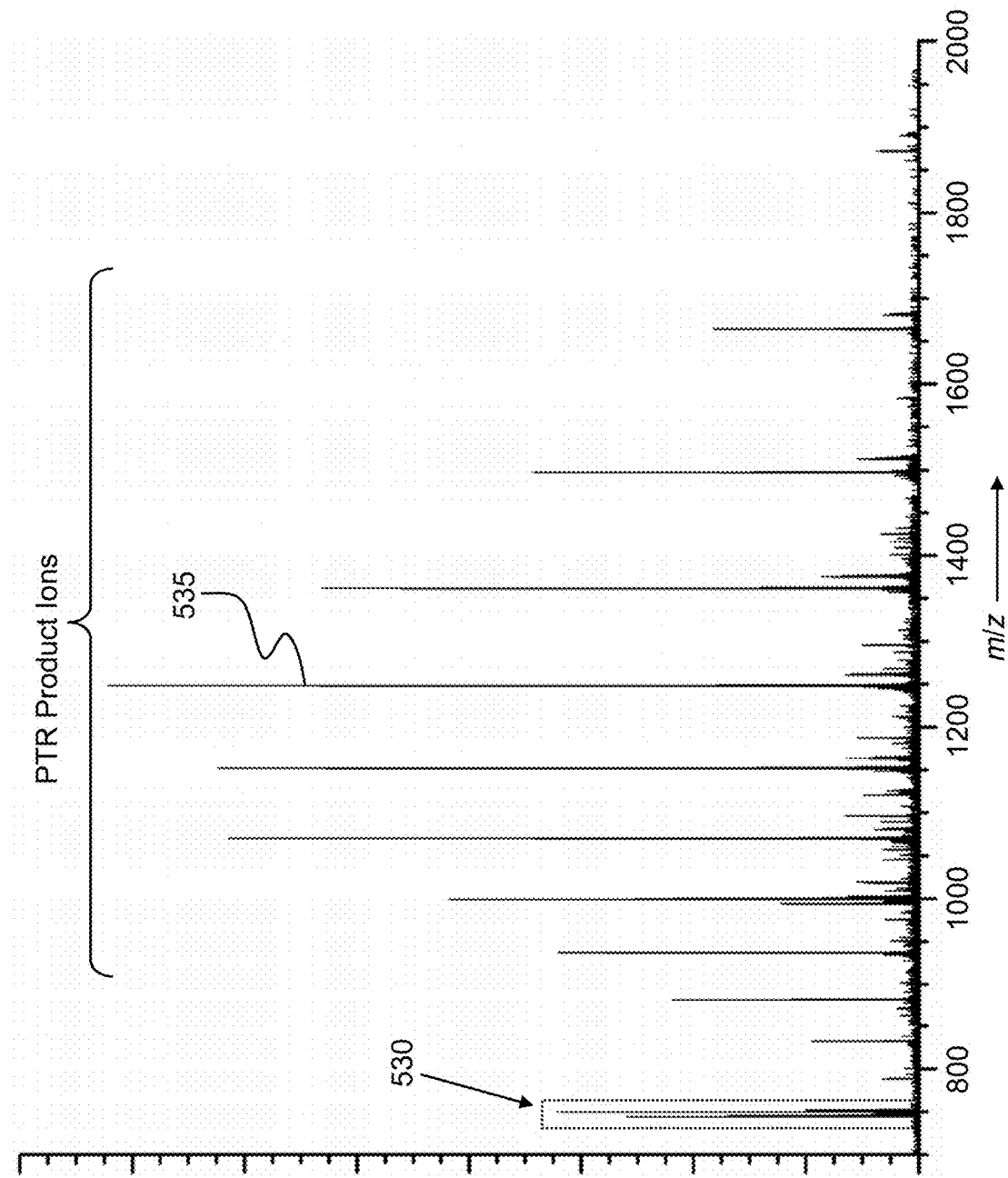
FIG. 11B is a PTR product ion spectrum generated by reaction of PTR reagent ions with an isolated population of ions of the sample of FIG. 11A within a 10 Th wide isolation window centered at 750 Th.
Figure 11C:
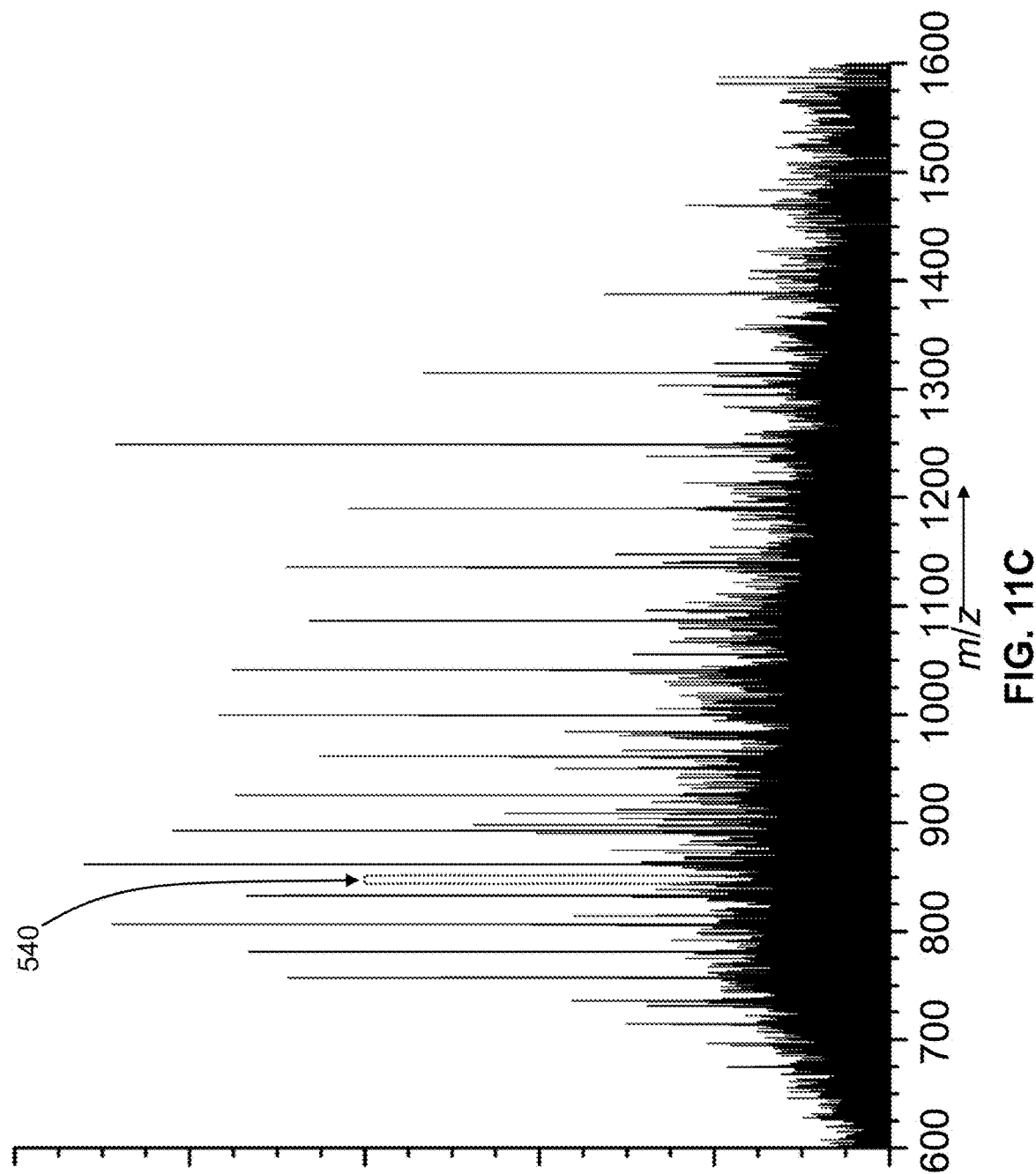
FIG. 11C is a full scan mass spectrum of first-generation ions generated from eluate at a retention time of 22 min. and 27 s. during the course of the same thirty-minute gradient reverse-phase liquid chromatography separation of which the earlier elution results are plotted in FIG. 11A.
Figure 11D:
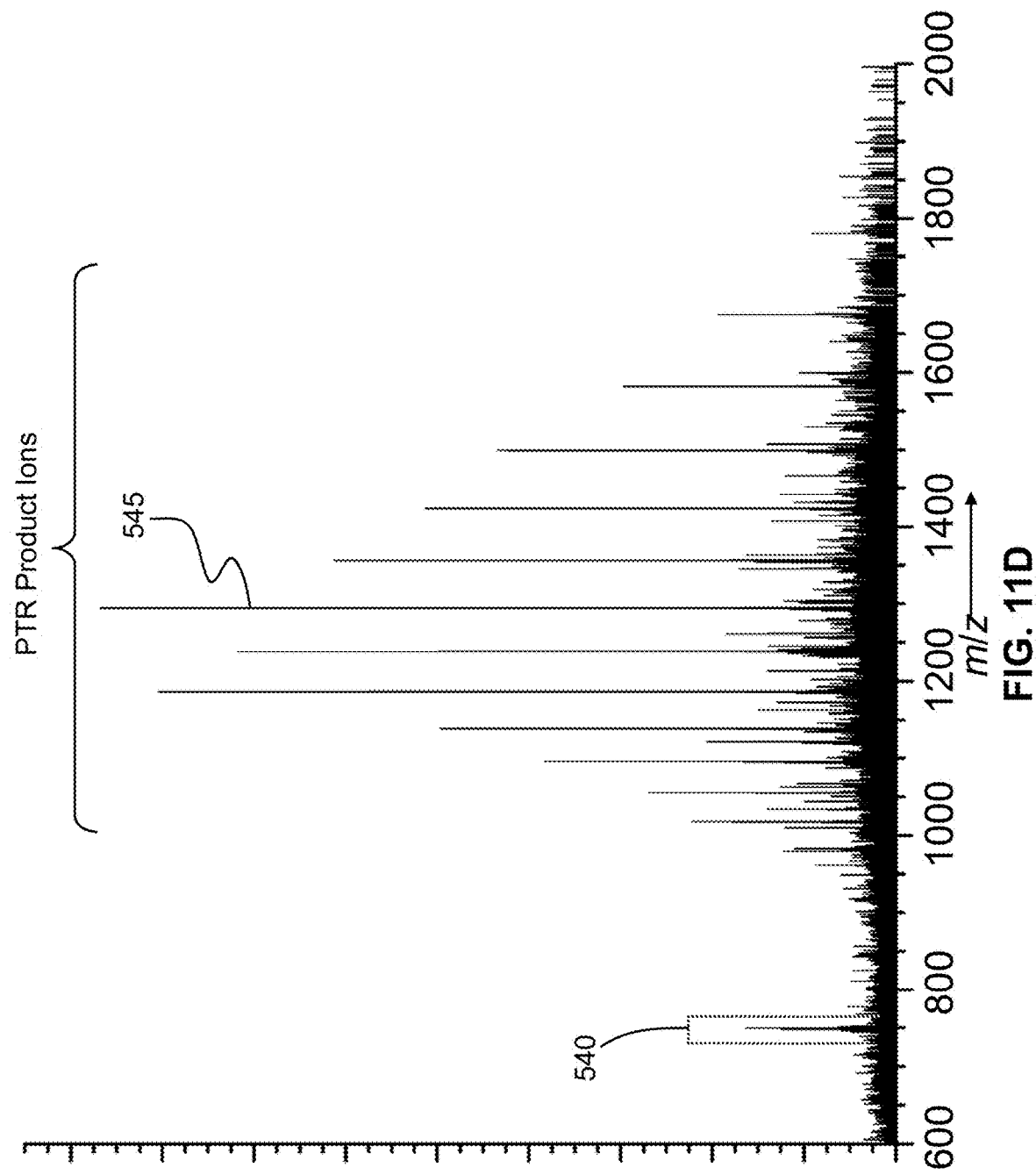
FIG. 11D is a PTR product ion spectrum generated by reaction of PTR reagent ions with an isolated population of ions of the sample of FIG. 11C within a 10 Th wide isolation window centered at 750 Th.

Interestingly, the full scan mass spectrum and PTR product-ion mass spectrum can provide complementary information, as illustrated in FIGS. 11A and 11B which represent mass spectral results obtained from eluate eluting at a retention time of 18 min. and 9 s. over the course of a thirty-minute chromatographic separation. In this example, the full-scan mass spectrum (FIG. 11A) exhibits a strong mass spectral signature of essentially a single protein having a molecular weight of 9534.3 Da, However, when a PTR product ion spectrum is generated from ions isolated within a 10 Th wide window centered around m/z 750 Th (box 530), the mass spectral signature comprises a strong signal from a protein having a molecular weight of 14965.5 Da (best represented by the peak 535 of the +12 charge state at approximately 1247 Th) along with five other minor proteins having molecular weights of 12669.8 Da, 14150.0 Da, 14236.1 Da, 14965.5 Da, and 15117.5 Da. FIG. 11C is a full-scan mass spectrum obtained from eluate eluting during the same chromatographic separation at a retention time of 22 min. and 27 s. The spectrum includes peaks indicating the presence of a protein having a molecular weight of 24961.3 Da. Upon PTR reaction of ions isolated within the isolation window 540, the PTR product ion spectrum shown in FIG. 11D was obtained. The mass spectral signature in the PTR product ion spectrum includes a relatively strong signal from a protein having a molecular weight of 28461.5 Da (best represented by the peak 545 of the +22 charge state at approximately 1294 Th) as well as two other proteins having molecular weights of 18590.5 Da and 20168.0 Da. Thus, from just the data at these two retention times, it is possible to detect the presence and the molecular weights of eleven different proteins.

ADDITIONAL EXAMPLES

The following paragraphs list additional specific examples of various specific embodiments in accordance with the present teachings.

Example 1

A method for identifying the presence or absence of a protein or polypeptide analyte compound within a liquid sample comprising a mixture of compounds that includes a plurality of protein compounds or a plurality of polypeptide compounds or pluralities of both protein and polypeptide compounds, the method comprising:

(a) introducing a portion of the liquid sample into an electrospray ionization source of a mass spectrometer;

(b) forming positively charged ions of the mixture of compounds of the portion of the liquid sample by electrospray ionization, the positively charged ions comprising a plurality of ion species;

(c) isolating a first subset of the ion species comprising a first mass-to-charge (m/z) ratio range that includes an m/z ratio of a particular predetermined multiply-protonated molecular species of the analyte compound;

(d) generating a plurality of first-generation product ion species from the isolated first subset of ion species by causing the isolated first subset of ion species to be reacted, for a predetermined time duration, with reagent anions that, upon reaction, extract protons from each of one or more ion species that comprises a protonated molecular species of a protein or polypeptide compound;

(e) generating a mass spectrum, using a mass analyzer, of either the first-generation product ion species or of second-generation product ion species generated from the first-generation product ion species;

(f) conducting a search of the mass spectrum of either the first-generation or the second-generation product ion species for a set of one or more m/z ratios that are diagnostic of the protein or polypeptide analyte compound; and (g) identifying the presence of the analyte compound within the sample if the set of one or more m/z ratios is identified in the mass spectrum.

Example 2

A method as recited in Example 1, further comprising repeating the steps (a) through (e) a second time, wherein the steps (f) and (g) are performed during or prior to the second performing of the steps (a) through (e).

Example 3

A method as recited in Example 1, further comprising repeatedly performing steps (a) through (g) a plurality of times, wherein each repetition of step (a) comprises introducing, into the electrospray ionization source, an eluate from a chromatographic column corresponding to a respective retention time.

Example 4

A method as recited in Example 1, wherein the step (f) comprises conducting a search of the mass spectrum of the first-generation product ion species for a series of m/z ratios that correspond to a sequence of multiply-protonated ion species of the analyte compound that are progressively charge-reduced with respect to the charge state of the particular predetermined multiply-protonated molecular species.

Example 5

A method as recited in Example 1, wherein:
the step (c) comprises further isolating a second subset of the ion species comprising a second m/z ratio range that includes an m/z ratio of a particular predetermined multiply-protonated molecular species of a second protein or polypeptide analyte compound;
the step (f) comprises conducting an additional search of the mass spectrum of either the first-generation or the second-generation product ion species for a second set of one or more m/z ratios that are diagnostic of the second protein or polypeptide analyte compound; and
the step (g) comprises identifying the presence of the second analyte compound within the sample if the second set of m/z ratios is identified in the mass spectrum.

Example 6

A method as recited in Example 5, wherein the first m/z ratio range is identical to the second m/z ratio range.

Example 7

A method as recited in Example 5, wherein the step (c) comprises simultaneously isolating the first subset of the ion species comprising the first m/z ratio and the second subset of the ion species comprising the second m/z ratio range such that the first and second m/z ratio ranges are non-contiguous.

Example 8

A method as recited in Example 1, wherein the step (d) of generating a plurality of first-generation product ion species comprises causing the isolated first subset of ion species and reagent anions to be reacted for a time duration that causes the product ion species to be stable against decomposition during the subsequent generation of the mass spectrum in step (e).

Example 9

A method as recited in Example 8, wherein the step (e) comprises generating a mass spectrum of the first-generation product ion species using a mass analyzer that generates the mass spectrum by detecting image currents caused by motions of the ions of the product ion species within an ion trap.

Example 10

A method as recited in Example 1, wherein the step (d) of generating a plurality of first-generation product ion species includes applying a supplemental AC voltage across electrodes of an ion trap within which the isolated first subset of ion species are reacted with reagent anions, wherein a frequency of the supplemental AC voltage is such that ion-ion reaction between the reagent anions and selected first-generation product ion species is inhibited.

Example 11

A method as recited in Example 10, wherein the frequency of the supplemental AC voltage is such that, subsequent to the execution of step (d), product ions formed from the analyte compound exist substantially as a single ion species having a particular charge state.

Example 12

A method as recited in Example 11, wherein:
the step (e) comprises generating a mass spectrum of the first-generation product ion species; and
wherein the mass of the single ion species is greater than 20,000 Da and the charge state of the single ion species is sufficiently great such that ions of the single ion species may be detected, during the generation of the mass spectrum, by either a quadrupole mass analyzer, a Fourier transform ion cyclotron resonance mass spectrometer or an electrostatic trap mass analyzer.

Example 13

A method as recited in Example 1, wherein the step (e) of generating a mass spectrum comprises generating a mass spectrum of second-generation product ion species, wherein the second-generation product ion species are generated by the steps of:
isolating a subset of the first-generation product ion species comprising a particular product-ion m/z ratio range; and
fragmenting the isolated subset of the first-generation product ion species so as to form fragment ion species, wherein the fragment ion species comprise the second-generation product ion species.

Example 14

A method as recited in Example 1, wherein the step (e) of generating a mass spectrum comprises generating a mass spectrum of second-generation product ion species, wherein the second-generation product ion species are generated by:
causing the first-generation product ion species to be reacted, for a second predetermined time duration, with the reagent anions, wherein products of reaction between the first-generation product ion species and the reagent anions comprise the second-generation product ion species.

Example 15

A method as recited in Example 14, wherein a supplemental AC voltage is applied across electrodes of an ion trap within which the first-generation product ion species are reacted with the reagent anions, wherein a frequency of the supplemental AC voltage is such that ion-ion reaction between the reagent anions and selected product ion species is inhibited.

Example 16

A method as recited in any one of Examples 1-15, further comprising generating the liquid sample comprising the mixture of compounds by a procedure comprising:
(i) culturing microorganisms or cells;
(ii) lysing the cultured microorganisms or cells; and
(iii) extracting proteins from the lysate of cultured microorganisms or cells.

Example 17

A method as recited in Example 16, wherein the step (iii) of extracting the liquid sample from the lysate includes passing the lysate through a solid-phase-extraction apparatus.

Example 18

A method of identifying the presence or absence of a microorganism type in a sample, comprising:
(i) identifying a list of analyte compounds whose simultaneous presence in the sample is diagnostic of the presence of the microorganism type in the sample, said list of analyte compounds comprising protein compounds, polypeptide compounds or both protein and polypeptide compounds;
(ii) extracting, from the sample, a liquid solution comprising a mixture of sample-derived proteins and polypeptides;
(iii) for each respective analyte compound in the list, performing the steps of:
(a) introducing a portion of the liquid solution into an electrospray ionization source of a mass spectrometer;
(b) forming positively charged ions of the mixture of compounds of the portion of the liquid solution by electrospray ionization, the positively charged ions comprising a plurality of ion species;
(c) isolating a first subset of the ion species comprising a first mass-to-charge (m/z) ratio range that includes an m/z ratio of a particular predetermined multiply-protonated molecular species of the respective analyte compound;
(d) generating a plurality of first-generation product ion species from the isolated first subset of ion species by causing the isolated first subset of ion species to be reacted, for a predetermined time duration, with reagent anions that, upon reaction, extract protons from each of one or more ion species that comprises a protonated molecular species of a protein or polypeptide compound;
(e) generating a mass spectrum, using a mass analyzer, of either the first-generation product ion species or of second-generation product ion species generated from the first-generation product ion species;
(f) conducting a search of the mass spectrum of either the first-generation or the second-generation product ion species for a set of one or more m/z ratios that are diagnostic of the respective analyte compound; and
(g) identifying the presence of the respective analyte compound within the liquid solution if the set of one or more m/z ratios is identified in the mass spectrum; and
(iv) identifying the presence of the microorganism type within the sample if the presence of each and every analyte compound of the list of analyte compounds is identified within the liquid solution.

Example 19

A method of identifying the presence or absence of a microorganism type in a sample, comprising:
(i) identifying a list of analyte compounds whose simultaneous presence in the sample is diagnostic of the presence of the microorganism type in the sample, said list of analyte compounds comprising protein compounds, polypeptide compounds or both protein and polypeptide compounds;
(ii) extracting, from the sample, a liquid solution comprising a mixture of sample-derived proteins and polypeptides;
(iii) introducing at least a first portion of the liquid solution into an ionization source of a mass spectrometer;
(iv) generating, from the at least first portion of the liquid solution at the ionization source, positively charged ions of the mixture of compounds, the positively charged ions comprising a plurality of ion species;
(v) isolating at least a first subset of the plurality of ion species, each isolated subset of the at least a first isolated subset comprising a respective mass-to-charge (m/z) ratio range;
(vi) generating a plurality of first-generation product ion species from each isolated subset of ion species by causing each said isolated subset of ion species to be reacted, for a predetermined time duration, with reagent anions that, upon reaction, extract protons from each of one or more ion species of said isolated subset of ion species that comprises a protonated molecular species of a protein or polypeptide compound;
(vii) generating at least one mass spectrum, using a mass analyzer of the mass spectrometer, of either first-generation product ion species or second-generation product ion species generated by further reaction of the first-generation product ion species;
(viii) for each respective analyte compound in the list, performing the steps of:
(a) conducting a search of the at least one mass spectrum of either the first-generation or the second-generation product ion species for a set of one or more m/z ratios that are diagnostic of the respective analyte compound; and (b) identifying the presence of the respective analyte compound within the liquid solution if the set of one or more m/z ratios is identified in the mass spectrum; and (ix) identifying the presence of the microorganism type within the sample if the presence of each and every analyte compound of the list of analyte compounds is identified within the liquid solution.

Example 20

A method as recited in Example 19, wherein a performing of the steps (a) and (b) is performed concurrently with the performing of one or more of the steps (iii) through (vii).

Example 21

A method as recited in Example 19, wherein the microorganism type is defined as a particular genus of bacteria and the list of analyte compounds includes a sufficient number of analyte compounds that are diagnostic of the particular genus of bacteria to enable identification of the presence or absence of the particular genus of bacteria in the sample.

Example 22

A method as recited in Example 19, wherein the microorganism type is defined as a particular species of bacteria and the list of analyte compounds includes a sufficient number of analyte compounds that are diagnostic of the particular species of bacteria to enable identification of the presence or absence of the particular species of bacteria in the sample.

Example 23

A method as recited in Example 19, wherein the microorganism type is defined as a particular sub-species of bacteria and the list of analyte compounds includes a sufficient number of analyte compounds that are diagnostic of the particular sub-species of bacteria to enable identification of the presence or absence of the particular sub-species of bacteria in the sample.

Example 24

A method as recited in Example 19, wherein the microorganism type is defined as a particular strain of virus and the list of analyte compounds includes a sufficient number of analyte compounds that are diagnostic of the particular viral strain to enable identification of the presence or absence of the particular viral strain in the sample.

Example 25

A method as recited in Example 19, wherein the microorganism type is defined as a particular strain of virus and the list of analyte compounds includes a sufficient number of analyte compounds that are diagnostic of the particular viral strain to enable identification of the presence or absence of the particular viral strain in the sample.

Example 26

A method for identifying the presence or absence of a protein or polypeptide analyte compound within a sample comprising a mixture of compounds that includes a plurality of protein compounds or a plurality of polypeptide compounds or pluralities of both protein and polypeptide compounds, the method comprising:

(a) introducing a portion of the liquid sample into an electrospray ionization source of a mass spectrometer;

(b) forming positively charged ions of the mixture of compounds of the portion of the liquid sample by electrospray ionization, the positively charged ions comprising a plurality of first-generation ion species;

(c) isolating a plurality of subsets of the first-generation ion species comprising respective mass-to-charge (m/z) ratio ranges, wherein each m/z ratio range includes an m/z ratio of an ion species comprising a respective protonation state of the analyte compound;

(d) generating a plurality of first-generation product ion species from the isolated plurality of subsets of the first-generation ion species by causing the isolated plurality of subsets of the first-generation ion species to be reacted, for a predetermined time duration, with reagent anions that, upon reaction, extract protons from each ion species that comprises a respective protonation state of the analyte compound;

(e) generating a mass spectrum of the first-generation product ion species; and (f) identifying either the presence of the analyte compound within the sample if the mass spectrum comprises one or more lines at respective predetermined m/z ratios that comprise respective intensities above a predetermined threshold or the absence of the analyte compound within the sample otherwise.

Example 27

A method as recited in Example 26, further comprising repeatedly performing steps (a) through (f) a plurality of times, wherein each repetition of step (a) comprises introducing, into the electrospray ionization source, an eluate from a chromatographic column corresponding to a respective retention time.

Example 28

A method as recited in Example 26, wherein the step (f) further comprises determining, if the mass spectrum comprises one or more lines at respective predetermined m/z ratios that comprise respective intensities above a predetermined threshold, a quantity or concentration of the analyte compound within the sample based on the one or more intensities.

Example 29

A method as recited in Example 26, further comprising, after the step (b) of forming positively charged ions and prior to the step (c) of isolating a plurality of subsets of the first-generation ion species, the steps of:

(b1) isolating a subset of the first-generation ion species comprising a randomly-selected mass-to-charge (m/z) ratio range;

(b2) generating a plurality of product ion species from the isolated subsets of the first-generation ion species by causing the isolated subset of the first-generation ion species to be reacted with reagent anions that, upon reaction, extract protons from each ion species that comprises a respective protonation state of the analyte compound or a respective protonation state of another protein or polypeptide compound;

(b3) generating a mass spectrum of the product ion species; and (b4) automatically determining the m/z ratio ranges to be used in the subsequent step (c), based on the mass spectrum of the product ions.

Example 30

A method as recited in Example 28, wherein the step (b4) comprises automatically determining, from the mass spectrum, a set of m/z ratios corresponding to multiply-protonated ion species of the other protein or polypeptide compound.

Example 31

A method of identifying the presence of absence of a microorganism in a sample, comprising:
making an extract of the sample;
repeatedly executing the method recited in Example 26 so as to, at each execution, identify the presence or absence of a different respective protein or polypeptide analyte compound within the sample extract; and
identifying the presence of the microorganism within the sample if the presence of each respective protein or polypeptide analyte compound within the sample extract or the absence of the microorganism within the sample otherwise.

CONCLUSIONS

The use of PTR-type of ion-ion reactions as taught in this document has several advantages for analysis of complex mixtures of protein or polypeptide ions. A first significant advantage is provided by the greatly improved signal-to-noise ratio as may be readily observed by comparing FIG. 3 with FIG. 4. Even though some charge is lost (i.e., complete neutralization) as a result of the PTR process, a significant signal-to-noise ratio is gained as a result of the reaction of multiply-charged proteins with singly charged anions. The rate of such a reaction is proportional to the square of the product of the charges. Thus, the originally highly-charged analyte ions are converted into less-charged PTR product ions whose mass spectral signatures appear at significantly greater mass-to-charge ratios. By contrast, low-charge-state chemical background ions are less significantly affected by the PTR process during a typical experimental reaction period because of the low rates of reaction of such ions. This process essentially removes the mass spectral signatures of the proteins and polypeptides from the low-mass, low-charge-state chemical background "noise". For example, as shown in FIG. 4, the background ions are represented by the large singly-charged peak that is "left behind" at m/z≈642. It is also believed that adducts or water molecules still adhered to large proteins are removed as a result of the exothermic heat of reaction (at least 125 kcal/mol) deposited by the PTR reaction. The transformation of such ions into simple protonated molecules may further enhance signal-to-noise characteristics. Potentially, the number of protein identifications obtained via this approach could exceed current complex top-down methods utilizing some form of separation technology.

A second important advantage associated with methods in accordance with the present teachings is provided by greatly improved charge state assignment. For example, the inventors have experimentally determined that approximately 75% of the charge state assignments for individual charge states may be correctly assigned by employing methods in accordance with the present teachings. This improved ability to recognize charge states results from the significantly improved signal-to-noise ratio. In turn, this provides more accurate determination of the molecular weight of the protein or polypeptide. This comparison applies to the current Patterson-FFT charge state algorithm that is frequently used for real-time charge state determination. Another important advantage associated with methods in accordance with the present teachings is provided by the ability to perform rapid throughput analyses. When combined with the Fast Partial Chromatographic Separation technique applied above, these methods allow for analyses of samples in a high throughput fashion on a time scale of one minute or less.

The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. Thus, the reader should be aware that the specific discussion may not explicitly describe all embodiments possible; many alternatives are implicit. Accordingly, many modifications may be made by one of ordinary skill in the art without departing from the scope of the invention as described by the claims. Neither the description nor the terminology is intended to limit the scope of the invention. Any patents, patent applications, patent application publications or other literature mentioned herein are hereby incorporated by reference herein in their respective entirety as if fully set forth herein.

What is claimed is:

1. A method of identifying the presence of absence of a microorganism in a sample, comprising:
(i) making an extract of the sample;
(ii) repeatedly performing the steps of:
  (a) choosing a respective one of a plurality of pre-determined protein or polypeptide analyte compounds, said pre-determined protein or polypeptide analyte compounds being diagnostic of the microorganism;
  (b) introducing a portion of the extract into an electrospray ionization source of a mass spectrometer, thereby generating, from the sample extract, positively charged ions comprising a plurality of ion species;
  (c) isolating a plurality of subsets of the first-generation ion species comprising respective mass-to-charge (m/z) ratio ranges, wherein each m/z ratio range includes an m/z ratio corresponding to a respective protonation state of the chosen analyte compound;
  (d) introducing reagent anions from a reagent ion source into an ion trap of the mass spectrometer, wherein the reagent anions are capable of extracting protons from each ion species that comprises a respective protonation state of the chosen analyte compound;
  (e) generating a plurality of product ion species by reacting the isolated plurality of subsets of the first-generation ion species with the reagent anions within the ion trap for a predetermined time duration;
  (f) generating a mass spectrum of the product ion species; and
  (g) identifying either the presence of the analyte compound within the sample if the mass spectrum comprises one or more lines at respective predetermined ink ratios having intensities above a predetermined threshold or the absence of the analyte compound within the sample otherwise; and (iii) identifying the presence of the microorganism within the sample if the presence of each pre-determined protein or polypeptide analyte compound within the extract is identified or, otherwise, identifying the absence of the microorganism within the sample.

2. A method as recited in claim 1, wherein each repetition of step (b) comprises introducing, into the electrospray ionization source, an eluate from a chromatographic column corresponding to a respective retention time.

3. A method as recited claim 1, wherein the step (g) further comprises determining a quantity or concentration of the analyte compound within the sample based on the one or more intensities if said one or more intensities are above the pre-determined threshold.

4. A method as recited in claim 1, wherein the microorganism is a particular species or a particular sub-species of bacteria.

5. A method as recited in claim 1, wherein the microorganism is a particular viral strain or viral serovar.

6. A method as recited in claim 1, further comprising generating making the extract of the sample by a procedure comprising:
   culturing microorganisms or cells;
   lysing the cultured microorganisms or cells; and
   extracting proteins or polypeptides from the lysate of cultured microorganisms or cells.

7. A method as recited in claim 6, wherein the extracting of proteins from the lysate includes passing the lysate through a solid-phase-extraction apparatus.

8. A mass spectrometer system comprising:
   (i) an electrospray ionization source fluidically coupled to a source of sample;
   (ii) a mass filter configured to receive sample ions generated by the electrospray ion source;
   (iii) a source of proton transfer reaction (PTR) reagent anions;
   (iv) an ion trap configured to receive at least a portion of the sample ions from the mass filter and to receive the PTR reagent anions from the PTR reagent anion source;
   (v) a mass analyzer and detector configured to receive and analyze product ions generated by mixing of the sample ions and PTR reagent anions in the ion trap; and
   (vi) an electronic control unit or processor electrically coupled to the source of PTR ions, the ion trap, and the mass analyzer and detector, the electronic control unit or processor comprising machine readable program instructions operable to:
   (a) cause the mass filter to isolate a plurality of subsets of the sample ions comprising respective mass-to-charge (m/z) ratio ranges, wherein each m/z ratio range includes an m/z ratio corresponding to a respective protonation state of a pre-determined protein or polypeptide analyte;
   (b) cause the isolated plurality of subsets of the sample ions to be reacted, for a predetermined time duration, with PTR reagent anions so as to generate product ions;
   (c) cause the mass analyzer to generate a mass spectrum of the product ions; and
   (d) identify either the presence of the protein or polypeptide analyte within the sample if the mass spectrum comprises one or more lines at respective predetermined m/z ratios having intensities above a predetermined threshold or, otherwise, the absence of the protein or polypeptide analyte within the sample.

9. A mass spectrometer system as recited in claim 8, wherein the electronic control unit or processor further comprises machine readable program instructions operable to:
   cause the repeated execution of steps (a) through (d), each repetition of the step (a) corresponding to a different respective protein or polypeptide analyte compound; and
   identify the presence of a microorganism within the sample if the presence of each pre-determined protein or polypeptide analyte compound within the sample is identified or, otherwise, identify the absence of the microorganism within the sample.

10. A mass spectrometer system as recited in claim 8,
   wherein the machine readable program instructions that are operable to cause the mass filter to isolate a plurality of subsets of the sample ions comprising respective mass-to-charge (m/z) ratio ranges are further operable to cause the mass filter to simultaneously isolate the plurality of subsets of the sample ions comprising the respective mass-to-charge (m/z) ratio ranges, wherein each m/z ratio range includes an m/z ratio corresponding to a respective protonation state of a pre-determined protein or polypeptide analyte, and
   wherein the machine readable program instructions that are operable to cause the isolated plurality of subsets of the sample ions to be reacted, for a predetermined time duration, with PTR reagent anions so as to generate product ions are further operable to cause the isolated plurality of subsets of the sample ions to be simultaneously reacted, for the predetermined time duration, with the PTR reagent anions so as to generate the product ions.

11. A method as recited in claim 1,
   wherein the step (c) of isolating a plurality of subsets of the first-generation ion species comprising respective mass-to-charge (m/z) ratio ranges comprises simultaneously isolating the plurality of subsets of the first-generation ion species comprising the respective mass-to-charge (m/z) ratio ranges, wherein each m/z ratio range includes an m/z ratio corresponding to a respective protonation state of the chosen analyte compound, and
   wherein the step (e) of generating a plurality of product ion species by reacting the isolated plurality of subsets of the first-generation ion species with the reagent anions within the ion trap for a predetermined time duration comprises generating the plurality of product ion species by simultaneously reacting the isolated plurality of subsets of the first-generation ion species with the reagent anions within the ion trap for the predetermined time duration.

* * * * *

UNITED STATES PATENT AND TRADEMARK OFFICE
CERTIFICATE OF CORRECTION

PATENT NO. : 10,497,549 B2
APPLICATION NO. : 15/830439
DATED : December 3, 2019
INVENTOR(S) : James L. Stephenson, Jr. et al.

Page 1 of 1

It is certified that error appears in the above-identified patent and that said Letters Patent is hereby corrected as shown below:

Claim 1, Column 42, Line 67:
Replace "ink ratios"
With --m/z ratios--

Signed and Sealed this
Twenty-fourth Day of March, 2020

Andrei Iancu
*Director of the United States Patent and Trademark Office*